US009005620B2

(12) United States Patent
Cruwys et al.

(10) Patent No.: US 9,005,620 B2
(45) Date of Patent: *Apr. 14, 2015

(54) COMPOUNDS

(75) Inventors: Simon Charles Cruwys, Loughborough (GB); Steven Godfrey Lane, Cambridge (GB); Philip Mallinder, Loughborough (GB)

(73) Assignee: MedImmune Limited, Cambridge (GB)

( * ) Notice: Subject to any disclaimer, the term of this patent is extended or adjusted under 35 U.S.C. 154(b) by 23 days.

This patent is subject to a terminal disclaimer.

(21) Appl. No.: 13/480,690

(22) Filed: May 25, 2012

(65) Prior Publication Data

US 2012/0301462 A1  Nov. 29, 2012

Related U.S. Application Data

(63) Continuation of application No. 11/948,659, filed on Nov. 30, 2007, now Pat. No. 8,198,414.

(60) Provisional application No. 60/861,704, filed on Nov. 30, 2006.

(51) Int. Cl.
*A61K 39/395* (2006.01)
*C07K 16/24* (2006.01)
*A61K 39/00* (2006.01)

(52) U.S. Cl.
CPC ......... C07K 16/248 (2013.01); *A61K 2039/505* (2013.01); *C07K 2316/96* (2013.01); *C07K 2317/21* (2013.01); *C07K 2317/56* (2013.01); *C07K 2317/565* (2013.01); *C07K 2317/567* (2013.01); *C07K 2317/622* (2013.01); *C07K 2317/73* (2013.01); *C07K 2317/92* (2013.01); *C07K 2317/34* (2013.01)

(58) Field of Classification Search
USPC ............ 530/350, 387.1, 387.3, 388.23; 424/130.1, 133.1, 145.1; 536/23.5; 435/69.1, 325
See application file for complete search history.

(56) References Cited

U.S. PATENT DOCUMENTS

| 5,856,135 | A | 1/1999 | Tsuchiya et al. |
| 5,888,510 | A | 3/1999 | Kishimoto et al. |
| 6,121,423 | A | 9/2000 | Tsuchiya et al. |
| 6,663,864 | B1 | 12/2003 | Kink et al. |
| 7,291,721 | B2 | 11/2007 | Giles-Komar et al. |
| 7,560,112 | B2 | 7/2009 | Chen et al. |
| 7,612,182 | B2 | 11/2009 | Giles-Komar et al. |
| 2001/0001663 | A1 | 5/2001 | Kishimoto et al. |
| 2004/0039826 | A1 | 2/2004 | Lee |
| 2007/0154481 | A1 | 7/2007 | Gelinas et al. |
| 2007/0178098 | A1 | 8/2007 | Way et al. |
| 2007/0243189 | A1 | 10/2007 | Yoshizaki et al. |
| 2008/0075726 | A1 | 3/2008 | Smith et al. |
| 2008/0090847 | A1 | 4/2008 | Faraday |
| 2008/0145367 | A1 | 6/2008 | Bove et al. |
| 2008/0188401 | A1 | 8/2008 | Cruwys et al. |
| 2008/0312172 | A1 | 12/2008 | Giles-Komar et al. |
| 2009/0104187 | A1 | 4/2009 | Kovacevich |
| 2009/0238825 | A1 | 9/2009 | Kovacevich |
| 2009/0239258 | A1 | 9/2009 | Chen et al. |
| 2009/0263384 | A1 | 10/2009 | Okada et al. |
| 2009/0269335 | A1 | 10/2009 | Nakashima et al. |
| 2009/0291077 | A1 | 11/2009 | Smith et al. |
| 2009/0297535 | A1 | 12/2009 | Kolkman et al. |
| 2010/0015145 | A1 | 1/2010 | Sheriff et al. |
| 2010/0129354 | A1 | 5/2010 | Merchiers et al. |
| 2010/0129357 | A1 | 5/2010 | Garcia-Martinez et al. |
| 2010/0150829 | A1 | 6/2010 | Garcia-Martinez et al. |
| 2010/0158859 | A1 | 6/2010 | Smith et al. |
| 2010/0203009 | A1 | 8/2010 | Weaver et al. |
| 2010/0215654 | A1 | 8/2010 | Bove et al. |
| 2012/0034212 | A1 | 2/2012 | Bowen et al. |

FOREIGN PATENT DOCUMENTS

| EP | 0 399 429 A1 | 11/1990 |
| EP | 0 410 813 B1 | 1/1996 |
| EP | 1 536 012 A1 | 6/2005 |
| EP | 1 715 891 B1 | 4/2010 |
| JP | 10-66582 | 3/1998 |
| WO | WO 03/055979 A3 | 7/2003 |
| WO | WO 2004/020633 A1 | 3/2004 |
| WO | WO 2004/039826 A1 | 5/2004 |
| WO | WO 2004/045507 A2 | 6/2004 |
| WO | WO 2006/072954 A2 | 7/2006 |
| WO | WO 2006/119115 A3 | 11/2006 |
| WO | WO 2008/156807 A2 | 12/2008 |
| WO | WO 2009/026158 A2 | 2/2009 |
| WO | WO 2009/140348 A2 | 11/2009 |
| WO | WO 2010/088444 A1 | 8/2010 |

OTHER PUBLICATIONS

Rudikoff et al (Proc. Natl. Acad. Sci. USA. 1982; 79: 1979-1983).*
Mariuzza et al. (Annu. Rev. Biophys. Biophys. Chem. 1987; 16: 139-159).*
Winkler et al. (J. Immunol. Oct. 15, 2000; 165 (8): 4505-4514).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*

(Continued)

*Primary Examiner* — Stephen Rawlings

(57) ABSTRACT

Binding members, e.g. human antibody molecules, which bind interleukin-6 (IL-6) and neutralize its biological effects. Use of binding members for IL-6 in medical treatment e.g. for treating inflammatory diseases and tumors associated with IL-6.

6 Claims, 1 Drawing Sheet

(56) References Cited

OTHER PUBLICATIONS

Bataille, Régis et al., 1995, "Biologic Effects of Anti-Interleukin-6 Murine Monoclonal Antibody in Advanced Multiple Myeloma", Blood, 86(2):685-691.
Bell, S. J. et al., 2000, "Review article: the clinical role of anti-TNFα antibody treatment in Crohn's Disease", Aliment Pharmacol. Ther., 14:501-514.
Blay, Jean-Yves et al., 1997, "Role of Interleukin-6 in the Paraneoplastic Inflammatory Syndrome Associated With Renal-Cell Carcinoma" Int. J. Cancer, 72:424-430.
Boulanger, Martin J. et al., 2003, "Hexameric Structure and Assembly of the Interleukin-6/IL-6 α-Receptor/gp130 Complex", Science, 300:2101-2104.
Brakenhoff, Just P. J. et al., 1990, "Structure-Function Analysis of Human IL-6 Epitope Mapping of Neutralizing Monoclonal Antibodies with Amino-and Carboxyl-Treatment Deletion Mutants", The Journal of Immunology, 145(2):561-568.
Brakenhoff, Just P. J. et al., 1994, "Development of a Human Interleukin-6 Receptor Antagonist", The Journal of Biological Chemistry, 269(1):86-93.
Brochier, J. et al., 1995, "Immunomodulating IL-6 Activity by Murine Monoclonal Antibodies", Int. J. Immunopharm, 17(1):41-48.
Choy, Ernest, 2004, "Clinical experience with inhibition of interluekin-6", Rheumatic Disease Clinics of North America, 30:405-415.
Davies, Julian et al., 1996, "Affinity improvement of single antibody VH domains: residues in all three hypervariable regions affect antigen binding", Immunotechnology, 2:169-179.
Desgeorges, Alain et al., 1997, "Concentrations and Origins of Soluble Interleukin 6 Receptor-α in Serum and Synovial Fluid", The Journal of. Rheumatology, 24:1510-1516.
Emilie, Dominique et al., 1994, "Administration of an Anti-Interleukin-6 Monoclonal Antibody to Patients With Acquired Immunodeficiency Syndrome and Lymphoma: Effect on Lymphoma Growth and on B Clinical Symptoms", Blood, 84(8):2472-2479.
Ernst, Matthias et al., 2004, "Acquiring signalling specificity from the cytokine receptor gp130", Trends in Genetics, 20(1):23-32.
Fasshauer, M. et al., 2003, "Interleukin (IL)-6 mRNA Expression is Stimulated by Insulin, Isoproterenol, Tumour Necrosis Factor Alpha, Growth Hormone, and IL-6 in 3T3-L1 Adipocytes", Horm Metab Res, 35:147-152.
Guillén, C. et al., 2004, "The Interleukin-6/Soluble Interleukin-6 Receptor System Induces Parathyroid Hormone-Related Protein in Human Osteoblastic Cells", Calcified Tissue International, 75:153-159.
Heinrich, Peter C., et al., 2003, "Principles of interleukin (IL)-6-type cytokine signalling and its regulation", Biochem. J., 374:1-20/.
Hirano, Toshio et al., 1986, "Complementary DNA for a novel human interleukin (BSF-2) that induces B lymphocytes to produce immunoglobulin", Nature, 324:73-76.
Hirata, Yuuichi et al., 1989, "Characterization of IL-6 Receptor Expression by Monoclonal and Polyclonal Antibodies", The Journal of Immunology, 143:2900-2906.
Holt, Lucy J. et al., 2003, "Domain antibodies: proteins for therapy", Trends in Biotechnology, 21(11):484-490.
Jones, Simon A. et al., 2001, "The soluble interleukin 6 receptor: mechanisms of production and implications in disease", FASEB J., 15:43-48.
Kalai, Michael et al., 1996, "Participation of two Ser-Ser-Phe-Tyr repeats in interleukin-6 (IL-6)-binding sites of the human IL-6 receptor", Eur. J. Biochem., 238:714-723.
Kalai, Michael et al., 1997, "Analysis of the mechanism of action of anti-human interleukin-6 and anti-human interleukin-6 receptor-neutralising monoclonal antibodies", Eur. J. Biochem,., 249:690-700.
Kalai, Michael et al., 1997, "Analysis of the Human Interleukin-6/Human Interleukin-6 Receptor Binding Interface at the Amino Acid Level: Proposed Mechanism of Interaction", Blood, 89(4):1319-1333.
Kawano, Michio et al., 1988, "Autocrine generation and requirement of BSF-2/IL-6 for human multiple myelomas", Nature, 332:83-85.
Keller, Evan T. et al., 1996, "Molecular and Cellular Biology of Interleukin-6 and Its Receptor", Frontiers in Bioscience, 1:340-357.
Kishimoto, Tadamitsu, 1989, "The Biology of Interleukin-6", Blood, 74(1):1-10.
Kishimoto, Tadamistu, 2006, "Interleukin-6:discovery of a pleiotropic cytokine", Arthritis Research & Therapy, 8:Supp1. 2:S2:1-6.
Klouche, Mariam et al., 1999, "Novel Path to Activation of Vascular Smooth Muscle Cells: Up-Regulation of gp130 Creates an Autocrine Activation Loop by IL-6 and Its Soluble Receptor", The Journal of Immunology, 163:4583-4589.
Lu, Zhao Yang et al., 1995, "Measurement of Whole Body Interleukin-6 (IL-6) Production: Prediction of the Efficacy of Anti-IL-6 Treatments", Blood, 86(8):3123-3131.
März, Pia et al., 1998, "Sympathetic neurons can produce and respond to interleukin 6", 95:3251-3256.
Menziani, M.C. et al., 1997, "Theoretical Investigation of IL-6 Multiprotein Receptor Assembly", Proteins: Structure, Function and Genetics, 29:528-544.
Mihara, Masahiko et al., 2005, "The therapy of autoimmune diseases by anti-interleukin-6 receptor antibody", Expert Opinion on Biological Therapy, 5(5):683-690.
Modur, Vijayanand et al., 1997, "Retrograde Inflammatory Signaling from Neutrophils to Endothelial Cells by Soluble Interleukin-6 Receptor Alpha", J. Clin. Invest., 100(11):2752-2756.
Moshage, Han, 1997, "Cytokines and the Hepatic Acute Phase Response", Journal of Pathology, 181:257-266.
Murakami, Masaji et al., 1996, "Inducible Expression of Glial Fibrillary Acidic Protein in HT-1080 Human Fibrosarcoma Cells", Cell Growth & Differentiation, 7:1697-1703.
Nishimoto, Norihiro et al., 2004, "Inhibition of IL-6 for the treatment of inflammatory diseases", Current Opinion in Pharmacology, 4:386-391.
Oh, Jae-Wook et al., 2001, "CXC Chemokine Receptor 4 Expression and Function in Human Astroglioma Cells", The Journal of Immunology, 166:2695-2704.
Smith, Peter C. et al., 2001, "Interleukin-6 and prostate cancer progression" Cytokine and Growth Factor Reviews, 12:33-40.
Somers, William et al., 1997, "1.9 Å crystal structure of interleukin 6: implications for a novel mdoe of receptor dimerization and signaling", The EMBO Journal, 16(5):989-997.
Tamura, Tatsuya et al., 1993, "Soluble interleukin-6 receptor triggers osteoclast formation by interleukin 6", Proc. Natl. Acd. Sci. USA, 90:11924-11928.
Udagawa, Nobuyuki et al., 1995, "Interleukin (IL)-6 Induction of Osteoclast Differentiation Depends on IL-6 Receptors Expressed on Osteoblastic Cells But Not on Osteoclast Progenitors", J. Exp. Med., 1461-1468.
Varghese, J.N. et al., 2002, "Structure of the extracellular domains of the human interleukin-6 receptor α-chain", PNAS, 99(25):15959-15964.
Wallenius, Ville et al., 2002, "Interleukin-6-deficient mice develop mature-onset obesity", Nature Medicine, 8(1):75-79.
Wendling, Daniel et al., 1993, "Treatment of Severe Rheumatoid Arthritis by Anti-Interleukin 6 Monoclonal Antibody", The Journal of Rheumatology,20:259-262.
Wijdenes, John et al., 1991, "Human Recombinant Dimeric IL-6 Binds to Its Receptor As Detected by Anti-IL-6 Monoclonal Antibodies", Molecular Immunology, 28(11): 1183-1192.
Yokota, Shumpei et al., 2005, "Therapeutic Efficacy of Humanized Recombinant Anti-Interleukin-6 Receptor Antibody in Children With Systemic-Onset Juvenile Idiopathic Arthritis", Arthritis & Rheumatism, 52(3):818-825.
Yoshida, Kanji et al., 1996, "Targeted disruption of gp130, a common signal transducer for the interleukin 6 family of cytokines, leads to myocardial and hematological disorders", Proc. Natl. Acad. Sci. USA, 93:407-411.
Zaanen, van H.C.T. et al., 1996, "Endogenous Interleukin 6 Production in Multiple Myeloma Patients Treated with Chimeric Monoclonal Anti-IL-6 Antibodies Indicates the Existence of a Positive Feed-back Loop", J. Clin. Invest., 98(6):1441-1448.

(56) References Cited

OTHER PUBLICATIONS

Zaanen, van H.C.T. et al., 1998, "Chimaeric anti-interleukin 6 monoclonal antibodies in the treatment of advanced multiple myeloma: a phase I dose-escalating study", Bristish Journal of Haematology,102:783-790.

Caldas et al., May 2003, Mol. Immunol., 39(15):941-952.

Vajdos et al., Jul. 5, 2002, J. Mol. Biol., 320(2):415-428.

De Pascalis et al., 2002, J. Immunol., 169(6):3076-3084.

Holm et al., Feb. 2007, Mol. Immunol., 44(6):1075-1084.

Mariuzza et al., 1987, Annu. Rev. Biophys. Biophys. Chem., 16:139-159.

Gussow et al., 1991, Methods in Enzymology, 203:99-121.

Giusti et al., May 1987, Proc. Natl. Sci. USA, 84(9):2926-2930.

Chien et al., 19890 Jul., Proc. Natl. Sci. USA, 86(14):5532-5536.

* cited by examiner

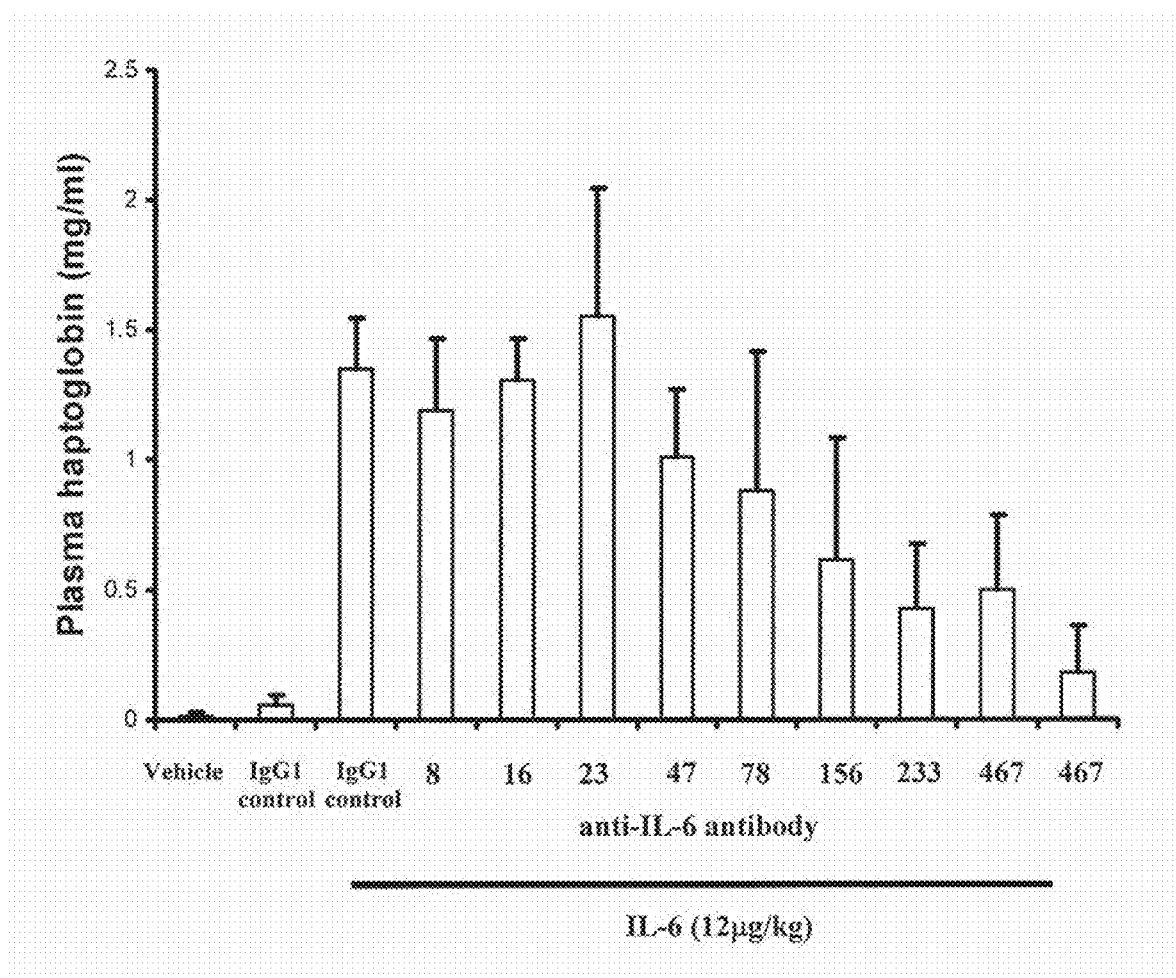

COMPOUNDS

This application is a continuation of U.S. application Ser. No. 11/948,659 filed on Nov. 30, 2007, now U.S. Pat. No. 8,198,414 issued Jun. 12, 2012, said application Ser. No. 11/948,659 claims benefit under 35 U.S.C. §119(e) of U.S. Provisional Application No. 60/861,704 filed Nov. 30, 2006. Each of the above listed applications is incorporated by reference herein in its entirety for all purposes.

The instant application contains a Sequence Listing which has been submitted in ASCII format via EFS-Web and is hereby incorporated by reference in its entirety. Said ASCII copy, created on Jun. 21, 2012, is named IL6102US.txt and is 108,418 bytes in size.

This invention relates to binding members, especially antibody molecules, which inhibit biological effects of IL-6. The binding members are useful for treatment of disorders associated with IL-6, including inflammatory diseases and tumours.

Interleukin 6 (IL-6) is a 26 kDa pleiotropic pro-inflammatory cytokine produced by a variety of cell types, including stimulated fibroblasts, monocytes and endothelial cells, which form the major source of IL-6 in vivo. Cells such as T cells, B cells, macrophages, keratinocytes, osteoblasts and several others can produce IL-6 on stimulation. IL-6 is also expressed from tumour cell lines and tumour cells e.g. cells from lung carcinoma, prostate cancer, myeloma, hypernephroma and cardiac myxoma [1, 2]. Under non-inflammatory conditions, IL-6 is secreted from adipose tissue [3].

The regulation of IL-6 expression depends on the cell type that is producing it. In multiple myeloma cells IL-6 appears to act in a positive feedback loop—stimulating the cells to grow as well as produce more IL-6 [4, 5]. In other cell types IL-6 appears to inhibit the growth and activation of cells and may act as a negative regulator for some pro-inflammatory cytokines.

To initiate cell signalling, IL-6 binds with low affinity to a transmembrane receptor, IL-6 receptor alpha (also referred to as IL-6Rα, IL-6Ra, IL-6R, gp80 or CD126) to form a complex "IL-6:IL-6Ra". This complex binds to the gp130 signal receptor; IL-6Rα and gp130 together form a high affinity IL-6 binding site, and induce the formation of a hexamer composed of two copies each of IL-6, IL-6Ra and gp130 [6]. The transmembrane and cytoplasmic domains of the IL-6Ra are not required for signal transduction, as IL-6Ra also exists as a soluble secreted form (sIL-6R or sIL-6Ra). The soluble receptor is produced either by differential splicing of the IL-6Ra message or by proteolytic shedding. sIL-6R is capable of forming a ligand-receptor complex with IL-6, "IL-6:sIL-6Ra". This complex can bind gp130 on cells and thereby initiate cell signalling in gp130 positive cells, even if those cells do not express IL-6Ra. Thus, sIL-6R has the potential to widen the repertoire of cells responsive to IL-6, and is thought to play an important role in IL-6-mediated inflammation [7].

A crystal structure of human IL-6 ligand has been elucidated [6]. The crystal structure of the extracellular domain of human IL-6Ra [8], and the hexameric structure of IL-6/IL-6R/gp130 complex [9], have also been resolved. These structures combined with mutagenesis studies have identified three sites on the surface of IL-6 which are involved in the functional activity of the IL-6 in complex with the various receptor components. Site 1 residues are involved in the interaction between IL-6 and IL-6Ra. Site 2 residues are involved in the interaction between IL-6 and the gp130 cytokine binding domain. The residues in Site 3 of IL-6 are involved in interacting with the Ig-like domain of the second gp130 in the hexameric complex. A fourth site on IL-6 has also been identified where IL-6 interacts with the second molecule of IL-6 in the hexameric IL-6/IL-6R/gp130 complex [10].

A number of anti-IL-6 ligand monoclonal antibodies have been isolated. Mapping studies have been performed which show that these bind to different binding sites, as described above, on the surface of human IL-6 [11, 12, 13, 14, 15].

A number of anti-IL-6Ra monoclonal antibodies have also been generated and their binding sites on the IL-6Ra mapped [16, 14, 15, 17].

IL-6 belongs to a family of cytokines, which includes Interleukin-11 (IL-11), ciliary neurotrophic factor (CNTF), Oncostatin M (OsM), Leukaemia Inhibitory Factor (LIF), cardiotrophin-like cytokine (CLC), and Cardiotrophin 1 (CT-1). Each of the members of this family have their own specific receptor alpha subunits and form complexes with the common receptor subunit gp130. Targeted disruption of the gp130 gene is embryonically lethal [18, 19]. All members of the IL-6 family can induce the expression of acute phase proteins from hepatocytes.

IL-6 signalling involves tyrosine phosphorylation by JAK family kinases, and subsequent activation of two major intracellular signalling cascades, the SHP2/ERK MAPK and STAT1/3 pathways, leading to gene expression via NF-IL-6 and AP-1 [18, 20].

IL-6 shows a wide spectrum of biological functions including: haematopoiesis, induction of acute phase responses, T cell activation, stimulation of antibody secretion, host defense against infection, myeloma cell and osteoclast activation [21, 22]. For a review of the effects of IL-6 see ref. [23]. IL-6 was originally identified as a B-cell differentiation factor generated by T cells [24] but has subsequently been identified as a potent activator and growth-promoting factor of many cell types. It induces the final maturation of B cells into antibody producing cells and is an essential accessory factor for T cell activation and proliferation. Studies have shown that IL-6 is involved in the activation of auto-reactive T lymphocytes and the proliferation and differentiation of cytotoxic T cells. IL-6 has been implicated in haematopoiesis as a cofactor causing the activation and differentiation of haemopoietic stem cells. The effect of IL-6 on the acute phase response is also well documented [25]. IL-6 induces a variety of acute phase proteins including fibrinogen, alpha-anti-chymotrypsin, serum amyloid A and C-reactive protein from human hepatocytes. Acute phase proteins control immune responses and inflammation and have effects on tissue remodelling. The serum level of IL-6 correlates well with that of C-reactive protein in variety of pathologies suggesting a causal role of IL-6 in the acute phase response. IL-6 has also been shown to be produced by osteoblasts and appears to be involved in osteoclast activation and bone resorption [26, 27, 28]. Paradoxically it has been suggested that IL-6 not only has roles as a pro-inflammatory cytokine but can also, in certain circumstances and cell types, dampen the effects of other pro-inflammatory cytokines leading to a reduction in inflammation.

Because IL-6 has a variety of biological effects, the elevation of IL-6 has been implicated as a key cytokine in a variety of disease indications. The levels of circulating IL-6 have been shown to be elevated in diseases such as rheumatoid arthritis, Castleman's disease, Juvenile idiopathic arthritis and Crohn's Disease [29]. Because of this IL-6 has been implicated in driving the pathology in these inflammatory indications. Furthermore, a variety of tumour types have been shown to be stimulated by IL-6, including melanoma, renal cell carcinoma, Kaposi's sarcoma, ovarian carcinoma, lymphoma, leukaemia, multiple myeloma, and prostate carcinoma [30]. Moreover increased circulating levels of IL-6 have been reported in several cancers. In some cancer indications elevated IL-6 levels has been used as prognostic indicators of the disease.

Because of the role of IL-6 in disease a variety of murine and chimeric anti-human IL-6 monoclonal antibodies have been developed as potential therapies.

U.S. Pat. No. 5,856,135 describes a reshaped human antibody to IL-6, derived from a mouse monoclonal antibody "SK2".

JP-10-66582 reports a chimeric antibody to IL-6, which is indicated as recognising the helix D region of IL-6 (site 1).

WO2004/020633 (EP1536012) describes a human scFv antibody molecule to IL-6 isolated using phage display technology. The scFv is reported to have an affinity of 13 nM.

A murine anti-IL-6 antibody, elsilimomab (also known as B-E8) has been used to treat patients with Multiple myeloma [31, 32] renal cell carcinoma [33] and rheumatoid arthritis [34] and improvements in certain diagnostic markers were seen in treated patients with all three diseases. BE-8 has also been used to treat HIV-positive patients with immunoblastic or polymorphic large cell lymphoma [35] with relief of systemic symptoms (i.e. fever, sweats, cachexia) and suppression of spontaneous growth of the lymphoma in approximately 50% of patients.

However, the rapid clearance of this antibody and possible anaphylactic reactions due to the production of human anti-mouse antibodies (HAMA) to elsilimomab has limited its use in the clinic [36].

In general, clinical use of murine monoclonal antibodies is limited, as such antibodies frequently induce HAMA. HAMA directed against the Fc part of the mouse immunoglobulin are often produced, resulting in rapid clearance of anti-IL-6 mAb and possible anaphylactic reaction [36]. It is also known that the pharmacokinetics of mouse antibodies in humans is different from human antibodies having shorter half lives and increased rates of clearance.

To reduce the immunogenicity of murine antibodies in humans, chimeric antibodies with mouse variable regions and human constant regions have been constructed. A chimeric human-mouse anti-IL-6 antibody cCLB8 (known as CNTO 328) has been used to treat patients with multiple myeloma [5, 37], with disease stabilisation seen in the majority of patients.

However, although chimeric antibodies are less immunogenic than murine MAbs, human anti-chimeric antibody (HACAs) responses have been reported [38].

Mapping studies on cCLB8 have been carried out which show it is a site I inhibitor of IL-6 activity. Brakenhoff et al [39] demonstrated that cCLB8 binds to IL-6 amino-terminal deletion mutants Pro46, Ser49, Glu51, Ile53, Asp54 and also binds to deletion mutants Asp62 and Met77 (albeit at reduced affinity). The same authors show that cCLB8 inhibits wild type IL-6 but not C-terminal deletion 5 in a B9 cell proliferation assay and that cCLB8 will not bind IL-6 del C-4 which has the last 4 C-terminal amino acids residues deleted. This data suggest that cCLB8 binds to an epitope involving the C-terminal residues of IL-6.

Kalai et al [17] demonstrated that cCLB8 failed to recognise IL-6 mutants F106E, F102E/F106E or R207E/R210E. However the antibody does recognise IL-6 mutants R207E and R207W. The binding of cCLB8 to mutants R207W & R207E is approximately 50% of that compared to wild type, which suggests that residues F106 and R210 are involved in the cCLB8 binding epitope and residue R207 is involved in binding but has less effect than residues F106 and R210. The cCLB8 binds IL-6 site-I mutants R196M, K199N/Q203L and Q203L with 100% activity compared to wild type. Brakenhoff et al [13] demonstrated that cCLB8 binds the following IL-6 variants; Q182H, N183K, W185Q, W185G, W185R, T190P, Q182H/Q184P, W185R/S197N, Q187E/T190P, I164L/L186R/M189I, which is not surprising as the majority of these are distally separated from the IL-6 site 1 residues.

The positive effect of inhibiting IL-6 signalling in cancer and inflammatory diseases has been further highlighted by the use of a humanised anti-IL-6Ra antibody Tocilizumab (also known as hPM-1, MRA and Actemra). This is a humanised version of the murine anti-IL6Ra antibody PM-1. Treatment of patients with this antibody has proven effective in a number of diseases including rheumatoid arthritis, Juvenile idiopathic arthritis, Crohn's disease, Myeloproliferative disorder, Castleman's disease and Systemic lupus erythematosus [40].

We have succeeded in isolating highly potent, high affinity binding members for IL-6. Owing to their high affinity and potency, and their performance in functional studies as described herein, binding members of the invention are particularly suitable for use in therapeutic and/or diagnostic treatment of the human or animal body.

The binding members are useful for treating disorders associated with IL-6, as described in detail elsewhere herein.

A human anti-IL-6 antibody for the treatment of inflammatory diseases and cancer provides significant advantages over existing approaches. For example, human antibodies do not induce HAMA or HACA responses, and have a longer in vivo half life compared with non-human or chimeric antibodies.

We have also recognised that binding members for IL-6 offer significant advantages as compared with binding members for IL-6Ra, especially in terms of in vivo administration and treatment, as described elsewhere herein.

As described in more detail in the Examples, we isolated a parent antibody molecule, designated CAN022D10, with a set of CDR sequences as shown in Table 7. Through a process of optimisation we generated a panel of antibody clones: Antibodies 2, 3, 4, 5, 7, 8, 10, 14, 16, 17, 18, 19, 21, 22 and 23, with CDR sequences derived from the parent CDR sequences and having substitutions at the positions indicated in Table 7.

Thus for example it can be seen from Table 7 that Antibody 2 has a parent HCDR1 sequence in which Kabat residue 35 is replaced with Thr (SEQ ID NO: 13). Antibodies 14 and 22 contain an additional residue, i.e. an amino acid insertion, in HCDR3: Ile at Kabat residue 100D, which is not present in the parent HCDR3 sequence SEQ ID NO: 5. Antibodies 7, 8, 10, 16-19, 21 and 23 do not contain Kabat residue 95 in LCDR3, whereas the parent LCDR3 (SEQ ID NO: 10) comprises Pro at Kabat residue 95. The parent HCDR3, and HCDR3 sequences of all of antibodies 2, 3, 4, 5, 7, 8, 10, 14, 16, 17, 18, 19, 21, 22 and 23 have Trp at Kabat residue 95 and Asp at Kabat residue 101, indicating that H95 Trp and H101 Asp may contribute to binding and/or potency for IL-6 in binding members of the invention.

VH domain, VL domain and CDR sequences of the parent antibody CAN022D10, and of antibodies 2, 3, 4, 5, 7, 8, 10, 14, 16, 17, 18, 19, 21, 22 and 23 as described herein are shown in the appended sequence listing.

As described in more detail below, binding members according to the invention have been shown to neutralise IL-6 with high potency. Neutralisation means inhibition of a biological activity of IL-6. Binding members of the invention may neutralise one or more activities of IL-6. The inhibited biological activity is typically IL-6 binding to one or more of its binding partners. For example, the inhibited biological activity may be binding of IL-6 to transmembrane and/or soluble IL-6Rα. This is demonstrated in the following assays, which are described briefly here and in more detail below: The TF-1 assay shows that binding members according to the invention inhibit IL-6 binding to membrane IL-6Ra as the TF-1 cells do not appear to produce soluble IL-6Ra. As such, the binding members of the invention therefore inhibit IL-6 binding to the membrane receptor. In the synovial fibroblast assay, binding members according to the invention inhibit IL-6 binding to soluble IL-6Ra since sIL-6Ra needs to be added to this assay for it to work. The added IL-1beta induces production of endogenous IL-6 which when inhibited by a binding member of this invention prevents VEGF production.

In accordance with the invention, binding of human or non-human primate, e.g. cynomolgus, IL-6 to IL-6Rα may be inhibited, e.g. a binding member may inhibit binding of mature human IL-6 to IL-6Rα.

Inhibition in biological activity may be partial or total. Binding members may inhibit IL-6 biological activity by 100%, or at least 95%, at least 90%, at least 85%, at least 80%, at least 75%, at least 70%, at least 60%, or at least 50% of the activity in absence of the binding member.

Neutralising potency of a binding member may be determined. Potency is normally expressed as an $IC_{50}$ value, in nM unless otherwise stated. In functional assays, $IC_{50}$ is the concentration of a binding member that reduces a biological response by 50% of its maximum. In ligand-binding studies, $IC_{50}$ is the concentration that reduces formation of the ligand-receptor complex by 50% of the maximal specific binding level. $IC_{50}$ may be calculated by plotting % of maximal biological response as a function of the log of the binding member concentration, and using a software program, such as Prism (GraphPad) or Origin (Origin Labs) to fit a sigmoidal function to the data to generate $IC_{50}$ values. Potency may be determined or measured using one or more assays known to the skilled person and/or as described or referred to herein.

Neutralisation of IL-6 activity by a binding member in an assay described herein, e.g. the TF-1 proliferation assay or other cell-based assays described below, indicates that the binding member binds and neutralises IL-6. Other methods that may be used for determining binding of a binding member to IL-6 include ELISA, Western blotting, immunoprecipitation, affinity chromatography and biochemical assays.

Binding members described herein were demonstrated to bind and neutralise biological effects of endogenous human IL-6, as shown in an assay of inhibition of VEGF release from human synovial fibroblasts in response to endogenous human IL-6, reported in Examples 1.7 and 2.7 herein. In this assay, synovial fibroblasts from rheumatoid arthritis patients produce IL-6 in response to stimulation with IL-1β and soluble IL-6Rα, leading to IL-6 induced secretion of VEGF. The IL-6 produced by the human synovial fibroblasts thus represents endogenous human IL-6. Endogenous IL-6 is the molecular target for medical treatment in humans, so neutralisation of endogenous IL-6 is an important indicator of the therapeutic potential of the binding members. Since the assays were conducted with synovial fibroblasts obtained from rheumatoid arthritis patients, the results are particularly relevant to use of the binding members for treating rheumatoid arthritis. Neutralising potency of optimised antibody molecules tested in the VEGF release assay surpassed that of the known anti Il-6 antibody CNTO-328.

A binding member according to the invention may have an $IC_{50}$ of less than 50 nM, e.g. less than 5 nM, e.g. less than 1 nM in an assay of inhibition of VEGF release from human synovial fibroblasts stimulated with 0.6 pM human IL-1β and 2.4 nM soluble human IL-6Rα.

Endogenous IL-6 is known to be a mixture of glycosylated and unglycosylated forms. Binding of a binding member of the invention to endogenous IL-6 has been demonstrated in the synovial fibroblast assay since this assay utilises IL-6 from human synovial fibroblasts i.e. endogenous IL-6.

A binding member of the invention may inhibit IL-6 induced proliferation of TF-1 cells. TF-1 is a human premyeloid cell line established from a patient with erythroleukaemia (Kitamura et al 1989). The TF-1 cell line requires the presence of a growth factor for survival and proliferation. The individual growth factors TF-1 cells can respond to include IL-6, GM-CSF and Oncostatin M. A binding member of the invention may have an $IC_{50}$ of less than 100 nM, e.g. less than 20 nM, 10 nM or 1 nM, e.g. less than 100 pM, 70 pM, 50 pM, 40 pM, 30 pM, 20 pM or 10 pM, in an assay for inhibition of proliferation of TF-1 cells in response to 20 pM human IL-6. As described herein (see Example 1.5), a parent IgG "CAN022D10" was shown to have an IC50 in the TF-1 proliferation assay of about 93 nM, and we subsequently generated optimised variants of CAN022D10 having substantially increased potency ($IC_{50}$ generally less than 100 pM), as shown in Examples 2.2, 2.5 and 2.6 (Tables 3, 4 and 5, respectively). Notably, $IC_{50}$ values for some of the optimised clones were measured to be low as 5 pM or less, for example the germlined IgG Antibody 7, Antibody 17 and Antibody 18, representing extremely high neutralising potency of these antibodies.

A binding member of the invention may inhibit IL-6 induced proliferation of B9 cells. B9 cells are a sub-clone of the murine B-cell hybridoma cell line, B13.29, selected on the basis of their specific response to IL-6. B9 cells require IL-6 for survival and proliferation and respond to very low concentrations of IL-6. As such, proliferation of these cells in the presence of an IL-6 antibody can be assessed and the affinity of the antibody determined. Example 2.10 herein shows that Antibody 18 inhibited B9 cell proliferation in response to IL-6, and showed high affinity in this assay.

Auto-antibody production in rheumatoid arthritis is mostly of the IgM class. SKW6.4 is a clonal IgM secreting human lymphoblastoid B cell line. Upon stimulation with IL-6 these cells secrete IgM, thus this assay was perceived to be relevant to rheumatoid arthritis. SKW6.4 cells may be used in an assay to determine potency of binding members for neutralising IL-6, by determining inhibition of IgM secretion in response to IL-6. A binding member of the invention may have an $IC_{50}$ of less than 10 pM, e.g. less than 5 pM, in an SKW6.4 cell assay of inhibition of IgM secretion in response to 100 pM human IL-6. Antibody 18 was shown to neutralise effects of IL-6 in this assay—see Example 2.11 (Table 9).

The invention provides high affinity binding members for human IL-6. High affinity for IL-6 from cynomolgus monkey was also demonstrated. A binding member of the invention may bind human IL-6 and/or cynomolgus IL-6 with a $K_D$ of not more than 1 nM, e.g. not more than 100 pM, 50 pM, 30 pM or 10 pM. The $K_D$ may be determined by surface plasmon resonance, e.g. BIAcore®. BIAcore® measurements of affinity are described herein in Example 2.9. Remarkably, the affinity of Antibodies 7 and 18 was found to be beyond the limit measurable using the BIAcore® instrument, indicating a $K_D$ value below 10 pM.

As described elsewhere herein, surface plasmon resonance involves passing an analyte in fluid phase over a ligand attached to a support, and determining binding between analyte and ligand. Surface plasmon resonance may for example be performed whereby IL-6 is passed in fluid phase over a binding member attached to a support. Surface plasmon resonance data may be fitted to a monovalent analyte data model. An affinity constant Kd may be calculated from the ratio of rate constants kd/ka as determined by surface plasmon resonance using a monovalent analyte data model.

Affinity of a binding member for IL-16 may alternatively be calculated by Schild analysis, e.g. based on an assay of inhibition of TF-1 cell proliferation in response to varied concentrations of human IL-6. A binding member of the invention may have an affinity of less than 10 pM, e.g. less than 1 pM, as calculated by Schild analysis. As reported in Example 2.10 herein, the affinity of Antibody 18 for human IL-6 was calculated as 0.4 pM using Schild analysis.

A binding member of the invention may optionally not cross-react with one or more, or all, of the following: leukaemia inhibitory factor (LIF), ciliary neurotrophic factor (CNTF), IL-11 or oncostatin M.

A binding member of the invention may optionally not cross-react with rat IL-6, mouse IL-6 and/or dog IL-6.

Cross-reactivity of binding members for binding other proteins or non-human IL-6 may be tested for example in a time resolved fluorescence assay for inhibition of human IL-6 binding to the binding member immobilised on a support, such as the DELFIA® epitope competition assay as described in Example 1.6. For example, any or all of LIF, CNTF, IL-11, oncostatin M, rat IL-6 and mouse IL-6 may show no inhibition, less than 50% inhibition, or may have an $IC_{50}$ greater than 0.5 mM or greater than 1 mM in the time resolved fluorescence assay for inhibition of labelled human IL-6 binding to the binding member immobilised on a support. For example, any or all of LIF, CNTF, IL-11, oncostatin M, rat IL-6 and mouse IL-6 may show no inhibition or may have an $IC_{50}$ at least 10- or 100-fold greater than that of unlabelled human IL-6 in the time resolved fluorescence assay for testing cross-reactivity. In this assay, labelled wild type mature human IL-6 is used at a final concentration of the Kd of its interaction with the binding member.

A binding member of the invention may cross-react with cynomolgus IL-6. Cross-reactivity may be determined as inhibition of labelled human IL-6 binding to the binding member immobilised on a support, in the time resolved fluorescence assay described above. For example, cynomolgus IL-6 may have an $IC_{50}$ of less than 5 nM, e.g. less than 2.5 nM, e.g. about 1 nM, in this time resolved fluorescence assay. Cynomolgus IL-6 may have an $IC_{50}$ less than 10-fold different, e.g. less than 5-fold different, from the $IC_{50}$ of unlabelled human IL-6 in this assay.

A detailed protocol for the time resolved fluorescence assay for determining cross-reactivity is provided in the Materials and Methods section. Examples of cross-reactivity data obtained in this assay are shown in Table 2 in Example 1.6.

As reported in Example 2.8, binding members described herein showed high cross-reactivity with cynomolgus IL-6, and showed no or limited cross-reactivity with rat, mouse or dog IL-6.

The cross-reactivity data indicate that the binding members described herein bind an epitope on IL-6 that is conserved between the human and cynomolgus IL-6 sequences, and is different in the mouse, rat and dog IL-6 sequence compared with the human sequence.

The binding members described herein are believed to bind the "site 1" region of IL-6, which is the region that interacts with IL-6Rα. Binding members of the invention may thus competitively inhibit IL-6 binding to IL-6Rα, thereby neutralising biological effects of IL-6 that are mediated through IL-6Rα.

We investigated the ability of one of the antibodies described herein, Antibody 18, to bind mutant human IL-6, in which mutations were engineered in site 1 residues. As described in Example 3, we identified mutations in human IL-6 that resulted in reduced binding by Antibody 18, indicating that the mutated residues were involved in recognition by Antibody 18 and may form part of the epitope on IL-6 bound by this antibody.

For example, in a time resolved fluorescence assay for inhibition of labelled wild type human IL-6 binding to Antibody 18 immobilised on a support, no inhibition was observed for Arg207Glu mutant human IL-6 (SEQ ID NO: 177), indicating that Antibody 18 binds human IL-6 at residue Arg207.

Since Antibody 18 and Antibodies 2, 3, 4, 5, 7, 8, 10, 14, 16, 17, 19, 21, 22 and 23 were all derived from a parent antibody CAN22C10, and all have structurally related CDRs, all these antibody molecules are expected to bind the same or very similar overlapping epitope. Accordingly, the epitope mapping results obtained with Antibody 18 are also expected to be representative for CAN22D10 the other optimised antibodies described herein.

A binding member of the invention may bind human IL-6 at Phe102 and/or Ser204. A binding member of the invention may also bind human IL-6 at Arg207. Optionally a binding member may bind flanking residues or structurally neighbouring residues in the IL-6 molecule, in addition to binding Phe102 and/or Ser 204. By convention, residue numbering corresponds to full length human IL-6 (SEQ ID NO: 161). However, binding may be determined using mature human IL-6. Binding to IL-6 residues is as determined by site directed mutagenesis, as explained below.

Mutagenesis of single amino acids and regions of proteins in order to correlate structure with activity is well known to one skilled in the art and has been used to define regions of proteins that bind to antibodies [41]. Binding to and/or neutralisation of mutant human IL-6 may be used to assess whether a binding member binds Phe102, Ser204 and/or Arg207. Absence of binding or neutralisation, or significantly reduced binding or neutralisation, with mutant IL-6 compared with wild-type indicates that a binding member binds the mutated residue.

Binding to a residue in IL-6 may be determined using IL-6 mutated at the selected residue in a time resolved fluorescence assay of inhibition of labelled wild type human IL-6 binding to the binding member immobilised on a support, wherein the labelled wild type mature human IL-6 is at a final concentration equal to the Kd of its interaction with the binding member. An example of this assay and competition data obtained are shown in Example 3, with results presented in Table 10. Where the mutant IL-6 does not inhibit binding of labelled wild type IL-6 to the binding member, or where the mutant IL-6 has an IC50 greater than that of unlabelled wild type IL-6 (e.g. more than 10-fold or 100-fold greater), this indicates that the mutated residue is bound by the binding member.

Phe102Glu mutant human IL-6 (SEQ ID NO: 175), Ser204Glu mutant human IL-6 (SEQ ID NO: 176), and/or Arg207Glu mutant human IL-6 (SEQ ID NO: 177) may show no inhibition, or may have an $IC_{50}$ more than 100 fold greater than the $IC_{50}$ of wild type human IL-6 (SEQ ID NO: 165), in a time resolved fluorescence assay for inhibition of labelled wild type human IL-6 binding to a binding member of the invention immobilised on a support, wherein the labelled wild type human IL-6 is at a final concentration equal to the Kd of its interaction with the binding member.

A binding member of the invention may optionally not bind and/or neutralise mutant human IL-6 having a mutation at residue Phe102, Ser204 and/or Arg207, e.g. mutation Phe102Glu, Ser204Glu, Ser204Tyr and/or Arg207Glu. Examples of mutant human IL-6 sequences are SEQ ID NOS:

175-177). Thus, a binding member of the invention may not inhibit binding of one or more of these mutant IL-6 molecules to IL-6Rα.

A binding member of the invention may comprise an antibody molecule, e.g. a human antibody molecule. The binding member normally comprises an antibody VH and/or VL domain. VH and VL domains of binding members are also provided as part of the invention. Within each of the VH and VL domains are complementarity determining regions, ("CDRs"), and framework regions, ("FRs"). A VH domain comprises a set of HCDRs, and a VL domain comprises a set of LCDRs. An antibody molecule may comprise an antibody VH domain comprising a VH CDR1, CDR2 and CDR3 and a framework. It may alternatively or also comprise an antibody VL domain comprising a VL CDR1, CDR2 and CDR3 and a framework. A VH or VL domain framework comprises four framework regions, FR1, FR2, FR3 and FR4, interspersed with CDRs in the following structure:

FR1-CDR1-FR2-CDR2-FR3-CDR3-FR4.

Examples of antibody VH and VL domains and CDRs according to the present invention are as listed in the appended sequence listing that forms part of the present disclosure. Further CDRs are disclosed below and in Table 7. All VH and VL sequences, CDR sequences, sets of CDRs and sets of HCDRs and sets of LCDRs disclosed herein represent aspects and embodiments of the invention. As described herein, a "set of CDRs" comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a "set of CDRs" includes HCDRs and LCDRs. Typically binding members of the invention are monoclonal antibodies.

A binding member of the invention may comprise an antigen-binding site within a non-antibody molecule, normally provided by one or more CDRs e.g. a set of CDRs in a non-antibody protein scaffold, as discussed further below.

Described herein is a binding member comprising the parent set of CDRs as shown in Table 7 for parent CAN022D10, in which HCDR1 is SEQ ID NO: 3 (Kabat residues 31-35), HCDR2 is SEQ ID NO: 4 (Kabat residues 50-65), HCDR3 is SEQ ID NO: 5 (Kabat residues 95-102), LCDR1 is SEQ ID NO: 8 (Kabat residues 24-34), LCDR2 is SEQ ID NO: 9 (Kabat residues 50-56) and LCDR3 is SEQ ID NO: 10 (Kabat residues 89-97).

A binding member of the invention may comprise one or more CDRs as described herein, e.g. a CDR3, and optionally also a CDR1 and CDR2 to form a set of CDRs. The CDR or set of CDRs may be a parent CDR or parent set of CDRs, or may be a CDR or set of CDRs of any of antibodies 2, 3, 4, 5, 7, 8, 10, 14, 16, 17, 18, 19, 21, 22 or 23, or may be a variant thereof as described herein.

For example, a binding member or a VL domain according to the invention may comprise an LCDR3 having amino acid sequence SEQ ID NO: 120.

A binding member may comprise a set of H and/or L CDRs of the parent antibody or any of antibodies 2, 3, 4, 5, 7, 8, 10, 14, 16, 17, 18, 19, 21, 22 or 23 with one or more amino acid mutations within the disclosed set of H and/or L CDRs. Amino acid mutations are substitutions, deletions or insertions of one amino acid. For example, there may be up to 20, e.g. up to 12, 11, 10, 9, 8, 7, 6, 5, 4, 3 or 2 mutations e.g. substitutions, within the set of H and/or L CDRs. For example, there may be up to 6, 5, 4, 3 or 2 mutations, e.g. substitutions, in HCDR3 and/or there may be up to 6, 5, 4, 3, or 2 mutations, e.g. substitutions, in LCDR3. HCDR3 and/or LCDR3 may optionally contain an insertion or deletion of one amino acid as compared with the disclosed set of H and/or L CDRs. Substitutions may for example be at the positions substituted in any of Antibodies 2, 3, 4, 5, 7, 8, 10, 14, 16, 17, 18, 19, 21, 22 or 23, as shown in Table 7. Thus, substitutions may optionally be at Kabat numbers selected from the following:

Kabat residue 35 in HCDR1;
Kabat residue 64 in HCDR2;
Kabat residue 96, 97, 98, 99, 100, 100A, 100B, 100C and/or 102 in HCDR3;
Kabat residue 34 in LCDR1;
Kabat residue 89, 90, 91, 92, 93, 94, 96 or 97 in LCDR3.

The amino acid mutations may comprise mutations as shown in Table 7, e.g. amino acid substitutions as indicated.

For example, a binding member or a VH domain according to the invention may comprise the parent HCDR1 with Kabat residue Ile 35 replaced by Thr or Val.

A binding member or a VH domain according to the invention may comprise the parent HCDR2 with Kabat residue Lys 64 replaced by Arg.

A binding member or a VH domain may comprise the parent HCDR3 with one or more of the following mutations:
Kabat residue Ala 96 replaced by Glu;
Kabat residue Asp 97 replaced by Glu or Asn;
Kabat residue Asp 98 replaced by Gly, Glu or His;
Kabat residue His 99 replaced by Gly or Thr;
Kabat residue Tyr 100 replaced by Pro, Asn, Arg, Trp or Ala;
Kabat residue Tyr 100A replaced by Ala, Arg, Thr, Gly, Asn, Pro or Ser;
Kabat residue 100B replaced by His, Trp, Gln, Pro or Thr;
Kabat residue Ile 100C replaced by Ala, Val, His, Tyr or Leu;
Ile inserted at Kabat residue 100D;
Kabat residue Val 102 is replaced by Leu, His, Met or Ile.

Thus, a binding member or a VH domain of the invention may comprise an HCDR3 wherein Kabat residue 100D is Ile or wherein Kabat residue 100D is absent.

A binding member or a VL domain of the invention may comprise the parent LCDR1 in which Kabat residue Ala 34 is replaced by Thr.

A binding member of a VL domain of the invention may comprise the parent LCDR3 with one or more of the following mutations:
Kabat residue Gln 89 replaced by Met or Ala;
Kabat residue Gln 90 replaced by Asn, Ser or Ala;
Kabat residue Ser 91 replaced by Asn, Gly, Ala or His;
Kabat residue Tyr 92 replaced by Trp, Ser, Lys or Phe;
Kabat residue Ser 93 replaced by Leu, Lys, Arg or Ala;
Kabat residue Thr 94 replaced by Ala, Gly or Pro;
Kabat residue Pro 95 deleted;
Kabat residue Trp 96 replaced by Gly;
Kabat residue Thr 97 replaced by Ser.

Thus, a binding member or a VL domain of the invention may comprise an LCDR3 in which Kabat residue 95 is Pro or wherein Kabat residue 95 is absent.

The invention provides an isolated binding member for human IL-6 comprising a set of CDRs: HCDR1, HCDR2, HCDR3, LCDR1, LCDR2 and LCDR3, wherein the set of CDRs has 22 or fewer amino acid alterations, e.g. up to 21, 20, 19, 18, 17, 16, 15, 14, 13, 12, 11, 10, 9, 8, 7, 6, 5, 4, 3, 2, 1 alterations or no alterations, from a set of CDRs in which:
HCDR1 has amino acid sequence SEQ ID NO: 3;
HCDR2 has amino acid sequence SEQ ID NO: 4;
HCDR3 has amino acid sequence SEQ ID NO: 115;
LCDR1 has amino acid sequence SEQ ID NO: 8;
LCDR2 has amino acid sequence SEQ ID NO: 9; and
LCDR3 has amino acid sequence SEQ ID NO: 120.

An amino acid alteration may be a substitution, insertion or deletion. Examples of Kabat positions that may be substituted, and examples of residue substitutions are discussed below, and Table 7 illustrates some of the substitutions.

As shown in Table 7, the length of HCDR3 and LCDR3 varied between different optimised antibodies described herein. Relative to the parent CDRs of CAN022D10, an insertion between Kabat residues 100 to 102 (shown in Table 7 at Kabat residue 100D) was observed in some antibodies, and a deletion between Kabat residues 92 to 97 was observed in other antibodies. The deletion at Kabat residue 95 was not observed in combination with the insertion. Thus, it may be advantageous for the longer, 12 residue HCDR3 sequences to be combined with the longer, 9 residue LCDR3 sequences, and it may be advantageous for the shorter, 11 residue HCDR3 sequences to be combined with the shorter, 8 residue LCDR3 sequences.

According to the Kabat numbering system, residues of LCDR3 are numbered from 89 to 97. LCDR3 sequences shorter than 9 residues are not envisaged by the Kabat numbering system. In the present invention, binding members may have an LCDR3 shorter than 9 residues, e.g. LCDR3 may be 8 residues long, as shown in Table 7. We number the 8 residues of LCDR3 89, 90, 91, 92, 93, 94, 96 and 97, respectively. In Table 7, deletion is thus shown at Kabat residue 95. However, it will be appreciated that the effect of the deletion is to reduce the length of the LCDR3 sequence, and that in principle the deletion could be considered to be made at any of residues 89 to 97, e.g. any of residues 92 to 97.

In HCDR3, the Kabat numbering system accommodates variability in CDR length by extension of the numbering system between Kabat residues 100 and 101, e.g. including residue 100A for an HCDR3 of 9 residues, plus 100B for an HCDR3 of 10 residues, plus 100C for an HCDR3 of 11 residues, plus 100D for an HCDR3 of 12 residues, as appropriate. In Table 7, the insertion of an additional amino acid in HCDR3 of some of the optimised clones relative to the parent HCDR3 is shown at Kabat residue 100D. However, it will be appreciated that in principle this insertion may be considered to be made at any of Kabat residues 100 to 102.

As demonstrated herein, one or more insertions or deletions may be present in one or more CDRs of a binding member, e.g. an HCDR3 and/or LCDR3. For example, a binding member of the invention may comprise a set of CDRs of any of Antibodies 2, 3, 4, 5, 7, 8, 10, 14, 16, 17, 18, 19, 21, 22 and 23, or a variant thereof as described herein, wherein each CDR optionally has an insertion to increase the length of the CDR by one residue or has a deletion of one residue to decrease the length of the CDR by one residue. Insertions and/or deletions may be made in HCDRs and/or an LCDRs, e.g. in an HCDR3 and/or in an LCDR3.

For example, a binding member may for example comprise a set of CDRs having 20 or fewer amino acid substitutions in a set of CDRs wherein:
HCDR1 has amino acid sequence SEQ ID NO: 3;
HCDR2 has amino acid sequence SEQ ID NO: 4;
HCDR3 has amino acid sequence SEQ ID NO: 115;
LCDR1 has amino acid sequence SEQ ID NO: 8;
LCDR2 has amino acid sequence SEQ ID NO: 9; and
LCDR3 has amino acid sequence SEQ ID NO: 120;
wherein the binding member optionally has an insertion of one residue to increase the length of the HCDR3 or a deletion of one residue to decrease the length of the HCDR3, and/or
has an insertion of one residue to increase the length of the LCDR3 or a deletion of one residue to decrease the length of the LCDR3.

A binding member of the invention may have an insertion of one residue in HCDR3 SEQ ID NO: 115 and/or an insertion of one residue in LCDR3 SEQ ID NO: 120.

Insertions or deletions may be made at any point in the CDRs. For example, in HCDR3 insertions or deletions may be of any of Kabat residues 95-102, e.g. any of Kabat residues 100-102. For example, in LCDR3 insertions or deletions may be of any of Kabat residues 89 to 97, e.g. any of Kabat residues 92 to 97.

A binding member or VH domain of the invention may comprise an HCDR1 in which Kabat residue 35 is Ile, Thr or Val.

A binding member or VH domain of the invention may comprise an HCDR2 in which Kabat residue 64 is Lys or Arg.

A binding member or VH domain of the invention may comprise an HCDR3 in which Kabat residue 95 is Trp and/or Kabat residue 101 is Asp.

A binding member or VH domain of the invention may comprise an HCDR3 wherein:
Kabat residue 96 is Ala or Glu;
Kabat residue 97 is Asp, Glu or Asn;
Kabat residue 98 is Asp, Gly, Glu or His;
Kabat residue 99 is His, Gly or Thr;
Kabat residue 100 is Pro, Tyr, Asn, Arg, Trp or Ala;
Kabat residue 100A is Pro, Tyr, Ala, Arg, Thr, Gly, Asn, Pro or Ser;
Kabat residue 100B is Trp, Tyr, His, Gln, Pro or Thr;
Kabat residue 100C is Ile, Ala, Val, His, Tyr or Leu; and
Kabat residue 102 is Leu, Val, His, Met or Ile.

A binding member or VL domain of the invention may comprise an LCDR1 in which Kabat residue 34 is Ala or Thr.

A binding member or VL domain of the invention may comprise an LCDR3 wherein:
Kabat residue 89 is Gln, Met or Ala;
Kabat residue 90 is Gln, Asn, Ser or Ala;
Kabat residue 91 is Ser, Asn, Gly, Ala or His;
Kabat residue 92 is Trp, Tyr, Ser, Lys or Phe;
Kabat residue 93 is Leu, Ser, Lys, Arg or Ala;
Kabat residue 94 is Gly, Thr, Ala or Pro;
Kabat residue 96 is Gly or Trp; and
Kabat residue 97 is Ser or Thr.

The invention provides binding members comprising an HCDR1, HCDR2 and/or HCDR3 of the parent or any of antibodies 2, 3, 4, 5, 7, 8, 10, 14, 16, 17, 18, 19, 21, 22 and 23, and/or an LCDR1, LCDR2 and/or LCDR3 of the parent or any of antibodies 2, 3, 4, 5, 7, 8, 10, 14, 16, 17, 18, 19, 21, 22 and 23 e.g. a set of CDRs of the parent or any of antibodies 2, 3, 4, 5, 7, 8, 10, 14, 16, 17, 18, 19, 21, 22 and 23 shown in Table 7.

For example, a binding member of the invention may comprise a set of CDRs: HCDR1, HCDR2, HCDR3, LCDR1, LCDR2 and LCDR3, wherein: HCDR1 is SEQ ID NO: 113; HCDR2 is SEQ ID NO: 114; HCDR3 is SEQ ID NO: 115; LCDR1 is SEQ ID NO: 118; LCDR2 is SEQ ID NO: 119; and LCDR3 is SEQ ID NO: 120, representing the CDRs of Antibody 18.

The binding member may comprise a set of VH CDRs of one of these antibodies. Optionally it may also comprise a set of VL CDRs of one of these antibodies, and the VL CDRs may be from the same or a different antibody as the VH CDRs.

A VH domain comprising a set of HCDRs of the parent or any of antibodies 2, 3, 4, 5, 7, 8, 10, 14, 16, 17, 18, 19, 21, 22 and 23, and/or a VL domain comprising a set of LCDRs of the parent or any of antibodies 2, 3, 4, 5, 7, 8, 10, 14, 16, 17, 18, 19, 21, 22 and 23 are also provided by the invention.

Typically, a VH domain is paired with a VL domain to provide an antibody antigen-binding site, although as discussed further below a VH or VL domain alone may be used to bind antigen. The antibody 2 VH domain may be paired with the antibody 2 VL domain, so that an antibody antigen-binding site is formed comprising both the antibody 2 VH and VL domains. Analogous embodiments are provided for the other VH and VL domains disclosed herein. In other embodiments, the antibody 2 VH is paired with a VL domain other than the antibody VL. Light-chain promiscuity is well established in the art. Again, analogous embodiments are provided by the invention for the other VH and VL domains disclosed herein.

Thus, the VH of the parent or of any of antibodies 2, 3, 4, 5, 7, 8, 10, 14, 16, 17, 18, 19, 21, 22 and 23 may be paired with the VL of the parent or of any of antibodies 2, 3, 4, 5, 7, 8, 10, 14, 16, 17, 18, 19, 21, 22 and 23.

A binding member may comprise an antibody molecule having one or more CDRs, e.g. a set of CDRs, within an antibody framework. For example, one or more CDRs or a set of CDRs of an antibody may be grafted into a framework (e.g. human framework) to provide an antibody molecule. The framework regions may be of human germline gene segment sequences. Thus, the framework may be germlined, whereby one or more residues within the framework are changed to match the residues at the equivalent position in the most similar human germline framework. The skilled person can select a germline segment that is closest in sequence to the framework sequence of the antibody before germlining and test the affinity or activity of the antibodies to confirm that germlining does not significantly reduce antigen binding or potency in assays described herein. Human germline gene segment sequences are known to those skilled in the art and can be accessed for example from the VBase compilation.

A binding member of the invention may be an isolated human antibody molecule having a VH domain comprising a set of HCDRs in a human germline framework, e.g. Vh3_DP-86_(3-66). Thus, the VH domain framework regions FR1, FR2 and/or FR3 may comprise framework regions of human germline gene segment Vh3_DP-86_(3-66) and/or may be germlined by mutating framework residues to match the framework residues of this human germline gene segment. FR4 may comprise a framework region of human germline j segment JH2. The amino acid sequence of VH FR1 may be SEQ ID NO: 167. The amino acid sequence of VH FR2 may be SEQ ID NO: 168. The amino acid sequence of VH FR3 may be SEQ ID NO: 169. The amino acid sequence of VH FR4 may be SEQ ID NO: 170.

Normally the binding member also has a VL domain comprising a set of LCDRs, e.g. in a human germline framework, e.g. Vk1_L12. Thus, the VL domain framework regions may comprise framework regions FR1, FR2 and/or FR3 of human germline gene segment Vk1_L12 and/or may be germlined by mutating framework residues to match the framework residues of this human germline gene segment. FR4 may comprise a framework region of human germline j segment JK2. The amino acid sequence of VL FR1 may be SEQ ID NO: 171. The amino acid sequence of VL FR2 may be SEQ ID NO: 172. The amino acid sequence of VL FR3 may be SEQ ID NO: 173. The amino acid sequence of VL FR4 may be SEQ ID NO: 174.

A germlined VL domain may or may not be germlined at the Vernier residue or residues, but is normally not.

An antibody molecule or a VH domain of the invention may comprise the following set of heavy chain framework regions:
FR1 SEQ ID NO: 167;
FR2 SEQ ID NO: 168;
FR3 SEQ ID NO: 169;
FR4 SEQ ID NO: 170;
or may comprise the said set of heavy chain framework regions with one, two, three, four or five amino acid alterations, e.g. substitutions.

An antibody molecule or a VL domain of the invention may comprise the following set of light chain framework regions:
FR1 SEQ ID NO: 171;
FR2 SEQ ID NO: 172;
FR3 SEQ ID NO: 173;
FR4 SEQ ID NO: 174;
or may comprise the said set of light chain framework regions with one, two, three, four or five amino acid alterations, e.g. substitutions.

An amino acid alteration may be a substitution, an insertion or a deletion.

For example, an antibody molecule of the invention may comprise a set of heavy and light chain framework regions, wherein
heavy chain FR1 is SEQ ID NO: 167;
heavy chain FR2 is SEQ ID NO: 168;
heavy chain FR3 is SEQ ID NO: 169;
heavy chain FR4 is SEQ ID NO: 170;
light chain FR1 is SEQ ID NO: 171;
light chain FR2 is SEQ ID NO: 172;
light chain FR3 is SEQ ID NO: 173;
light chain FR4 is SEQ ID NO: 174;
or may comprise the said set of heavy and light chain framework regions with 10 or fewer, e.g. five or fewer, amino acid alterations, e.g. substitutions. For example there may be one or two amino acid substitutions in the said set of heavy and light chain framework regions.

A non-germlined antibody molecule has the same CDRs, but different frameworks, compared with a germlined antibody molecule. Of the antibody sequences shown herein in the appended sequence listing, sequences of antibody nos 7, 10, 17 and 18 are germlined. Germlined antibodies 2 to 5, 8, 14, 16, 19 and 21 to 23 may be produced by germlining framework regions of the VH and VL domain sequences shown herein for these antibodies.

The 3' cgt codon, and corresponding Arginine residue, shown in the nucleotide and amino acid sequences for the kappa VL domains of Antibodies 2, 3, 4, 5, 7, 8, 10, 14, 16, 17, 18, 19, 21, 22 and 23 respectively were included in the expressed scFv and IgG sequences of these antibodies. The C terminal Arginine residue of the sequences corresponds to Kabat residue 108. The origin of this residue and its encoding triplet cgt is explained below.

To express the light chain of the IgG, a nucleotide sequence encoding the antibody light chain was provided, comprising a first exon encoding the VL domain, a second exon encoding the CL domain, and an intron separating the first exon and the second exon. Under normal circumstances, the intron is spliced out by cellular mRNA processing machinery, joining the 3' end of the first exon to the 5' end of the second exon. Thus, when DNA having the said nucleotide sequence was expressed as RNA, the first and second exons were spliced together. Translation of the spliced RNA produces a polypeptide comprising the VL domain and CL domain.

The choice of constant domain is significant in that for kappa light chains the bridging amino acid is arginine, formed by the cga codon, where the first cytosine is encoded in exon 1 and the guanine and adenine are encoded in exon 2.

After splicing, for Antibodies 2, 3, 4, 5, 7, 8, 10, 14, 16, 17, 18, 19, 21, 22 and 23, the Arg at Kabat residue 108 is encoded by the last base (c) of the VL domain framework 4 sequence and the first two bases (gt) of the CL domain.

The Arginine residue at Kabat residue 108 may be considered to be the C terminal residue of the VL domain of the antibody molecule.

A binding member of the invention may be one which competes for binding to IL-6 with any binding member that (i) binds IL-6 and (ii) comprises a binding member, VH and/or VL domain, CDR e.g. HCDR3, and/or set of CDRs disclosed herein.

Competition between binding members may be assayed easily in vitro, for example using ELISA and/or by tagging a specific reporter molecule to one binding member which can be detected in the presence of one or more other untagged binding members, to enable identification of binding members which bind the same epitope or an overlapping epitope. Such methods are readily known to one of ordinary skill in the art, and are described in more detail herein (see the Detailed Description, and the epitope competition assays in the Materials and Methods section of the Examples.) Thus, a further aspect of the present invention provides a binding member comprising a human antibody antigen-binding site that competes with an antibody molecule, for example an antibody molecule comprising a VH and/or VL domain, CDR e.g. HCDR3 or set of CDRs of the parent antibody or any of antibodies 2, 3, 4, 5, 7, 8, 10, 14, 16, 17, 18, 19, 21, 22 and 23, for binding to IL-6.

In further aspects, the invention provides an isolated nucleic acid which comprises a sequence encoding a binding member, VH domain and/or VL domain according to the present invention, and methods of preparing a binding member, a VH domain and/or a VL domain of the invention, which comprise expressing said nucleic acid under conditions to bring about production of said binding member, VH domain and/or VL domain, and recovering it.

Another aspect of the present invention provides nucleic acid, generally isolated, encoding a VH CDR or VL CDR sequence disclosed herein.

A further aspect provides a host cell containing or transformed with nucleic acid of the invention.

Further aspects of the present invention provide for compositions containing binding members of the invention, and their use in methods of binding, inhibiting and/or neutralising IL-6, including methods of treatment of the human or animal body by therapy.

Binding members according to the invention may be used in a method of treatment or diagnosis, such as a method of treatment (which may include prophylactic treatment) of a disease or disorder in the human or animal body (e.g. in a human patient), which comprises administering to said patient an effective amount of a binding member of the invention. Conditions treatable in accordance with the present invention include any in which IL-6 plays a role, as discussed in detail elsewhere herein.

These and other aspects of the invention are described in further detail below.

TERMINOLOGY

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

IL-6 and IL-6 Receptor

IL-6 is interleukin 6. IL-6 may also be referred to herein as "the antigen".

The full length amino acid sequence of human IL-6 is SEQ ID NO: 161. This sequence is cleaved in vivo to remove an N-terminal leader peptide, to produce mature IL-6. Mature human IL-6 has amino acid sequence SEQ ID NO: 165. The mature sequence represents the in vivo circulating IL-6, which is the target antigen for therapeutic and in vivo diagnostic applications as described herein. Accordingly, IL-6 referred to herein is normally mature human IL-6, unless otherwise indicated by context.

IL-6 may be conjugated to a detectable label, such as HIS FLAG, e.g. for use in assays as described herein. For example, a fusion protein comprising IL-6 conjugated to a HIS FLAG sequence may be used. A sequence of HIS FLAG tagged human IL-6 is SEQ ID NO: 162.

IL-6 receptor a, IL-6Ra, is the receptor for interleukin 6. IL-6Ra is also known as IL-6Rα, IL-6Ra, IL-6R and CD126. IL-6Ra exists in vivo in a transmembrane form and in a soluble form. References to IL-6Ra may be transmembrane IL-6Ra and/or soluble IL-6Ra unless otherwise indicated by context.

IL-6 receptor referred to herein is normally human IL-6 receptor, unless otherwise indicated. An amino acid sequence of human soluble IL-6Ra (sIL-6Ra, sIL-6R) is SEQ ID NO: 163. An amino acid sequence of human transmembrane IL-6Ra is SEQ ID NO: 164.

IL-6 binds IL-6Ra to form a complex, IL-6:IL-6Ra. The complex may be either soluble (with sIL-6Ra) or membrane bound (with transmembrane IL-6Ra). When the IL-6Ra is the soluble form, the complex is designated IL-6:sIL-6Ra. References to IL-6:IL-6Ra may include IL-6 complexed with transmembrane IL-6Ra or with soluble IL-6Ra, unless otherwise indicated by context.

gp130 gp130 is a receptor for the IL-6:IL-6Ra complex. Cloning and characterisation of gp130 is reported in Hibi et al, Cell 63:1149-1157 (1990). A sequence of human gp130 is set out in SEQ ID NO: 166.

Binding Member

This describes one member of a pair of molecules that bind one another. The members of a binding pair may be naturally derived or wholly or partially synthetically produced. One member of the pair of molecules has an area on its surface, or a cavity, which binds to and is therefore complementary to a particular spatial and polar organization of the other member of the pair of molecules. Examples of types of binding pairs are antigen-antibody, biotin-avidin, hormone-hormone receptor, receptor-ligand, enzyme-substrate. The present invention is concerned with antigen-antibody type reactions.

A binding member normally comprises a molecule having an antigen-binding site. For example, a binding member may be an antibody molecule or a non-antibody protein that comprises an antigen-binding site.

An antigen binding site may be provided by means of arrangement of CDRs on non-antibody protein scaffolds, such as fibronectin or cytochrome B etc. [42, 43, 44], or by randomising or mutating amino acid residues of a loop within a protein scaffold to confer binding specificity for a desired target. Scaffolds for engineering novel binding sites in proteins have been reviewed in detail by Nygren et al. [44]. Protein scaffolds for antibody mimics are disclosed in WO/0034784, which is herein incorporated by reference in its entirety, in which the inventors describe proteins (antibody mimics) that include a fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties, such as an ability to enter cells, penetrate deep into tissues or reach targets within other structures, or to bind within protein cavities of the target antigen. Use of antigen binding sites in non-antibody protein scaffolds is reviewed in Wess, 2004 [45]. Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from S. aureus, transferrin, tetranectin, fibronectin (e.g. 10th fibronectin type III domain), lipocalins as well as gamma-crystalline and other Affilin™ scaffolds (Scil Proteins). Examples of other approaches include synthetic "Microbodies" based on cyclotides—small proteins having intra-molecular disulphide bonds, Microproteins (Versabodies™, Amunix) and ankyrin repeat proteins (DARPins, Molecular Partners).

In addition to antibody sequences and/or an antigen-binding site, a binding member according to the present invention may comprise other amino acids, e.g. forming a peptide or polypeptide, such as a folded domain, or to impart to the molecule another functional characteristic in addition to ability to bind antigen. Binding members of the invention may carry a detectable label, or may be conjugated to a toxin or a targeting moiety or enzyme (e.g. via a peptidyl bond or linker). For example, a binding member may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

Although, as noted, CDRs can be carried by non-antibody scaffolds, the structure for carrying a CDR or a set of CDRs of the invention will generally be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat, et al., 1987 [46], and updates thereof. A number of academic and commercial on-line resources are available to query this database. For example, see ref. [47] and the associated on-line resource, currently at the web address of http://www.bioinf.org.uk/abs/simkab.html.

By CDR region or CDR, it is intended to indicate the hypervariable regions of the heavy and light chains of the immunoglobulin as defined by Kabat et al. 1991 [48], and later editions. An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has a greater size variability (greater diversity essentially due to the mechanisms of arrangement of the genes which give rise to it). It may be as short as 2 amino acids although the longest size known is 26. CDR length may also vary according to the length that can be accommodated by the particular underlying framework. Functionally, HCDR3 plays a role in part in the determination of the specificity of the antibody [refs. 49, 50, 51, 52, 53, 54, 55, 56].

HCDR1 may be 5 amino acids long, consisting of Kabat residues 31-35.

HCDR2 may be 17 amino acids long, consisting of Kabat residues 50-65.

HCDR3 may be 11 or 12 amino acids long, consisting of Kabat residues 95-102, optionally including Kabat residue 100D.

LCDR1 may be 11 amino acids long, consisting of Kabat residues 24-34.

LCDR2 may be 7 amino acids long, consisting of Kabat residues 50-56.

LCDR3 may be 8 or 9 amino acids long, consisting of Kabat residues 89-97, optionally including Kabat residue 95.

Antibody Molecule

This describes an immunoglobulin whether natural or partly or wholly synthetically produced. The term also covers any polypeptide or protein comprising an antibody antigen-binding site. It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described later. Antibody fragments that comprise an antibody antigen-binding site include, but are not limited to, molecules such as Fab, Fab', Fab'-SH, scFv, Fv, dAb and Fd. Various other antibody molecules including one or more antibody antigen-binding sites have been engineered, including for example Fab2, Fab3, diabodies, triabodies, tetrabodies and minibodies. Antibody molecules and methods for their construction and use are described in [57].

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the binding specificity of antibodies produced.

As antibodies can be modified in a number of ways, the term "antibody molecule" should be construed as covering any binding member or substance having an antibody antigen-binding site with the required specificity and/or binding to antigen. Thus, this term covers antibody fragments and derivatives, including any polypeptide comprising an antibody antigen-binding site, whether natural or wholly or partially synthetic. Chimeric molecules comprising an antibody antigen-binding site, or equivalent, fused to another polypeptide (e.g. derived from another species or belonging to another antibody class or subclass) are therefore included. Cloning and expression of chimeric antibodies are described in EP-A-0120694 and EP-A-0125023, and a large body of subsequent literature.

Further techniques available in the art of antibody engineering have made it possible to isolate human and human-ised antibodies. For example, human hybridomas can be made as described by Kontermann & Dubel [58]. Phage display, another established technique for generating binding members has been described in detail in many publications, such as Kontermann & Dubel [58] and WO92/01047 (discussed further below), and U.S. Pat. No. 5,969,108, U.S. Pat. No. 5,565,332, U.S. Pat. No. 5,733,743, U.S. Pat. No. 5,858,657, U.S. Pat. No. 5,871,907, U.S. Pat. No. 5,872,215, U.S. Pat. No. 5,885,793, U.S. Pat. No. 5,962,255, U.S. Pat. No. 6,140,471, U.S. Pat. No. 6,172,197, U.S. Pat. No. 6,225,447, U.S. Pat. No. 6,291,650, U.S. Pat. No. 6,492,160, U.S. Pat. No. 6,521,404.

Transgenic mice in which the mouse antibody genes are inactivated and functionally replaced with human antibody genes while leaving intact other components of the mouse immune system, can be used for isolating human antibodies [59]. Humanised antibodies can be produced using techniques known in the art such as those disclosed in for example WO91/09967, U.S. Pat. No. 5,585,089, E9592106, U.S. Pat. No. 565,332 and WO93/17105. Further, WO2004/006955 describes methods for humanising antibodies, based on selecting variable region framework sequences from human antibody genes by comparing canonical CDR structure types for CDR sequences of the variable region of a non-human antibody to canonical CDR structure types for corresponding CDRs from a library of human antibody sequences, e.g. germline antibody gene segments. Human antibody variable regions having similar canonical CDR structure types to the non-human CDRs from a subset of member human antibody sequences from which to select human framework sequences. The subset members may be further ranked by amino acid similarity between the human and the non-human CDR sequences. In the method of WO2004/006955, top ranking human sequences are selected to provide the framework sequences for constructing a chimeric antibody that functionally replaces human CDR sequences with the non-human CDR counterparts using the selected subset member human frameworks, thereby providing a humanized antibody of high affinity and low immunogenicity without need for comparing framework sequences between the non-human and human antibodies. Chimeric antibodies made according to the method are also disclosed.

Synthetic antibody molecules may be created by expression from genes generated by means of oligonucleotides synthesized and assembled within suitable expression vectors, for example as described by Knappik et al. [60] or Krebs et al. [61].

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment [62, 63, 64], which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site [65, 66]; (viii) bispecific single chain Fv dimers (PCT/US92/09965) and (ix) "diabodies", multivalent or multispecific fragments constructed by gene fusion (WO94/13804; [67]). Fv, scFv or diabody molecules may be stabilized by the incorporation of disulphide bridges linking the VH and VL domains [68]. Minibodies comprising a scFv joined to a CH3 domain may also be made [69]. Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

Qui et al. [70] described antibody molecules containing just two CDRs linked by a framework region. CDR3 from the VH or VL domain was linked to the CDR1 or CDR2 loop of the other domain. Linkage was through the C terminus of the selected CDR1 or CDR2 to the N terminus of the CDR3, via a FR region. Qui et al. selected the FR region having the fewest hydrophobic patches. The best combination for the antibody tested was found to be VL CDR1 linked by VH FR2 to VH CDR3 (VHCDR1-VHFR2-VLCDR3). At a molecular weight of around 3 kDa, these antibody molecules offer advantages in terms of improved tissue penetration as compared with full immunoglobulins (approx. 150 kDa) or scFv (approx. 28 kDa).

Antibody fragments of the invention can be obtained starting from a parent antibody molecule or any of the antibody molecules 2, 3, 4, 5, 7, 8, 10, 14, 16, 17, 18, 19, 21, 22 and 23, by methods such as digestion by enzymes e.g. pepsin or papain and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers, such as those supplied by the company Applied Biosystems, etc., or by nucleic acid synthesis and expression.

Functional antibody fragments according to the present invention include any functional fragment whose half-life is increased by a chemical modification, especially by PEGylation, or by incorporation in a liposome.

A dAb (domain antibody) is a small monomeric antigen-binding fragment of an antibody, namely the variable region of an antibody heavy or light chain [64]. VH dAbs occur naturally in camelids (e.g. camel, llama) and may be produced by immunizing a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. Camelid VH dAbs are being developed for therapeutic use under the name "NANOBODIES™". A binding member of the present invention may be a dAb comprising a VH or VL domain substantially as set out herein, or a VH or VL domain comprising a set of CDRs substantially as set out herein.

Bispecific or bifunctional antibodies form a second generation of monoclonal antibodies in which two different variable regions are combined in the same molecule [71]. Their use has been demonstrated both in the diagnostic field and in the therapy field from their capacity to recruit new effector functions or to target several molecules on the surface of tumour cells. Where bispecific antibodies are to be used, these may be conventional bispecific antibodies, which can be manufactured in a variety of ways [72], e.g. prepared chemically or from hybrid hybridomas, or may be any of the bispecific antibody fragments mentioned above. These antibodies can be obtained by chemical methods [73, 74] or somatic methods [75, 76] but likewise and preferentially by genetic engineering techniques which allow the heterodimerization to be forced and thus facilitate the process of purification of the antibody sought [77]. Examples of bispecific antibodies include those of the BiTE™ technology in which the binding domains of two antibodies with different specificity can be used and directly linked via short flexible peptides. This combines two antibodies on a short single polypeptide chain.

Diabodies and scFv can be constructed without an Fc region, using only variable domains, potentially reducing the effects of anti-idiotypic reaction.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies. Bispecific diabodies, as opposed to bispecific whole antibodies, may also be particularly useful because they can be readily constructed and expressed in E. coli. Diabodies (and many other polypeptides, such as antibody fragments) of appropriate binding specificities can be readily selected using phage display (WO94/13804) from libraries. If one arm of the diabody is to be kept constant, for instance, with a specificity directed against IL-6, then a library can be made where the other arm is varied and an antibody of appropriate specificity selected. Bispecific whole antibodies may be made by alternative engineering methods as described in Ridgeway et al., 1996 [78].

Various methods are available in the art for obtaining antibodies against IL-6. The antibodies may be monoclonal antibodies, especially of human, murine, chimeric or humanized origin, which can be obtained according to the standard methods well known to the person skilled in the art.

In general, for the preparation of monoclonal antibodies or their functional fragments, especially of murine origin, it is possible to refer to techniques which are described in particular in the manual "Antibodies" [79] or to the technique of preparation from hybridomas described by Köhler and Milstein [80].

Monoclonal antibodies can be obtained, for example, from the B cells of an animal immunized against IL-6, or one of its fragments containing the epitope recognized by said monoclonal antibodies. Suitable fragments and peptides or polypeptides comprising them are described herein, and may be used to immunise animals to generate antibodies against IL-6. Said IL-6, or one of its fragments, can especially be produced according to the usual working methods, by genetic recombination starting with a nucleic acid sequence contained in the cDNA sequence coding for IL-6 or fragment thereof, by peptide synthesis starting from a sequence of amino acids comprised in the peptide sequence of the IL-6 and/or fragment thereof.

The monoclonal antibodies can, for example, be purified on an affinity column on which IL-6 or one of its fragments containing the epitope recognized by said monoclonal antibodies, has previously been immobilized. More particularly, the monoclonal antibodies can be purified by chromatography on protein A and/or G, followed or not followed by ion-exchange chromatography aimed at eliminating the residual protein contaminants as well as the DNA and the LPS, in itself, followed or not followed by exclusion chromatography on Sepharose gel in order to eliminate the potential aggregates due to the presence of dimers or of other multimers. In one embodiment, the whole of these techniques can be used simultaneously or successively.

Antigen-Binding Site

This describes the part of a molecule that binds to and is complementary to all or part of the target antigen. In an antibody molecule it is referred to as the antibody antigen-binding site, and comprises the part of the antibody that binds to and is complementary to all or part of the target antigen. Where an antigen is large, an antibody may only bind to a particular part of the antigen, which part is termed an epitope. An antibody antigen-binding site may be provided by one or more antibody variable domains. An antibody antigen-binding site may comprise an antibody light chain variable region (VL) and an antibody heavy chain variable region (VH).

WO2006/072620 describes engineering of antigen binding sites in structural (non-CDR) loops extending between beta strands of immunoglobulin domains. An antigen binding site may be engineered in a region of an antibody molecule separate from the natural location of the CDRs, e.g. in a framework region of a VH or VL domain, or in an antibody constant domain e.g. CH1 and/or CH3. An antigen binding site engineered in a structural region may be additional to, or instead of, an antigen binding site formed by sets of CDRs of a VH and VL domain. Where multiple antigen binding sites are present in an antibody molecule, they may bind the same antigen (IL-6), thereby increasing valency of the binding member. Alternatively, multiple antigen binding sites may bind different antigens (IL-6 and one or more another antigen), and this may be used to add effector functions, prolong half-life or improve in vivo delivery of the antibody molecule.

Isolated

This refers to the state in which binding members of the invention, or nucleic acid encoding such binding members, will generally be in accordance with the present invention. Thus, binding members, VH and/or VL domains, and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes of origin other than the sequence encoding a polypeptide with the required function. Isolated members and isolated nucleic acid will be free or substantially free of material with which they are naturally associated, such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Binding members may be glycosylated, either naturally or by systems of heterologous eukaryotic cells (e.g. CHO or NS0 (ECACC 85110503) cells, or they may be (for example if produced by expression in a prokaryotic cell) unglycosylated.

Heterogeneous preparations comprising anti-IL-6 antibody molecules also form part of the invention. For example, such preparations may be mixtures of antibodies with full-length heavy chains and heavy chains lacking the C-terminal lysine, with various degrees of glycosylation and/or with derivatized amino acids, such as cyclisation of an N-terminal glutamic acid to form a pyroglutamic acid residue.

As used herein, the phrase "substantially as set out" refers to the characteristic(s) of the relevant CDRs of the VH or VL domain of binding members described herein will be either identical or highly similar to the specified regions of which the sequence is set out herein. As described herein, the phrase "highly similar" with respect to specified region(s) of one or more variable domains, it is contemplated that from 1 to about 5, e.g. from 1 to 4, including 1 to 3, or 1 or 2, or 3 or 4, amino acid substitutions may be made in the CDR and/or VH or VL domain.

BRIEF DESCRIPTION OF THE FIGURE

FIG. 1. This figure shows the effect of administration of an anti-IL-6 antibody (Antibody 18) on human recombinant IL-6 induced haptoglobin increase in the mouse in vivo.

DETAILED DESCRIPTION OF THE INVENTION

As noted above, a binding member in accordance with the present invention modulates and may neutralise a biological activity of IL-6. As described herein, IL-6-binding members of the present invention may be optimised for neutralizing potency. Generally, potency optimisation involves mutating the sequence of a selected binding member (normally the variable domain sequence of an antibody) to generate a library of binding members, which are then assayed for potency and the more potent binding members are selected. Thus selected "potency-optimised" binding members tend to have a higher potency than the binding member from which the library was generated. Nevertheless, high potency binding members may also be obtained without optimisation, for example a high potency binding member may be obtained directly from an initial screen e.g. a biochemical neutralization assay. A "potency optimized" binding member refers to a binding member with an optimized potency of neutralization of a particular activity or downstream function of IL-6. Assays and potencies are described in more detail elsewhere herein. The present invention provides both potency-optimized and non-optimized binding members, as well as methods for potency optimization from a selected binding member. The present invention thus allows the skilled person to generate binding members having high potency.

In a further aspect, the present invention provides a method of obtaining one or more binding members able to bind the antigen, the method including bringing into contact a library of binding members according to the invention and said antigen, and selecting one or more binding members of the library able to bind said antigen.

The library may be displayed on particles or molecular complexes, e.g. replicable genetic packages, such as yeast, bacterial or bacteriophage (e.g. T7) particles, viruses, cells or covalent, ribosomal or other in vitro display systems, each particle or molecular complex containing nucleic acid encoding the antibody VH variable domain displayed on it, and optionally also a displayed VL domain if present. Phage display is described in WO92/01047 and e.g. U.S. Pat. No. 5,969,108, U.S. Pat. No. 5,565,332, U.S. Pat. No. 5,733,743, U.S. Pat. No. 5,858,657, U.S. Pat. No. 5,871,907, U.S. Pat. No. 5,872,215, U.S. Pat. No. 5,885,793, U.S. Pat. No. 5,962,255, U.S. Pat. No. 6,140,471, U.S. Pat. No. 6,172,197, U.S. Pat. No. 6,225,447, U.S. Pat. No. 6,291,650, U.S. Pat. No. 6,492,160 and U.S. Pat. No. 6,521,404, each of which is herein incorporated by reference in their entirety.

Following selection of binding members able to bind the antigen and displayed on bacteriophage or other library particles or molecular complexes, nucleic acid may be taken from a bacteriophage or other particle or molecular complex displaying a said selected binding member. Such nucleic acid may be used in subsequent production of a binding member or an antibody VH or VL variable domain by expression from nucleic acid with the sequence of nucleic acid taken from a bacteriophage or other particle or molecular complex displaying a said selected binding member.

An antibody VH variable domain with the amino acid sequence of an antibody VH variable domain of a said selected binding member may be provided in isolated form, as may a binding member comprising such a VH domain.

Ability to bind IL-6 may be further tested, also ability to compete with e.g. a parent antibody molecule or an antibody molecule 2, 3, 4, 5, 7, 8, 10, 14, 16, 17, 18, 19, 21, 22 or 23 (e.g. in scFv format and/or IgG format, e.g. IgG1) for binding to IL-6. Ability to neutralize IL-6 may be tested, as discussed further elsewhere herein.

A binding member according to the present invention may bind IL-6 with the affinity of a parent or other antibody molecule, e.g. scFv, or one of antibodies 2, 3, 4, 5, 7, 8, 10, 14, 16, 17, 18, 19, 21, 22 and 23, e.g. IgG1, or with an affinity that is better.

A binding member according to the present invention may neutralise a biological activity of IL-6 with the potency of a parent or other antibody molecule, one of antibodies 2, 3, 4, 5, 7, 8, 10, 14, 16, 17, 18, 19, 21, 22 and 23 e.g. scFv, or IgG1, or with a potency that is better.

Binding affinity and neutralization potency of different binding members can be compared under appropriate conditions.

Variants of the VH and VL domains and CDRs of the present invention, including those for which amino acid sequences are set out herein, and which can be employed in binding members of the invention can be obtained by means of methods of sequence alteration or mutation and screening for antigen binding members with desired characteristics. Examples of desired characteristics include but are not limited to:

Increased binding affinity for antigen relative to known antibodies which are specific for the antigen Increased neutralization of an antigen activity relative to known antibodies which are specific for the antigen if the activity is known Specified competitive ability with a known antibody or ligand to the antigen at a specific molar ratio Ability to immunoprecipitate complex Ability to bind to a specified epitope
  Linear epitope, e.g. peptide sequence identified using peptide-binding scan as described herein, e.g. using peptides screened in linear and/or constrained conformation
  Conformational epitope, formed by non-continuous residues Ability to modulate a new biological activity of IL-6, or downstream molecule.

Such methods are also provided herein.

Variants of antibody molecules disclosed herein may be produced and used in the present invention. Following the lead of computational chemistry in applying multivariate data analysis techniques to the structure/property-activity relationships [81] quantitative activity-property relationships of antibodies can be derived using well-known mathematical techniques, such as statistical regression, pattern recognition and classification [82, 83, 84, 85, 86, 87]. The properties of antibodies can be derived from empirical and theoretical models (for example, analysis of likely contact residues or calculated physicochemical property) of antibody sequence, functional and three-dimensional structures and these properties can be considered singly and in combination.

An antibody antigen-binding site composed of a VH domain and a VL domain is typically formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites [88, 89]. These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions [88, 89].

This study of sequence-structure relationship can be used for prediction of those residues in an antibody of known sequence, but of an unknown three-dimensional structure, which are important in maintaining the three-dimensional structure of its CDR loops and hence maintain binding specificity. These predictions can be backed up by comparison of the predictions to the output from lead optimization experiments. In a structural approach, a model can be created of the antibody molecule [90] using any freely available or commercial package, such as WAM [91]. A protein visualisation and analysis software package, such as Insight II (Accelrys, Inc.) or Deep View [92] may then be used to evaluate possible substitutions at each position in the CDR. This information may then be used to make substitutions likely to have a minimal or beneficial effect on activity.

The techniques required to make substitutions within amino acid sequences of CDRs, antibody VH or VL domains and binding members generally are available in the art. Variant sequences may be made, with substitutions that may or may not be predicted to have a minimal or beneficial effect on activity, and tested for ability to bind and/or neutralize IL-6 and/or for any other desired property.

Variable domain amino acid sequence variants of any of the VH and VL domains whose sequences are specifically disclosed herein may be employed in accordance with the present invention, as discussed.

Variants of VL domains of the invention, and binding members or antibody molecules comprising them, include VL domains in which Arginine is not present at Kabat residue 108, e.g. where Kabat residue 108 is a different residue or is deleted. For example, an antibody molecule, such as an antibody molecule lacking a constant domain, e.g. an scFv, may comprise a VL domain having a VL domain sequence or variant thereof as described herein, in which Arginine at Kabat residue 108 an amino acid residue other than Arginine or is deleted.

A further aspect of the invention is an antibody molecule comprising a VH domain that has at least 60, 70, 80, 85, 90, 95, 98 or 99% amino acid sequence identity with a VH domain of any of antibodies 2, 3, 4, 5, 7, 8, 10, 14, 16, 17, 18, 19, 21, 22 and 23 shown in the appended sequence listing, and/or comprising a VL domain that has at least 60, 70, 80, 85, 90, 95, 98 or 99% amino acid sequence identity with a VL domain of any of antibodies 2, 3, 4, 5, 7, 8, 10, 14, 16, 17, 18, 19, 21, 22 and 23 shown in the appended sequence listing. Algorithms that can be used to calculate % identity of two amino acid sequences include e.g. BLAST [93], FASTA [94], or the Smith-Waterman algorithm [95], e.g. employing default parameters.

Particular variants may include one or more amino acid sequence alterations (addition, deletion, substitution and/or insertion of an amino acid residue).

Alterations may be made in one or more framework regions and/or one or more CDRs. The alterations normally do not result in loss of function, so a binding member comprising a thus-altered amino acid sequence may retain an ability to bind and/or neutralize IL-6. It may retain the same quantitative binding and/or neutralizing ability as a binding member in which the alteration is not made, e.g. as measured in an assay described herein. The binding member comprising a thus-altered amino acid sequence may have an improved ability to bind and/or neutralize IL-6. Alteration may comprise replacing one or more amino acid residue with a non-naturally occurring or non-standard amino acid, modifying one or more amino acid residue into a non-naturally occurring or non-standard form, or inserting one or more non-naturally occurring or non-standard amino acid into the sequence. Examples of numbers and locations of alterations in sequences of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring. Several naturally occurring non-standard amino acids are known in the art, such as 4-hydroxyproline, 5-hydroxylysine, 3-methylhistidine, N-acetylserine, etc. [96]. Those amino acid residues that are derivatised at their N-alpha position will only be located at the N-terminus of an amino-acid sequence. Normally in the present invention an amino acid is an L-amino acid, but it may be a D-amino acid. Alteration may therefore comprise modifying an L-amino acid into, or replacing it with, a D-amino acid. Methylated, acetylated and/or phosphorylated forms of amino acids are also known, and amino acids in the present invention may be subject to such modification.

Amino acid sequences in antibody domains and binding members of the invention may comprise non-natural or non-standard amino acids described above. Non-standard amino acids (e.g. D-amino acids) may be incorporated into an amino acid sequence during synthesis, or by modification or replacement of the "original" standard amino acids after synthesis of the amino acid sequence.

Use of non-standard and/or non-naturally occurring amino acids increases structural and functional diversity, and can thus increase the potential for achieving desired IL-6-binding and neutralizing properties in a binding member of the invention. Additionally, D-amino acids and analogues have been shown to have different pharmacokinetic profiles compared with standard L-amino acids, owing to in vivo degradation of polypeptides having L-amino acids after administration to an animal e.g. a human, meaning that D-amino acids are advantageous for some in vivo applications.

Novel VH or VL regions carrying CDR-derived sequences of the invention may be generated using random mutagenesis of one or more selected VH and/or VL genes to generate mutations within the entire variable domain. Such a technique is described by Gram et al. [97], who used error-prone PCR. In some embodiments one or two amino acid substitutions are made within an entire variable domain or set of CDRs.

Another method that may be used is to direct mutagenesis to CDR regions of VH or VL genes. Such techniques are disclosed by Barbas et al. [98] and Schier et al. [99].

All the above-described techniques are known as such in the art and the skilled person will be able to use such techniques to provide binding members of the invention using routine methodology in the art.

A further aspect of the invention provides a method for obtaining an antibody antigen-binding site for IL-6, the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify a binding member or an antibody antigen-binding site for IL-6 and optionally with one or more desired properties, e.g. ability to neutralize IL-6 activity. Said VL domain may have an amino acid sequence which is substantially as set out herein. An analogous method may be employed in which one or more sequence variants of a VL domain disclosed herein are combined with one or more VH domains. As noted above, a CDR amino acid sequence substantially as set out herein may be carried as a CDR in a human antibody variable domain or a substantial portion thereof. The HCDR3 sequences substantially as set out herein represent embodiments of the present invention and each of these may be carried as a HCDR3 in a human heavy chain variable domain or a substantial portion thereof.

Variable domains employed in the invention may be obtained or derived from any germline or rearranged human variable domain, or may be a synthetic variable domain based on consensus or actual sequences of known human variable domains. A variable domain can be derived from a non-human antibody. A CDR sequence of the invention (e.g. CDR3) may be introduced into a repertoire of variable domains lacking a CDR (e.g. CDR3), using recombinant DNA technology. For example, Marks et al. [100] describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide binding members of the invention. The repertoire may then be displayed in a suitable host system, such as the phage display system of WO92/01047, which is herein incorporated by reference in its entirety, or any of a subsequent large body of literature, including Kay, Winter & McCafferty [101], so that suitable binding members may be selected. A repertoire may consist of from anything from $10^4$ individual members upwards, for example at least $10^5$, at least $10^6$, at least $10^7$, at least $10^8$, at least $10^9$ or at least $10^{10}$ members or more. Other suitable host systems include, but are not limited to yeast display, bacterial display, T7 display, viral display, cell display, ribosome display and covalent display.

A method of preparing a binding member for IL-6 antigen is provided, which method comprises:
 (a) providing a starting repertoire of nucleic acids encoding a VH domain which either include a CDR3 to be replaced or lack a CDR3 encoding region;
 (b) combining said repertoire with a donor nucleic acid encoding an amino acid sequence substantially as set out herein for a VH CDR3 such that said donor nucleic acid is inserted into the CDR3 region in the repertoire, so as to provide a product repertoire of nucleic acids encoding a VH domain;
 (c) expressing the nucleic acids of said product repertoire;
 (d) selecting a binding member for IL-6; and
 (e) recovering said binding member or nucleic acid encoding it.

Again, an analogous method may be employed in which a VL CDR3 of the invention is combined with a repertoire of nucleic acids encoding a VL domain that either include a CDR3 to be replaced or lack a CDR3 encoding region.

Similarly, one or more, or all three CDRs may be grafted into a repertoire of VH or VL domains that are then screened for a binding member or binding members for IL-6.

For example, one or more of the parent or antibody 2, 3, 4, 5, 7, 8, 10, 14, 16, 17, 18, 19, 21, 22 or 23 HCDR1, HCDR2 and HCDR3 or the parent or antibody 2, 3, 4, 5, 7, 8, 10, 14, 16, 17, 18, 19, 21, 22 or 23 set of HCDRs may be employed, and/or one or more of the parent or antibody 2, 3, 4, 5, 7, 8, 10, 14, 16, 17, 18, 19, 21, 22 or 23 LCDR1, LCDR2 and LCDR3 or the parent or antibody 2, 3, 4, 5, 7, 8, 10, 14, 16, 17, 18, 19, 21, 22 or 23 set of LCDRs may be employed.

Similarly, other VH and VL domains, sets of CDRs and sets of HCDRs and/or sets of LCDRs disclosed herein may be employed.

A substantial portion of an immunoglobulin variable domain may comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including antibody constant regions, other variable domains (for example in the production of diabodies) or detectable/functional labels as discussed in more detail elsewhere herein.

Although in some aspects of the invention, binding members comprise a pair of VH and VL domains, single binding domains based on either VH or VL domain sequences form further aspects of the invention. It is known that single immunoglobulin domains, especially VH domains, are capable of binding target antigens in a specific manner. For example, see the discussion of dAbs above. In the case of either of the single binding domains, these domains may be used to screen for complementary domains capable of forming a two-domain binding member able to bind IL-6. This may be achieved by phage display screening methods using the so-called hierarchical dual combinatorial approach as disclosed in WO92/01047, herein incorporated by reference in its entirety, in which an individual colony containing either an H or L chain clone is used to infect a complete library of clones encoding the other chain (L or H) and the resulting two-chain binding member is selected in accordance with phage display techniques, such as those described in that reference. This technique is also disclosed in Marks et al, ibid. [100].

Binding members of the present invention may further comprise antibody constant regions or parts thereof, e.g. human antibody constant regions or parts thereof. For example, a VL domain may be attached at its C-terminal end to antibody light chain constant domains including human Cκ or Cλ chains. Similarly, a binding member based on a VH domain may be attached at its C-terminal end to all or part (e.g. a CH1 domain) of an immunoglobulin heavy chain derived from any antibody isotype, e.g. IgG, IgA, IgE and IgM and any of the isotype sub-classes, particularly IgG1 and IgG4. IgG1 is advantageous, due to its effector function and ease of manufacture. Any synthetic or other constant region variant that has these properties and stabilizes variable regions may also be useful in the present invention.

Binding members of the invention may be labelled with a detectable or functional label. Thus, a binding member or antibody molecule can be present in the form of an immunoconjugate so as to obtain a detectable and/or quantifiable signal. An immunoconjugates may comprise an antibody molecule of the invention conjugated with detectable or functional label. A label can be any molecule that produces or can be induced to produce a signal, including but not limited to fluorescers, radiolabels, enzymes, chemiluminescers or photosensitizers. Thus, binding may be detected and/or measured by detecting fluorescence or luminescence, radioactivity, enzyme activity or light absorbance.

Suitable labels include, by way of illustration and not limitation, enzymes, such as alkaline phosphatase, glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase e.g. horseradish peroxidase;

dyes;

fluorescent labels or fluorescers, such as fluorescein and its derivatives, fluorochrome, rhodamine compounds and derivatives, GFP (GFP for "Green Fluorescent Protein"), dansyl, umbelliferone, phycoerythrin, phycocyanin, allophycocyanin, o-phthaldehyde, and fluorescamine; fluorophores such as lanthanide cryptates and chelates e.g. Europium etc (Perkin Elmer and Cis Biointernational), chemoluminescent labels or chemiluminescers, such as isoluminol, luminol and the dioxetanes; bio-luminescent labels, such as luciferase and luciferin;

sensitizers;

coenzymes;

enzyme substrates;

radiolabels including but not limited to bromine-77, carbon14, cobalt57, fluorine8, gallium67, gallium 68, hydrogen3 (tritium), indium111, indium 113m, iodine123m, iodine125, iodine126, iodine131, iodine133, mercury107, mercury203, phosphorous32, rhenium99m, rhenium101, rhenium105, ruthenium95, ruthenium97, ruthenium103, ruthenium105, scandium47, selenium75, sulphur35, technetium99, technetium99m, tellurium121m, tellurium122m, tellurium125m, thulium165, thulium167, thulium168, yttrium199 and other radiolabels mentioned herein;

particles, such as latex or carbon particles; metal sol; crystallite; liposomes; cells, etc., which may be further labelled with a dye, catalyst or other detectable group;

molecules such as biotin, digoxygenin or 5-bromodeoxyuridine;

toxin moieties, such as for example a toxin moiety selected from a group of *Pseudomonas* exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

Suitable enzymes and coenzymes are disclosed in Litman, et al., U.S. Pat. No. 4,275,149, and Boguslaski, et al., U.S. Pat. No. 4,318,980, each of which are herein incorporated by reference in their entireties. Suitable fluorescers and chemiluminescers are disclosed in Litman, et al., U.S. Pat. No. 4,275,149, which is incorporated herein by reference in its entirety. Labels further include chemical moieties, such as biotin that may be detected via binding to a specific cognate detectable moiety, e.g. labelled avidin or streptavidin. Detectable labels may be attached to antibodies of the invention using conventional chemistry known in the art.

Immunoconjugates or their functional fragments can be prepared by methods known to the person skilled in the art. They can be coupled to enzymes or to fluorescent labels directly or by the intermediary of a spacer group or of a linking group, such as a polyaldehyde, like glutaraldehyde, ethylenediaminetetraacetic acid (EDTA), diethylene-triaminepentaacetic acid (DPTA), or in the presence of coupling agents, such as those mentioned above for the therapeutic conjugates. Conjugates containing labels of fluorescein type can be prepared by reaction with an isothiocyanate.

The methods known to the person skilled in the art existing for coupling the therapeutic radioisotopes to the antibodies either directly or via a chelating agent, such as EDTA, DTPA mentioned above can be used for the radioelements which can be used in diagnosis. It is likewise possible to perform labelling with sodium125 by the chloramine T method [102] or else with technetium99m by the technique of Crockford et al., (U.S. Pat. No. 4,424,200, herein incorporated by reference in its entirety) or attached via DTPA as described by Hnatowich (U.S. Pat. No. 4,479,930, herein incorporated by reference in its entirety).

There are numerous methods by which the label can produce a signal detectable by external means, for example, by visual examination, electromagnetic radiation, heat, and chemical reagents. The label can also be bound to another binding member that binds the antibody of the invention, or to a support.

The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. This second wavelength emission may also transfer energy to a labelled acceptor molecule, and the resultant energy dissipated from the acceptor molecule by emission of light for example fluorescence resonance energy transfer (FRET). Other labels that directly produce a signal include radioactive isotopes and dyes.

Alternately, the label may need other components to produce a signal, and the signal producing system would then include all the components required to produce a measurable signal, which may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al. U.S. Pat. No. 5,185,243, which is herein incorporated herein by reference in its entirety. The present invention provides a method comprising causing or allowing binding of a binding member as provided herein to IL-6. As noted, such binding may take place in vivo, e.g. following administration of a binding member, or nucleic acid encoding a binding member, or it may take place in vitro, for example in ELISA, Western blotting, immunocytochemistry, immunoprecipitation, affinity chromatography, and biochemical or cell-based assays, such as a TF-1 cell proliferation assay.

The present invention also provides for measuring levels of antigen directly, by employing a binding member according to the invention for example in a biosensor system. For instance, the present invention comprises a method of detecting and/or measuring binding to IL-6, comprising, (i) exposing said binding member to IL-6 and (ii) detecting binding of said binding member to IL-6, wherein binding is detected using any method or detectable label described herein. This, and any other binding detection method described herein, may be interpreted directly by the person performing the method, for instance, by visually observing a detectable label. Alternatively, this method, or any other binding detection method described herein, may produce a report in the form of an autoradiograph, a photograph, a computer printout, a flow cytometry report, a graph, a chart, a test tube or container or well containing the result, or any other visual or physical representation of a result of the method.

The amount of binding of binding member to IL-6 may be determined. Quantitation may be related to the amount of the antigen in a test sample, which may be of diagnostic interest. Screening for IL-6 binding and/or the quantitation thereof may be useful, for instance, in screening patients for diseases or disorders referred to herein and/or any other disease or disorder involving aberrant IL-6 expression and/or activity.

A diagnostic method of the invention may comprise (i) obtaining a tissue or fluid sample from a subject, (ii) exposing said tissue or fluid sample to one or more binding members of the present invention; and (iii) detecting bound IL-6 as compared with a control sample, wherein an increase in the amount of IL-6 binding as compared with the control may indicate an aberrant level of IL-6 expression or activity. Tissue or fluid samples to be tested include blood, serum, urine, biopsy material, tumours, or any tissue suspected of containing aberrant IL-6 levels. Subjects testing positive for aberrant IL-6 levels or activity may also benefit from the treatment methods disclosed later herein. Those skilled in the art are able to choose a suitable mode of determining binding of the binding member to an antigen according to their preference and general knowledge, in light of the methods disclosed herein.

The reactivities of binding members in a sample may be determined by any appropriate means. Radioimmunoassay (RIA) is one possibility. Radioactive labelled antigen is mixed with unlabelled antigen (the test sample) and allowed to bind to the binding member. Bound antigen is physically separated from unbound antigen and the amount of radioactive antigen bound to the binding member determined. The more antigen there is in the test sample the less radioactive antigen will bind to the binding member. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red, and lanthanide chelates or cryptates. Suitable chromogenic dyes include diaminobenzidine.

Other reporters include macromolecular colloidal particles or particulate material, such as latex beads that are colored, magnetic or paramagnetic, and biologically or chemically active agents that can directly or indirectly cause detectable signals to be visually observed, electronically detected or otherwise recorded. These molecules may be enzymes, which catalyze reactions that develop, or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual binding member-reporter conjugates may be used to derive quantifiable absolute or relative data of the relevant binding member binding in samples (normal and test).

A kit comprising a binding member according to any aspect or embodiment of the present invention is also provided as an aspect of the present invention. In the kit, the binding member may be labelled to allow its reactivity in a sample to be determined, e.g. as described further below. Further the binding member may or may not be attached to a solid support. Components of a kit are generally sterile and in sealed vials or other containers. Kits may be employed in diagnostic analysis or other methods for which binding members are useful. A kit may contain instructions for use of the components in a method, e.g. a method in accordance with the present invention. Ancillary materials to assist in or to enable performing such a method may be included within a kit of the invention. The ancillary materials include a second, different binding member which binds to the first binding member and is conjugated to a detectable label (e.g., a fluorescent label, radioactive isotope or enzyme). Antibody-based kits may also comprise beads for conducting an immunoprecipitation. Each component of the kits is generally in its own suitable container. Thus, these kits generally comprise distinct containers suitable for each binding member. Further, the kits may comprise instructions for performing the assay and methods for interpreting and analyzing the data resulting from the performance of the assay.

The present invention also provides the use of a binding member as above for measuring antigen levels in a competition assay, that is to say a method of measuring the level of antigen in a sample by employing a binding member as provided by the present invention in a competition assay. This may be where the physical separation of bound from unbound antigen is not required. Linking a reporter molecule to the binding member so that a physical or optical change occurs on binding is one possibility. The reporter molecule may directly or indirectly generate detectable signals, which may be quantifiable. The linkage of reporter molecules may be directly or indirectly, covalently, e.g. via a peptide bond or non-covalently. Linkage via a peptide bond may be as a result of recombinant expression of a gene fusion encoding antibody and reporter molecule.

In various aspects and embodiments, the present invention extends to a binding member that competes for binding to IL-6 with any binding member defined herein, e.g. the parent antibody or any of antibodies 2, 3, 4, 5, 7, 8, 10, 14, 16, 17, 18, 19, 21, 22 and 23, e.g. in IgG1 format. Competition between binding members may be assayed easily in vitro, for example by tagging a specific reporter molecule to one binding member which can be detected in the presence of other untagged binding member(s), to enable identification of binding members which bind the same epitope or an overlapping epitope. Competition may be determined for example using ELISA in which IL-6 is immobilized to a plate and a first tagged or labelled binding member along with one or more other untagged or unlabelled binding members is added to the plate. Presence of an untagged binding member that competes with the tagged binding member is observed by a decrease in the signal emitted by the tagged binding member.

For example, the present invention includes a method of identifying an IL-6 binding compound, comprising (i) immobilizing IL-6 to a support, (ii) contacting said immobilized IL-6 simultaneously or in a step-wise manner with at least one tagged or labelled binding member according to the invention and one or more untagged or unlabelled test binding compounds, and (iii) identifying a new IL-6 binding compound by observing a decrease in the amount of bound tag from the tagged binding member. Such methods can be performed in a high-throughput manner using a multiwell or array format. Such assays may be also be performed in solution. See, for instance, U.S. Pat. No. 5,814,468, which is herein incorporated by reference in its entirety. As described above, detection of binding may be interpreted directly by the person performing the method, for instance, by visually observing a detectable label, or a decrease in the presence thereof. Alternatively, the binding methods of the invention may produce a report in the form of an autoradiograph, a photograph, a computer printout, a flow cytometry report, a graph, a chart, a test tube or container or well containing the result, or any other visual or physical representation of a result of the method.

Competition assays can also be used in epitope mapping. In one instance epitope mapping may be used to identify the epitope bound by an IL-6 binding member which optionally may have optimized neutralizing and/or modulating characteristics. Such an epitope can be linear or conformational. A conformational epitope can comprise at least two different fragments of IL-6, wherein said fragments are positioned in proximity to each other when IL-6 is folded in its tertiary or quaternary structure to form a conformational epitope which is recognized by an inhibitor of IL-6, such as an IL-6-binding member. In testing for competition a peptide fragment of the antigen may be employed, especially a peptide including or consisting essentially of an epitope of interest. A peptide having the epitope sequence plus one or more amino acids at either end may be used. Binding members according to the present invention may be such that their binding for antigen is inhibited by a peptide with or including the sequence given.

The present invention further provides an isolated nucleic acid encoding a binding member of the present invention. Nucleic acid may include DNA and/or RNA. In one, the present invention provides a nucleic acid that codes for a CDR or set of CDRs or VH domain or VL domain or antibody antigen-binding site or antibody molecule, e.g. scFv or IgG1, of the invention as defined above.

The present invention also provides constructs in the form of plasmids, vectors, transcription or expression cassettes which comprise at least one polynucleotide as above.

The present invention also provides a recombinant host cell that comprises one or more constructs as above. A nucleic acid encoding any CDR or set of CDRs or VH domain or VL domain or antibody antigen-binding site or antibody molecule, e.g. scFv or IgG1 as provided, itself forms an aspect of the present invention, as does a method of production of the encoded product, which method comprises expression from encoding nucleic acid therefor. Expression may conveniently be achieved by culturing under appropriate conditions recombinant host cells containing the nucleic acid. Following production by expression a VH or VL domain, or binding member may be isolated and/or purified using any suitable technique, then used as appropriate.

Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

A yet further aspect provides a method of production of an antibody VH variable domain, the method including causing expression from encoding nucleic acid. Such a method may comprise culturing host cells under conditions for production of said antibody VH variable domain.

Analogous methods for production of VL variable domains and binding members comprising a VH and/or VL domain are provided as further aspects of the present invention.

A method of production may comprise a step of isolation and/or purification of the product. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, filamentous fungi, yeast and baculovirus systems and transgenic plants and animals.

The expression of antibodies and antibody fragments in prokaryotic cells is well established in the art. For a review, see for example Plückthun [103]. A common bacterial host is *E. coli*.

Expression in eukaryotic cells in culture is also available to those skilled in the art as an option for production of a binding member [104, 105, 106]. Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids e.g. phagemid, or viral e.g. 'phage, as appropriate [107]. Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. [108].

A further aspect of the present invention provides a host cell containing nucleic acid as disclosed herein. Such a host cell may be in vitro and may be in culture. Such a host cell may be in vivo. In vivo presence of the host cell may allow intra-cellular expression of the binding members of the present invention as "intrabodies" or intra-cellular antibodies. Intrabodies may be used for gene therapy.

A still further aspect provides a method comprising introducing nucleic acid of the invention into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene. The purification of the expressed product may be achieved by methods known to one of skill in the art.

Nucleic acid of the invention may be integrated into the genome (e.g. chromosome) of the host cell. Integration may be promoted by inclusion of sequences that promote recombination with the genome, in accordance with standard techniques.

The present invention also provides a method that comprises using a construct as stated above in an expression system in order to express a binding member or polypeptide as above.

There is evidence for involvement of IL-6 in a variety of disorders, as discussed elsewhere herein. The binding members of the present invention may therefore be used in a method of diagnosis or treatment of a disorder associated with IL-6. Such a disorder may for example be an inflammatory and/or autoimmune disorder such as for example, rheumatoid arthritis, osteoarthritis, cachexia, chronic obstructive pulmonary disease, Juvenile idiopathic arthritis, asthma, systemic lupus erythematosus, inflammatory bowel disease, Crohn's disease or atherosclerosis. A binding member of the present invention may also be used to treat a disorder such as a tumour and/or cancer.

Binding members of the present invention may also be used in method of diagnosis or treatment of at least one IL-6 related disease, in a patient, animal, organ, tissue or cell, including, but not limited to:—

(the respiratory tract) obstructive airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis; acute-, allergic-, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis, sinusitis, idiopathic pulmonary fibrosis (IPF); sarcoidosis, farmer's lung and related diseases, adult respiratory distress syndrome, hypersensitivity pneumonitis, fibroid lung and idiopathic interstitial pneumonia;

(bone and joints) rheumatoid arthritis, juvenile chronic arthritis, systemic onset juvenile arthritis, seronegative spondyloarthropathies (including ankylosing spondylitis, psoriatic arthritis and Reiter's disease), Behcet's disease, Siogren's syndrome and systemic sclerosis, gout, osteoporosis and osteoarthritis;

(skin) psoriasis, atopical dermatitis, contact dermatitis and other eczmatous dermatoses, allergic contact dermatitis, seborrhoetic dermatitis, Lichen planus, scleroderma, Pemphigus, bullous pemphigoid, Epidermolysis bullosa, urticaria, angiodermas, vasculitides, erythemas, cutaneous eosinophilias, uveitis, Alopecia greata, allergic conjunctivitis and vernalvemal conjunctivitis;

(gastrointestinal tract) gastric ulcer, Coeliac disease, proctitis, eosinophilic gastro-enteritis, mastocytosis, inflammatory bowel disease, Crohn's disease, ulcerative colitis, antiphospholipid syndrome)), food-related allergies which have effects remote from the gut, e.g., migraine, rhinitis and eczema;

(other tissues and systemic disease) cachexia, multiple sclerosis, atherosclerosis, Acquired Immunodeficiency Syndrome (AIDS), mesangial proliferative glomerulonephritis, nephrotic syndrome, nephritis, glomerular nephritis, acute renal failure, hemodialysis, uremia, localised or discoid lupus erythematosus, systemic lupus erythematosus, Castleman's Disease, Hashimoto's thyroiditis, myasthenia gravis, type I diabetes, type B insulin-resistant diabetes, sickle cell anaemia, iridocyclitis/uveitis/optic neuritis, nephritic syndrome, eosinophilia fascitis, hyper IgE syndrome, systemic vasculitis/wegener's granulomatosis, orchitis/vasectomy reversal procedures, lepromatous leprosy, alcohol-induced hepatitis, sezary syndrome and idiopathic thrombocytopenia purpura; post-operative adhesions, nephrosis, systemic inflammatory response syndrome, sepsis syndrome, gram positive sepsis, gram negative sepsis, culture negative sepsis, fungal sepsis, neutropenic fever, acute pancreatitis, urosepsis, Graves disease, Raynaud's disease, antibody-mediated cytotoxicity, type III hypersensitivity reactions, POEMS syndrome (polyneuropathy, organomegaly, endocrinopathy, monoclonal gammopathy, and skin changes syndrome), mixed connective tissue disease, idiopathic Addison's disease, diabetes mellitus, chronic active hepatitis, primary biliary cirrhosis, vitiligo, post-MI (cardiotomy) syndrome, type IV hypersensitivity, granulomas due to intracellular organisms, Wilson's disease, hemachromatosis, alpha-I-antitrypsin deficiency, diabetic retinopathy, hashimoto's thyroiditis, hypothalamic-pituitary-adrenal axis evaluation, thyroiditis, encephalomyelitis, neonatal chronic lung disease, familial hematophagocytic lymphohistiocytosis, alopecia, radiation therapy (e.g., including but not limited to asthenia, anemia, cachexia, and the like), chronic salicylate intoxication, sleep apnea, obesity, heart failure, and meningococcemia;

(allograft rejection) acute and chronic following, for example, transplantation of kidney, heart, liver, lung, pancreas, bone marrow, bone, small bowel, skin, cartilage and cornea; and chronic graft versus host disease;

(malignant disease) leukaemia, acute lymphoblastic leukaemia (ALL), acute leukaemia, T-cell, B-cell, or FAB ALL, chromic myelocytic leukaemia (CML), acute myeloid leukaemia (AML), chronic lymphocytic leukaemia (CLL), hairy cell leukaemia, myelodyplastic syndrome (MDS), any lymphoma, Hodgkin's disease, non-hodgkin's lymphoma, any malignant lymphoma, Burkitt's lymphoma, multiple myeloma, Kaposi's sarcoma, renal cell carcinoma, colorectal carcinoma, prostatic carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain; the suppression of cancer metastasis; the amelioration of cancer cachexia;

Cystic fibrosis, stroke, re-perfusion injury in the heart, brain, peripheral limbs and other organs;

Burn wounds, trauma/haemorrhage, ionizing radiation exposure, chronic skin ulcers;

Reproductive Diseases (e.g. Disorders of ovulation, menstruation and implantation, pre-term labour, pre-eclampsia, endometriosis);

(Infections) acute or chronic bacterial infection, acute and chronic parasitic or infectious processes, including bacterial, viral and fungal infections, HIV infection/HIV neuropathy, meningitis, hepatitis (A, B or C, or other viral hepatitis the like), septic arthritis, peritonitis, pneumonia, epiglottis, *E. coli* 0157:h7, hemolytic uremic syndrome/thrombotic thrombocytopenic purpura, malaria, dengue hemorrhagic fever, leishmaniasis, leprosy, toxic shock syndrome, streptococcal myositis, gas gangrene, *mycobacterium tuberculosis, mycobacterium avium* intracellulare, *pneumocystis carinii* pneumonia, pelvic inflammatory disease, orchitis/epidydimitis, *legionella*, Lyme disease, influenza a, epstein-barr virus, vital-associated hemaphagocytic syndrome, viral encephalitis/aseptic meningitis, and the like.

Accordingly, the invention provides a method of treating an IL-6 related disorder, comprising administering to a patient in need thereof an effective amount of one or more binding members of the present invention alone or in a combined therapeutic regimen with another appropriate medicament known in the art or described herein.

Evidence for involvement of IL-6 in certain disorders is summarised elsewhere herein. In addition, the data presented herein further indicates that binding members of the invention can be used to treat such disorders, including preventative treatment and reduction of severity of the disorders. Accordingly, the invention provides a method of treating or reducing the severity of at least one symptom of any of the disorders mentioned herein, comprising administering to a patient in need thereof an effective amount of one or more binding members of the present invention alone or in a combined therapeutic regimen with another appropriate medicament known in the art or described herein such that the severity of at least one symptom of any of the above disorders is reduced.

Thus, the binding members of the present invention are useful as therapeutic agents in the treatment of diseases or disorders involving IL-6 and/or IL-6Ra expression and/or activity, especially aberrant expression/activity. A method of treatment may comprise administering an effective amount of a binding member of the invention to a patient in need thereof, wherein aberrant expression and/or activity of IL-6 and/or IL-6Ra is decreased. A method of treatment may comprise (i) identifying a patient demonstrating aberrant IL-6:IL-6Ra levels or activity, for instance using the diagnostic methods described above, and (ii) administering an effective amount of a binding member of the invention to the patient, wherein aberrant expression and/or activity of IL-6Ra and/or IL-6 is decreased. An effective amount according to the invention is an amount that decreases the aberrant expression and/or activity of IL-6 and/or IL-6Ra so as to decrease or lessen the severity of at least one symptom of the particular disease or disorder being treated, but not necessarily cure the disease or disorder.

The invention also provides a method of antagonising at least one effect of IL-6, comprising contacting with or administering an effective amount of one or more binding members of the present invention such that said at least one effect of IL-6 is antagonised. Effects of IL-6 that may be antagonised by the methods of the invention include IL-6 binding to gp130, and downstream effects that arise as a consequence of this binding. Accordingly, further aspects of the invention provide methods of treatment comprising administration of a binding member as provided, pharmaceutical compositions comprising such a binding member, and use of such a binding member in the manufacture of a medicament for administration, for example in a method of making a medicament or pharmaceutical composition comprising formulating the binding member with a pharmaceutically acceptable excipient. A pharmaceutically acceptable excipient may be a compound or a combination of compounds entering into a pharmaceutical composition not provoking secondary reactions and which allows, for example, facilitation of the administration of the active compound(s), an increase in its lifespan and/or in its efficacy in the body, an increase in its solubility in solution or else an improvement in its conservation. These pharmaceutically acceptable vehicles are well known and will be adapted by the person skilled in the art as a function of the nature and of the mode of administration of the active compound(s) chosen.

Binding members of the present invention will usually be administered in the form of a pharmaceutical composition, which may comprise at least one component in addition to the binding member. Thus pharmaceutical compositions according to the present invention, and for use in accordance with the present invention, may comprise, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, inhaled, intra-tracheal, topical, intra-vesicular or by injection, as discussed below.

Pharmaceutical compositions for oral administration, such as for example single domain antibody molecules (e.g. "NANOBODIES™" (camelid VH dAbs)) etc are also envisaged in the present invention. Such oral formulations may be in tablet, capsule, powder, liquid or semi-solid form. A tablet may comprise a solid carrier, such as gelatin or an adjuvant. Liquid pharmaceutical compositions generally comprise a liquid carrier, such as water, petroleum, animal or vegetable oils, mineral oil or synthetic oil. Physiological saline solution, dextrose or other saccharide solution or glycols, such as ethylene glycol, propylene glycol or polyethylene glycol may be included.

For intra-venous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

Binding members of the present invention may be formulated in liquid, semi-solid or solid forms depending on the physicochemical properties of the molecule and the route of delivery. Formulations may include excipients, or combinations of excipients, for example: sugars, amino acids and surfactants. Liquid formulations may include a wide range of antibody concentrations and pH. Solid formulations may be produced by lyophilisation, spray drying, or drying by supercritical fluid technology, for example. Formulations of binding members will depend upon the intended route of delivery: for example, formulations for pulmonary delivery may consist of particles with physical properties that ensure penetration into the deep lung upon inhalation; topical formulations (e.g. for treatment of scarring, e.g. dermal scarring) may include viscosity modifying agents, which prolong the time that the drug is resident at the site of action. A binding member may be prepared with a carrier that will protect the binding member against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known to those skilled in the art [109].

Treatment may be given orally (such as for example single domain antibody molecules (e.g. "NANOBODIES™" (camelid VH dAbs)) by injection (for example, subcutaneously, intra-articular, intra-venously, intra-peritoneal, intra-arterial or intra-muscularly), by inhalation, intra-tracheal, by the intra-vesicular route (instillation into the urinary bladder), or topically (for example intra-ocular, intra-nasal, rectal, into wounds, on skin). The treatment may be administered by pulse infusion, particularly with declining doses of the binding member. The route of administration can be determined by the physicochemical characteristics of the treatment, by special considerations for the disease or by the requirement to optimize efficacy or to minimize side-effects. One particular route of administration is intra-venous. Another route of administering pharmaceutical compositions of the present invention is subcutaneously. It is envisaged that treatment will not be restricted to use in the clinic. Therefore, subcutaneous injection using a needle-free device is also advantageous.

A composition may be administered alone or in combination with other treatments, either simultaneously or sequentially dependent upon the condition to be treated.

A binding member of the invention may be used as part of a combination therapy in conjunction with an additional medicinal component. Combination treatments may be used to provide significant synergistic effects, particularly the combination of a binding member of the invention with one or more other drugs. A binding member of the invention may be administered concurrently or sequentially or as a combined preparation with another therapeutic agent or agents, for the treatment of one or more of the conditions listed herein.

A binding member of the invention may be used as a chemosensitiser whereby it can increase therapeutic efficacy of cytotoxic agents, and may thus be provided for administration in combination with one or more cytotoxic agents, either simultaneously or sequentially. The binding member may also be used as a radio sensitiser whereby it can improve efficacy of radiation, and may thus be provided for administration in combination with radiation, either simultaneously or sequentially.

A binding member according to the present invention may be provided in combination or addition with one or more of the following agents:

a cytokine or agonist or antagonist of cytokine function (e.g. an agent which acts on cytokine signalling pathways, such as a modulator of the SOCS system), such as an alpha-, beta- and/or gamma-interferon; insulin-like growth factor type I (IGF-1), its receptors and associated binding proteins; interleukins (IL), e.g. one or more of IL-1 to –33, and/or an interleukin antagonist or inhibitor, such as anakinra; inhibitors of receptors of interleukin family members or inhibitors of specific subunits of such receptors, a tumour necrosis factor alpha (TNF-α) inhibitor, such as an anti-TNF monoclonal antibodies (for example infliximab, adalimumab and/or CDP-870) and/or a TNF receptor antagonist, e.g. an immunoglobulin molecule (such as etanercept) and/or a low-molecular-weight agent, such as pentoxyfylline;

a modulator of B cells, e.g. a monoclonal antibody targeting B-lymphocytes (such as CD20 (rituximab) or MRA-aIL16R) or T-lymphocytes (e.g. CTLA4-Ig, HuMax Il-15 or Abatacept);

a modulator that inhibits osteoclast activity, for example an antibody to RANKL;

a modulator of chemokine or chemokine receptor function, such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 and CXCR6 (for the C—X—C family) and $CX_3CR1$ for the C—$X_3$—C family;

an inhibitor of matrix metalloproteases (MMPs), i.e. one or more of the stromelysins, the collagenases and the gelatinases as well as aggrecanase, especially collagenase-1 (MMP-1), collagenase-2 (MMP-8), collagenase-3 (MMP-13), stromelysin-1 (MMP-3), stromelysin-2 (MMP-10) and/or stromelysin-3 (MMP-11) and/or MMP-9 and/or MMP-12, e.g. an agent such as doxycycline;

a leukotriene biosynthesis inhibitor, 5-lipoxygenase (5-LO) inhibitor or 5-lipoxygenase activating protein (FLAP) antagonist, such as zileuton; ABT-761; fenleuton; tepoxalin; Abbott-79175; Abbott-85761; N-(5-substituted)-thiophene-2-alkylsulfonamides; 2,6-di-tert-butylphenolhydrazones; methoxytetrahydropyrans such as Zeneca ZD-2138; the compound SB-210661; a pyridinyl-substituted 2-cyanonaphthalene compound, such as L-739,010; a 2-cyanoquinoline compound, such as L-746,530; indole and/or a quinoline compound, such as MK-591, MK-886 and/or BAY x 1005;

a receptor antagonist for leukotrienes (LT) B4, LTC4, LTD4, and LTE4, selected from the group consisting of the phenothiazin-3-ls, such as L-651,392; amidino compounds, such as CGS-25019c; benzoxalamines, such as ontazolast; benzenecarboximidamides, such as BIIL 284/260; and compounds, such as zafirlukast, ablukast, montelukast, pranlukast, verlukast (MK-679), RG-12525, Ro-245913, iralukast (CGP 45715A) and BAY x 7195;

a phosphodiesterase (PDE) inhibitor, such as a methylxanthanine, e.g. theophylline and/or aminophylline; and/or a selective PDE isoenzyme inhibitor, e.g. a PDE4 inhibitor and/or inhibitor of the isoform PDE4D and/or an inhibitor of PDE5;

a histamine type 1 receptor antagonist, such as cetirizine, loratadine, desloratadine, fexofenadine, acrivastine, terfenadine, astemizole, azelastine, levocabastine, chlorpheniramine, promethazine, cyclizine, and/or mizolastine (generally applied orally, topically or parenterally);

a proton pump inhibitor (such as omeprazole) or gastroprotective histamine type 2 receptor antagonist;

an antagonist of the histamine type 4 receptor;

an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride and ethylnorepinephrine hydrochloride;

an anticholinergic agent, e.g. a muscarinic receptor (M1, M2, and M3) antagonist, such as atropine, hyoscine, glycopyrrolate, ipratropium bromide, tiotropium bromide, oxitropium bromide, pirenzepine and telenzepine;

a beta-adrenoceptor agonist (including beta receptor subtypes 1-4), such as isoprenaline, salbutamol, formoterol, salmeterol, terbutaline, orciprenaline, bitolterol mesylate and/or pirbuterol, e.g. a chiral enantiomer thereof;

a chromone, e.g. sodium chromoglycate and/or nedocromil sodium;

a glucocorticoid, such as flunisolide, triamcinolone acetonide, beclomethasone dipropionate, budesonide, fluticasone propionate, ciclesonide, and/or mometasone furoate;

an agent that modulate nuclear hormone receptors, such as a PPAR;

an immunoglobulin (Ig) or Ig preparation or an antagonist or antibody modulating Ig function, such as anti-IgE (e.g. omalizumab);

other systemic or topically-applied anti-inflammatory agent, e.g. thalidomide or a derivative thereof, a retinoid, dithranol and/or calcipotriol;

combinations of aminosalicylates and sulfapyridine, such as sulfasalazine, mesalazine, balsalazide, and olsalazine; and immunomodulatory agents, such as the thiopurines; and corticosteroids, such as budesonide;

an antibacterial agent, e.g. a penicillin derivative, a tetracycline, a macrolide, a beta-lactam, a fluoroquinolone, metronidazole and/or an inhaled aminoglycoside; and/or an antiviral agent, e.g. acyclovir, famciclovir, valaciclovir, ganciclovir, cidofovir; amantadine, rimantadine; ribavirin; zanamavir and/or oseltamavir; a protease inhibitor, such as indinavir, nelfinavir, ritonavir and/or saquinavir; a nucleoside reverse transcriptase inhibitor, such as didanosine, lamivudine, stavudine, zalcitabine, zidovudine; a non-nucleoside reverse transcriptase inhibitor, such as nevirapine, efavirenz;

a cardiovascular agent, such as a calcium channel blocker, beta-adrenoceptor blocker, angiotensin-converting enzyme (ACE) inhibitor, angiotensin-2 receptor antagonist; lipid lowering agent, such as a statin and/or fibrate; a modulator of blood cell morphology, such as pentoxyfylline; a thrombolytic and/or an anticoagulant, e.g. a platelet aggregation inhibitor;

a CNS agent, such as an antidepressant (such as sertraline), anti-Parkinsonian drug (such as deprenyl, L-dopa, ropinirole, pramipexole; MAOB inhibitor, such as selegine and rasagiline; comP inhibitor, such as tasmar; A-2 inhibitor, dopamine reuptake inhibitor, NMDA antagonist, nicotine agonist, dopamine agonist and/or inhibitor of neuronal nitric oxide synthase) and an anti-Alzheimer's drug, such as donepezil, rivastigmine, tacrine, COX-2 inhibitor, propentofylline or metrifonate;

an agent for the treatment of acute and chronic pain, e.g. a centrally or peripherally-acting analgesic, such as an opioid analogue or derivative, carbamazepine, phenyloin, sodium valproate, amitryptiline or other antidepressant agent, paracetamol, or non-steroidal anti-inflammatory agent;

a parenterally or topically-applied (including inhaled) local anaesthetic agent, such as lignocaine or an analogue thereof;

an anti-osteoporosis agent, e.g. a hormonal agent, such as raloxifene, or a biphosphonate, such as alendronate;

(i) a tryptase inhibitor; (ii) a platelet activating factor (PAF) antagonist; (iii) an interleukin converting enzyme (ICE) inhibitor; (iv) an IMPDH inhibitor; (v) an adhesion molecule inhibitors including VLA-4 antagonist; (vi) a cathepsin; (vii) a kinase inhibitor, e.g. an inhibitor of tyrosine kinases (such as Btk, Itk, Jak3 MAP examples of inhibitors might include Gefitinib, Imatinib mesylate), a serine/threonine kinase (e.g. an inhibitor of MAP kinase, such as p38, JNK, protein kinases A, B and C and IKK), or a kinase involved in cell cycle regulation (e.g. a cylin dependent kinase); (viii) a glucose-6 phosphate dehydrogenase inhibitor; (ix) a kinin-B.sub1.- and/or B.sub2.-receptor antagonist; (x) an anti-gout agent, e.g. colchicine; (xi) a xanthine oxidase inhibitor, e.g. allopurinol; (xii) a uricosuric agent, e.g. probenecid, sulfinpyrazone, and/or benzbromarone; (xiii) a growth hormone secretagogue; (xiv) transforming growth factor (TGFβ); (xv) platelet-derived growth factor (PDGF); (xvi) fibroblast growth factor, e.g. basic fibroblast growth factor (bFGF); (xvii) granulocyte macrophage colony stimulating factor (GM-CSF); (xviii) capsaicin cream; (xix) a tachykinin NK.sub1. and/or NK.sub3. receptor antagonist, such as NKP-608C, SB-233412 (talnetant) and/or D-4418; (xx) an elastase inhibitor, e.g. UT-77 and/or ZD-0892; (xxi) a TNF-alpha converting enzyme inhibitor (TACE); (xxii) induced nitric oxide synthase (iNOS) inhibitor or (xxiii) a chemoattractant receptor-homologous molecule expressed on TH2 cells (such as a CRTH2 antagonist); (xxiv) an inhibitor of a P38 (xxv) agent modulating the function of Toll-like receptors (TLR) and (xxvi) an agent modulating the activity of purinergic receptors, such as P2×7; (xxvii) an inhibitor of transcription factor activation, such as NFkB, API, and/or STATS.

An inhibitor may be specific or may be a mixed inhibitor, e.g. an inhibitor targeting more than one of the molecules (e.g. receptors) or molecular classes mentioned above.

The binding member could also be used in association with a chemotherapeutic agent or another tyrosine kinase inhibitor in co-administration or in the form of an immunoconjugate. Fragments of said antibody could also be use in bispecific antibodies obtained by recombinant mechanisms or biochemical coupling and then associating the specificity of the above described antibody with the specificity of other antibodies able to recognize other molecules involved in the activity for which IL-6 is associated.

For treatment of an inflammatory disease, a binding member of the invention may be combined with one or more agents, such as non-steroidal anti-inflammatory agents (hereinafter NSAIDs) including non-selective cyclo-oxygenase (COX)-1/COX-2 inhibitors whether applied topically or systemically, such as piroxicam, diclofenac, propionic acids, such as naproxen, flurbiprofen, fenoprofen, ketoprofen and ibuprofen, fenamates, such as mefenamic acid, indomethacin, sulindac, azapropazone, pyrazolones, such as phenylbutazone, salicylates, such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intra-muscular, intra-venous or intra-articular routes); methotrexate, leflunomide; hydroxychloroquine, d-penicillamine, auranofin or other parenteral or oral gold preparations; analgesics; diacerein; intra-articular therapies, such as hyaluronic acid derivatives; and nutritional supplements, such as glucosamine.

A binding member of the invention can also be used in combination with an existing therapeutic agent for the treatment of cancer. Suitable agents to be used in combination include:

(i) antiproliferative/antineoplastic drugs and combinations thereof, as used in medical oncology, such as Gleevec® (imatinib mesylate), alkylating agents (for example cis-platin, carboplatin, cyclophosphamide, nitrogen mustard, melphalan, chlorambucil, busulphan and nitrosoureas); antimetabolites (for example antifolates, such as fluoropyrimidines like 5-fluorouracil and tegafur, raltitrexed, methotrexate, cytosine arabinoside, hydroxyurea, gemcitabine and paclitaxel); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like (Taxol® (Paclitaxel) and taxotere); and topoisomerase inhibitors (for example epipodophyllotoxins like etoposide and teniposide, amsacrine, topotecan and camptothecins);

(ii) cytostatic agents, such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase, such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy)quinazolin-4-amine (gefitinib, AZD1839), N-(3-ethynylphenyl)-6,7-bis (2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents, such as those which inhibit the effects of vascular endothelial growth factor (for example the anti-vascular endothelial cell growth factor antibody bevacizumab, compounds, such as those disclosed in International Patent Applications WO 97/22596, WO 97/30035, WO 97/32856 and WO 98/13354, each of which is incorporated herein in its entirety) and compounds that work by other mechanisms (for example linomide, inhibitors of integrin αvβ3 function and angiostatin);

(vi) vascular damaging agents, such as combretastatin A4 and compounds disclosed in International Patent Applications WO 99/02166, WO 00/40529, WO 00/41669, WO 01/92224, WO 02/04434 and WO 02/08213 (each of which is incorporated herein in its entirety);

(vii) antisense therapies, for example those which are directed to the targets listed above, such as ISIS 2503, an anti-ras antisense;

(viii) gene therapy approaches, including for example approaches to replace aberrant genes, such as aberrant p53 or aberrant BRCA1 or BRCA2, GDEPT (gene directed enzyme pro-drug therapy) approaches, such as those using cytosine deaminase, thymidine kinase or a bacterial nitroreductase enzyme and approaches to increase patient tolerance to chemotherapy or radiotherapy, such as multi-drug resistance gene therapy; and (ix) immunotherapeutic approaches, including for example ex vivo and in vivo approaches to increase the immunogenicity of patient tumour cells, such as transfection with cytokines, such as interleukin 2, interleukin 4 or granulocyte macrophage colony stimulating factor, approaches to decrease T-cell energy, approaches using transfected immune cells, such as cytokine-transfected dendritic cells, approaches using cytokine-transfected tumour cell lines and approaches using anti-idiotypic antibodies.

A binding member of the invention and one or more of the above additional medicinal components may be used in the manufacture of a medicament. The medicament may be for separate or combined administration to an individual, and accordingly may comprise the binding member and the additional component as a combined preparation or as separate preparations. Separate preparations may be used to facilitate separate and sequential or simultaneous administration, and allow administration of the components by different routes e.g. oral and parenteral administration.

In accordance with the present invention, compositions provided may be administered to mammals. Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the type of binding member, the method of administration, the scheduling of administration and other factors known to medical practitioners. Prescription of treatment, e.g. decisions on dosage etc, is within the responsibility of general practitioners and other medical doctors and may depend on the severity of the symptoms and/or progression of a disease being treated. Appropriate doses of antibody are well known in the art [110, 111]. Specific dosages indicated herein or in the Physician's Desk Reference (2003) as appropriate for the type of medicament being administered may be used. A therapeutically effective amount or suitable dose of a binding member of the invention can be determined by comparing its in vitro activity and in vivo activity in an animal model. Methods for extrapolation of effective dosages in mice and other test animals to humans are known. The precise dose will depend upon a number of factors, including whether the antibody is for diagnosis, prevention or for treatment, the size and location of the area to be treated, the precise nature of the antibody (e.g. whole antibody, fragment or diabody) and the nature of any detectable label or other molecule attached to the antibody. A typical antibody dose will be in the range 100 µg to 1 g for systemic applications, and 1 µg to 1 mg for topical applications. An initial higher loading dose, followed by one or more lower doses, may be administered. Typically, the antibody will be a whole antibody, e.g. the IgG1 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. Treatments may be every two to four weeks for subcutaneous administration and every four to eight weeks for intra-venous administration. Treatment may be periodic, and the period between administrations is about two weeks or more, e.g. about three weeks or more, about four weeks or more, or about once a month. Treatment may be given before, and/or after surgery, and/or may be administered or applied directly at the anatomical site of surgical treatment.

IL-6 binding members of the invention may offer advantages in terms of dosage and administration requirements, compared with antibodies to sIL-6Ra. As noted elsewhere herein, circulating levels of IL-6 are significantly lower than circulating levels of sIL-6Ra in disease. Accordingly, use of an IL-6 binding member, as opposed to an anti-IL-6R binding member, has significant advantages in that the amount of drug to be manufactured for each dose to patients may be lower. Also if the dose of an anti-IL6 therapeutic is lower there may be significant advantages in that the low dose facilitates sub-cutaneous injections as well as intra-venous (i.v.) injections. It is well known to those skilled in the art that sub-cutaneous dosing may be limited by the amount of binding member, e.g. antibody molecule, required per dose. This is due to the sub-cutaneous injections being limited by the volume that can be injected at one site in the skin. Sub-cutaneous injection volumes of 1.2 ml or less are typically utilised. As it may be increasingly difficult to formulate a binding member for sub-cutaneous injection at concentrations greater than 50 mg/ml, doses above 100 mg via this route usually require multiple injections and more discomfort for the patient.

Having a lower dose anti-IL-6 therapeutic may also require a lower "loading" dose of antibody to inhibit all the systemic IL-6 compared with the systemic sIL-6Ra as this is at higher concentrations.

Further benefits may be associated with targeting IL-6 rather than IL-6 receptor, representing additional advantages of binding members of the invention as compared with binding members for IL-6Ra.

For example, there are literature reports which show that the circulating levels of IL-6 are significantly lower than circulating levels of sIL-6Ra in disease [112, 113]. As the levels of sIL-6R are significantly higher than IL-6 levels, more anti-sIL-6R binding member may be required to neutralise the sIL-6Ra, compared with the amount of anti-IL-6 binding member required to neutralise IL-6. Hence, a lower dose of an anti-ligand binding member may be needed, compared with if an anti-receptor binding member were used.

Targeting IL-6 ligand rather than IL-6 receptor may reduce levels of IL-6 in disease but still allow IL-6 levels to increase during infection, where IL-6 is up-regulated as part of the immune response.

Kawano et al. [4] showed that IL-6 was a potent growth factor and showed that myeloma cells freshly isolated from patients produced IL-6 and express its receptors. Moreover, anti-IL-6 antibody inhibits the in vitro growth of myeloma cells. This is direct evidence that an autocrine loop is operating in oncogenesis of human myelomas. Subsequent to that study, Van Zaanen et al. [5] demonstrated that the production of IL-6 in multiple myeloma patients decreases when treated with an anti-IL-6 ligand antibody.

A number of further studies show that IL-6 is involved in an autocrine feedback loop in other cell types e.g. smooth muscle cells (SMC) [114], U373-MG astroglioma cells [115], 3T3 adipocytes [116], neurons [117], endothelial cells [118] and Kaposi's sarcoma cells [119]. Inhibition of IL-6 using an anti-IL6 binding member in disease can therefore lead to a decrease in the basal disease production of IL-6.

Further, anti-IL-6 binding members bind IL-6 in the systemic circulation, in contrast with binding members to IL-6 receptor which need to penetrate the tissue in order to occupy the receptor on the surface of cells involved in the pathology of the disease to be treated.

Binding members to IL-6 may form an equilibrium with IL-6 in the systemic circulation, having the effect of causing gradients across barriers e.g. the synovial membrane, which has the net effect of removing active IL-6 from the joint and forming an inactive complex with the binding member. The consequence of this is that an IL-6 binding member may have quicker onset and dosing regime may be different and potentially easier to optimise, compared with an IL-6R binding member.

IL-6 signalling is mediated by IL-6 binding to IL-6R and that complex binding to gp130. Given that IL-6 and IL-6Ra binding is of nanomolar affinity (about 5 nM) and that IL6:IL6R complex and gp130 binding is of picomolar affinity, a binding member which targets IL-6 faces a lower amount of competition for IL-6 binding and so may suppress a greater proportion of IL-6 signalling. Although this may also apply for a binding member targeting the soluble IL-6Ra and preventing IL-6:IL-6Ra complex formation, if the IL-6Ra is membrane bound then because of steric constraints it may be more difficult for an anti-IL-6Ra to bind and inhibit the IL-6Ra presented on the membrane.

EXAMPLES

Example 1

Lead Isolation 1.1 Selections

Naïve human single chain Fv (scFv) phage display libraries cloned in to a phagemid vector based on the filamentous phage M13 were used for selections [120, 121]). Anti-IL-6 specific scFv antibodies were isolated from the phage display libraries using a series of selection cycles on recombinant human IL-6 essentially as previously described by Vaughan et al [120] and Hawkins et al [122]. In brief, for bio-panning selections, human IL-6 in PBS (Dulbecco's PBS, pH7.4) was adsorbed onto wells of a microtitre plate overnight at 4° C. Wells were washed with PBS then blocked for 1 h with PBS-Marvel (3% w/v). Purified phage in PBS-Marvel (3% w/v) were added to the wells and allowed to bind coated antigen for 1 h. Unbound phage was removed by a series of wash cycles using PBS-Tween (0.1% v/v) and PBS. Bound phage particles were eluted, infected into bacteria and rescued for the next round of selection [120].

1.2 Inhibition of IL-6 Binding to IL-6 Receptor by Crude scFv

A representative number of individual clones from the second round of selections were grown up in 96-well plates. ScFvs were expressed in the bacterial periplasm and screened for their inhibitory activity in a HTRF® (Homogeneous Time-Resolved Fluorescence, CIS Bio international) human IL-6/human IL-6 receptor-binding assay. In this assay, samples competed for binding to cryptate labelled human IL-6 (R&D Systems), with biotinylated IL-6R (Peprotech). A reference anti-IL-6 mAb (Biosource AHC0562) was included in all potency assays as a positive control. The detailed assay method is provided in the Materials and Methods section.

1.3 Reformatting of scFv to IgG1

Clones were converted from scFv to IgG format by sub-cloning the VH and VL domains into vectors expressing whole antibody heavy and light chains respectively. The VH domain was cloned into a vector (pEU15.1) containing the human heavy chain constant domains and regulatory elements to express whole IgG heavy chain in mammalian cells. Similarly, the VL domain was cloned into either vector pEU3.4 for the expression of the human kappa light chain or pEU4.4 for the expression of the human lambda light chain constant domains, with regulatory elements to express whole IgG light chain in mammalian cells. Vectors for the expression of heavy chains and light chains were originally described in ref. [123]. Cambridge Antibody Technology vectors have been engineered simply by introducing an OriP element. To obtain IgGs, the heavy and light chain IgG expressing vectors were transfected into EBNA-HEK293 mammalian cells. IgGs were expressed and secreted into the medium. Harvests were pooled and filtered prior to purification. The IgG was purified using Protein A chromatography.

Culture supernatants are loaded on a column of appropriate size of Ceramic Protein A (BioSepra) and washed with 50 mM Tris-HCl pH 8.0, 250 mM NaCl. Bound IgG was eluted from the column using 0.1 M Sodium Citrate (pH 3.0) and neutralised by the addition of Tris-HCl (pH 9.0). The eluted material was buffer exchanged into PBS using Nap10 columns (Amersham, #17-0854-02) and the concentration of IgG was determined spectrophotometrically using an extinction coefficient based on the amino acid sequence of the IgG [124]. The purified IgG were analysed for aggregation or degradation using SEC-HPLC and by SDS-PAGE.

1.4 Inhibition of IL-6 Binding to IL-6 Receptor by Purified scFv and IgG

ScFv which showed a significant inhibitory effect on the IL-6:IL-6R interaction as crude periplasmic extracts, were subjected to DNA sequencing [120, 125]. Unique scFvs were expressed again in bacteria and purified by affinity chromatography (as described by Bannister et al [126]. Purified IgG samples of these clones were also prepared as described in section 1.3. The potencies of these samples were determined by competing a dilution series of the purified preparation against biotinylated sIL-6R for binding to HIS FLAG tagged human IL-6 (in house *E. coli* derived).

The results for clone CAN022D10, as an scFv and as an IgG having a human heavy chain and kappa light chain constant domain, are given in Table 1. Detailed protocols are provided in Materials and Methods section.

TABLE 1

Potency of CAN022D10 scFv and IgG in the receptor-ligand HTRF biochemical assay

| CLONE | IC50 scFv (nM) | IC50 IgG (nM) |
|---|---|---|
| CAN022D10 | 45 | 0.31 |

1.5 Inhibition of IL-6 Induced Proliferation of TF-1 Cells by Purified scFv and IgG The neutralisation potency of purified scFv preparations against human and cynomolgus IL-6 bioactivity was assessed using TF-1 cell proliferation assay. TF-1 is a human premyeloid cell line established from a patient with erythroleukaemia [134]. The TF-1 cell line is factor dependent for survival and proliferation. TF-1 cells were shown to respond to both human and cynomolgus IL-6 (in-house, *E. coli* derived) and were maintained in media containing human GM-CSF (4 ng/ml, R&D Systems). Inhibition of IL-6 dependent proliferation was determined by measuring the reduction in incorporation of tritiated thymidine into the newly synthesized DNA of dividing cells. A detailed description of the protocol is provided in the Materials and Methods section.

Purified scFv preparations of CAN022D10 were capable of inhibiting the IL-6 induced proliferation of the TF-1 cells at the maximum concentration tested, although complete inhibition was not observed. It was therefore not possible to calculate accurate $IC_{50}$ potency data from the results obtained. When tested as a purified IgG, the $IC_{50}$ for CAN022D10 was calculated as being 93 nM.

1.6 Selectivity and Species Cross Reactivity of Antibodies in DELFIA® Epitope Competition Assays The species cross reactivity and selectivity of antibodies to IL-6 family members was established using DELFIA® epitope competition assays, by measuring inhibition of biotinylated HIS FLAG IL-6 (in-house, *E. coli* derived), binding each immobilised anti-IL-6 antibody.

Titrations of purified, leukaemia inhibitory factor (LIF) (Chemicon), ciliary neurotrophic factor (CNTF), IL-11 and oncostatin M (all R & D Systems) were tested in each assay to establish the potency for each structurally related protein, as measured by $IC_{50}$ values in the assay.

Titrations of IL-6 species including cynomolgus (in house *E. Coli* derived), human HIS FLAG IL-6 (in house HEK-EBNA derived), rat and murine IL-6 (both R & D Systems) were tested in each assay to establish the species cross-reactivity of the antibodies. Example results of this experiment are provided in Table 2. Details of the protocol are provided in the Materials and Methods section.

TABLE 2

Potencies of IL-6 related proteins and different IL-6 species in the CAN22D10 competition assay

| Protein | $IC_{50}$ (nM) |
|---|---|
| Human IL-6 | 32* |
| Cynomolgus IL-6 | 100* |
| Murine IL-6 | No inhibition |
| Rat IL-6 | No inhibition |
| Human IL-11 | No inhibition |
| Human CNTF | No inhibition |
| Human LIF | No inhibition |
| Human Oncostatin M | No inhibition |

*Values are approximations as incomplete curves were obtained for the samples 1.7 Inhibition of Endogenous IL-6 Induced VEGF Release from Human Synovial Fibroblast by Purified IgG Potencies of the antibodies were evaluated for inhibition of IL-6 induced VEGF release from human synovial fibroblasts explanted from donors with rheumatoid arthritis. A detailed protocol for this procedure is provided in Materials and Methods. In brief, titrations of the test IgG were added cultured fibroblasts, which were then stimulated by the addition of human IL-1β and soluble human IL-6Rα to induce IL-6 expression and enable signalling of the cells to induce VEGF expression. Following a 48 h incubation, supernatants were removed and tested by ELISA for the expression of VEGF using a commercially available kit (R & D Systems). These data were used to determine $IC_{50}$ for the CAN022D10, which was calculated as being 45 nM.

Example 2

Antibody Optimisation 2.1 Identification of Amino Acids that May Improve Binding of the Lead Antibody to IL-6

A strategy to identify key residues in the parent antibody sequence that may improve binding to IL-6 was carried out by introducing random mutations throughout the CAN022D10 scFv sequence. This was achieved by two rounds of mutagenesis using A Diversify™ PCR random mutagenesis kit (BD biosciences), following the manufacturers instructions to incorporate on average, 8.1 mutations per kilobase in the nucleic acid sequence per round of mutagenesis. The selections were performed essentially as described previously (Hanes et al 2000; Methods in Enzymology. 328. 404-430). In brief, the random mutagenesis library of the parent clone was transcribed in to mRNA and using a process of stalled translation, mRNA-ribosome-scFv complexes were formed. These complexes were incubated with bio-huIL-6, and those that bound to the antigen were then captured on streptavidin-coated paramagnetic beads. Non-specific ribosome complexes were washed away, and mRNA was isolated from the bound ribosomal complexes, reverse transcribed to cDNA and then amplified by PCR. This DNA was used for the next round of selection and/or cloned out for screening. The selection process was repeated in the presence of decreasing concentrations of bio-huIL-6 (100 nM to 0.1 nM over 4 rounds). ScFv isolated by ribosome display were cloned into the phagemid vector pCANTAB6 by NcoI/NotI restriction endonuclease digestion (New England Biolabs) of the ribosome display construct, followed by ligation in to NcoI/NotI digested pCANTAB6 using T4 DNA ligase (New England Biolabs) [127]. Ligated DNA was then transformed in to chemically competent TG-1 cells, and crude scFv from individual clones were competed against CAN022D10 IgG for binding to HIS/FLAG IL-6 tested in a ligand-antibody biochemical assay.

2.2 Identification of Improved Clones Using an Antibody-Ligand Biochemical Assay (Using CAN022D10 IgG)

Crude scFv preparations from a representative number of individual clones for the round 3 and round 4 outputs were screened for their inhibitory activity in a CAN022D10 IgG-IL-6 HTRF® binding assay. In this assay, binding of biotinyated antibody and FLAG-tagged IL-6 was detected using cryptate labelled anti-FLAG monoclonal antibody and streptavidin XL$^{ent!}$™. The detailed assay method is provided in the Materials and Methods section.

ScFv that demonstrated a significant inhibitory effect were sequenced and produced as purified preparations as described in section 1.4. The $IC_{50}$ value for each scFv was then calculated from data obtained by a testing dilution series of the purified sample in the HTRF antibody-ligand biochemical assay and TF-1 proliferation assay. The most potent clones in the TF-1 proliferation assay were converted to IgG with a heavy chain constant domain and kappa light chain constant domain, as described previously, and were re-tested in the TF-1 proliferation assay. Example potency data for both purified scFv and IgG for each sample is provided in Table 3.

TABLE 3

Examples of clones with improved potencies in the ligand-antibody biochemical and TF-1 proliferation assays, isolated from the ribosome display CAN022D10 random mutagenesis library

| | $IC_{50}$ (pM) | | | |
|---|---|---|---|---|
| | Biochemical Assay | | TF-1 Proliferation Assay | |
| Clone | scFv | IgG* | scFv | IgG |
| Antibody 2 | 35 | 36 | 9600 | 16 |
| Antibody 3 | 22 | 43 | 7300 | 50 |
| Antibody 4 | 24 | 43 | 13400 | 61 |
| Antibody 5 | 65 | 26 | 12400 | 42 |

*Protocol was modified for IgG potency determination so scFv and IgG potencies for each clone should not be directly compared. For details of modifications, see Materials and Methods.

2.3 Optimisation of Parent Clone by Targeted Mutagenesis

Lead antibodies were optimised using a targeted mutagenesis approach using affinity-based phage display selections. For the targeted mutagenesis approach, large scFv-phage libraries derived from the lead clones were created by oligonucleotide-directed mutagenesis of the variable heavy (VH) and light (VL) chain complementarity determining regions 3 (CDR3) using standard molecular biology techniques [128]. The libraries were subjected to affinity-based phage display selections in order to select variants with higher affinity for IL-6. In consequence, these should show an improved inhibitory activity for IL-6 binding its receptor. The selections were performed essentially as described previously [129]. In brief, the scFv phage particles were incubated with recombinant biotinylated human IL-6 in solution (bio-huIL-6, in house *E. coli* derived and modified in house). ScFv-phage bound to antigen were then captured on streptavidin-coated paramagnetic beads (Dynabeads® M 280) following the manufacturer's recommendations. The selected scFv-phage particles were then rescued as described previously [125], and the selection process was repeated in the presence of decreasing concentrations of bio-huIL-6 (50 nM to 0.1 nM over 3 rounds).

Upon completion of 3 rounds of selection, the VH and VL randomised libraries were recombined to form a single library in which clones contained randomly paired individually randomised VH and VL sequences. Selections were then continued as previously described in the presence of decreasing concentrations of bio-huIL-6 (0.1 nM to 0.1 pM over a further 4 rounds).

2.4 Identification of Improved Clones from the Targeted Mutagenesis Using an Antibody-Ligand Biochemical Assay (Using Antibody 5 IgG)

Crude scFv from clones isolated from the targeted mutagenesis selection outputs were tested in an antibody-ligand biochemical assay, essentially as described in section 2.2. For these outputs, the biochemical assay was re-configured to use Antibody 5 IgG. This antibody is an improved variant on CAN02210 with greater potency in the TF-1 proliferation assay. Incorporation of this more potent IgG resulted in the assay that was able to distinguish between clones of higher potency. The protocol for this modified assay was as described for the original antibody-ligand biochemical assay using CAN022D10, with the following changes. Firstly the concentration of HIS FLAG IL-6 used was reduced from 1 nM to 0.5 nM. Secondly, the concentrations of the anti IL-6 antibody and streptavidin XLent!™ were increased from 1 nM and 20 nM to 16 nM and 40 nM respectively. ScFv that demonstrated a significant inhibitory effect were sequenced and produced as purified scFv and IgG, then tested in the TF-1 proliferation assay.

2.5. Inhibition of IL-6 Induced Proliferation of TF-1 Cells by Purified scFv and IgG of Optimised Clones Potencies of the optimised clones were determined using the IL-6 induced TF-1 proliferation assay as previously described. Clones were tested as both purified scFv preparations and as re-formatted IgG. Example results for both scFv and IgG are given in Table 4.

TABLE 4

Example potencies of clones identified from the targeted mutagenesis libraries when tested in the TF-1 cell proliferation assay

| | $IC_{50}$ (pM) | |
|---|---|---|
| Clone (non-germlined) | scFv | IgG |
| Antibody 7 | 11 | 3 |
| Antibody 8 | 419 | 48 |
| Antibody 10 | 549 | 40 |
| Antibody 14 | 448 | 31 |
| Antibody 16 | 154 | 4.9 |
| Antibody 17 | 38 | 16 |
| Antibody 18 | 51 | 30 |
| Antibody 19 | 508 | 68 |
| Antibody 21 | 42 | N.D. |
| Antibody 22 | 41 | N.D. |
| Antibody 23 | 161 | 20 |
| CNTO-328 | N.D. | 74 |

N.D. Not Determined

Clones demonstrated significant inhibitory effect, but accurate $IC_{50}$ values could not be determined from the dilution series of purified scFv.

2.6. Germlining

The amino acid sequences of the VH and VL domains of the optimised anti-IL-6 antibodies were aligned to the known human germline sequences in the VBASE database [130], and the closest germline was identified by sequence similarity. For the $V_H$ domains of the CANDY022D10 antibody lineage the closest germline v segment was Vh3_DP-86_(3-66) and the closest germline j segment was JH2. For the VL domains the closest germline v segment was Vk1_L12 and the closest germline j segment was JK2.

Without considering the Vernier residues [131], which were left unchanged, there were 3 changes in the frameworks of the $V_H$ domains and 4 changes in the $V_L$ domains, all of which were reverted to the closest germline sequence to identically match human antibodies using standard site directed mutagenesis techniques with the appropriate mutagenic primers.

A total of 5 Vernier residues were identified in the scFv sequence of CAN022D10 that were mutated from germline. These were in the heavy chain at Kabat residues 29 (I present instead of V), 69 (M instead of I), 73 (I instead of N) and 78 (V instead of L). A single Vernier mutation was also identified in the light chain sequence at Kabat residue 46 (V instead of L).

Germlined IgG were then re-evaluated in the IL-6 induced TF-1 proliferation assay to confirm there had not been a reduction in potency. Example potencies for germlined (GL) antibodies are provided in Table 5.

TABLE 5

Example potency data for germlined optimised clones when evaluated in the IL-6 induced TF-1 cell proliferation assay

| Clone | $IC_{50}$ (pM) |
|---|---|
| Antibody 7 (GL) | 5 |
| Antibody 10 (GL) | 71 |
| Antibody 17 (GL) | 1 |
| Antibody 18 (GL) | 3 |
| CNTO-328 | 101 |

2.7. Inhibition of Endogenous IL-6 Induced VEGF Release from Human Synovial Fibroblast by Optimised IgG Optimised IgG were tested in the synovial fibroblast VEGF release assay to evaluate potency against endogenously expressed IL-6. This procedure is reviewed in section 1.7 and described in detail in the Materials and Methods section. Example potencies for the IgG tested are given in Table 6a. Mean potency data for the IgG tested are given in Table 6b.

TABLE 6a

Example potency data for optimised clones when evaluated against endogenous IL-6 in the IL-6 induced synovial fibroblast VEGF release assay

| Clone (GL = germlined clones) | $IC_{50}$ (nM) |
|---|---|
| Antibody 2 | 0.59 |
| Antibody 3 | 0.38 |
| Antibody 4 | 0.52 |
| Antibody 5 | 0.70 |
| Antibody 7 (GL) | 0.75 |
| Antibody 10 (GL) | 0.55 |
| Antibody 17 (GL) | 0.57 |
| Antibody 18 (GL) | 0.93 |
| CNTO-328 | 1.31 |

TABLE 6b

Mean potency data for optimised clones when evaluated against endogenous IL-6 in the IL-6 induced synovial fibroblast VEGF release assay

| Clone (GL = germlined clones) | $IC_{50}$ (nM) (95% CI) | n |
|---|---|---|
| Antibody 7 (GL) | 0.78 (0.54-1.11) | 3 |
| Antibody 17 (GL) | 0.57 (0.51-0.64) | 3 |
| Antibody 18 (GL) | 0.67 (0.20-2.25) | 4 |
| CNTO-328 | 1.02 (0.39-2.63) | 4 |

2.8. Selectivity and Species Cross Reactivity of Optimised Antibodies in DELFIA® Epitope Competition Assays Selectivity and species cross reactivity was reevaluated for a panel of clones using the DELFIA® epitope competition assay as previously described (see section 1.6 and Materials and Methods). Human and cynomolgus IL-6 produced overlapping inhibition curves and therefore equivocal $IC_{50}$ values for all IgG tested. No inhibition was observed for murine, rat or dog IL-6 or any of the related human proteins tested against the antibody panel. This data demonstrates that the panel of clones tested are cross reactive to cynomolgus IL-6 but do not bind to murine, rat or dog IL-6, or to the most related human proteins to human IL-6.

2.9 Calculation of Affinity Data for Optimised Clones Using BIAcore

The binding affinity of purified IgG samples of representative antibodies 7 and 18 to human and cynomolgus IL-6 were determined by surface plasmon resonance using a BIAcore 2000 biosensor (BIAcore® AB) essentially as described in ref.[1] In brief, purified antibodies were coupled to the surface of a CM5 sensorchip using an amine coupling kit (BIAcore®) to provide a surface density of between 220-225 Ru. Human and cynomolgus IL-6 at a range of concentrations between 200 nM and 0.2 nM in HBS-EP buffer were passed over the sensor chip surface. The resulting sensorgrams were evaluated using BIA evaluation 3.1 software to provide relative binding data.

The lower limit of affinity measurement range of the BIAcore® 2000 biosensor is approximately 10 pM (BIAcore® 2000 Instrument handbook). From the data obtained, the affinity of the antibodies to both human and cynomolgus IL-6 was below this 10 pM limit, i.e. the antibodies were more potent than could be measured. Accurate affinity measurements were therefore not calculated. The affinities of both antibodies to both IL-6 species using this approach are considered to be less than 10 pM.

2.10 Calculation of Affinity Data for an Optimised Clone Using the TF-1 Cell Proliferation Assay In Vitro The TF-1 assay was used to calculate the affinity of Antibody 18 by use of Schild analysis. An IL-6 standard curve ($7.7 \times 10^{-15}$ M to $3 \times 10^{-9}$ M) was mixed with a range of IgG concentrations ($2.67 \times 10^{-13}$ M to $8.3 \times 10^{-10}$ M) in duplicate. By plotting the Log 10 antibody concentration against the Log 10 dose ratio, the affinity of the IgG was determined. Using this approach the affinity of Antibody 18 (GL) to human IL-6 was calculated as being 0.40 pM (95% CI 0.12 pM-0.69 pM, n=6).

2.11 Antagonist Potency at Human Recombinant IL-6 Using IL-6 Mediated B9 Cell Proliferation In Vitro IL-6 induced B9 cell proliferation was assessed in the presence of Antibody 18 and an isotype control antibody. The effects of a range of concentrations of each antibody ($1 \times 10^{-13}$ M to $1 \times 10^{-9}$ M) were assessed on an IL-6 standard curve (concentration range $1 \times 10^{-14}$ M to $1 \times 10^{-9}$ M). Data points were in duplicate. B9 proliferation was determined after 4 days incubation by reduction of alamar blue (fluorescence method).

Antibody 18 was shown to inhibit IL-6 induced B9 proliferation. The isotype control had no inhibitory effect. Mean data are shown in Table 8.

TABLE 8

Mean Kb values for inhibition of IL-6 induces B9 proliferation

| | Mean $K_b$ pM (95% CI) | n |
|---|---|---|
| Antibody 18 (GL) | 0.3 (0.1-0.5) | 6 |

2.12 Antagonist Potency at Human Recombinant IL-6 Using IL-6 Mediated IgM Release from SKW6.4 cells In Vitro IL-6 induces IgM secretion from the human B lymphoblast cell line SKW 6.4. SKW6.4 cells incubated with a range of IL-6 concentrations ($1 \times 10^{-12}$ M to $3 \times 10^{-8.5}$ M) gave an average [A]50 of 77 pM (n=3) on IgM secretion. The effect of the anti-human IL-6 Antibodies 7, 17 and 18 and an isotype control antibody on IL-6 induced IgM secretion was assessed by observing the inhibition of various antibody concentrations ($1 \times 10^{-12.5}$ M to $1 \times 10^{-8}$ M) in the presence of 100 pM IL-6. IgM secretion was determined after 4 days by anti-human IgM ELISA. Data points were in duplicate.

Antibodies 7, 17 and 18 inhibited IL-6 induced IgM secretion. The isotype control had no inhibitory effect in these assays. Mean data is shown in Table 9.

TABLE 9

Mean inhibition of IgM secretion from SKW6.4 cells

| | Mean IC50 pM | n |
|---|---|---|
| Antibody 7 (GL) | 2.64 | 3 |
| Antibody 17 (GL) | 3.21 | 3 |
| Antibody 18 (GL) | 2.63 | 3 |

Example 3

Epitope Mapping 3.1 Comparison of Anti-IL-6 Antibody Epitope to Known Anti-Human IL-6 Antibodies The epitope of Antibody 18 (GL) was compared with the epitopes of two anti-human IL-6 antibodies B-E8 and cCLB8. Both these antibodies are known to inhibit the binding of IL-6 to IL-6Ra and have been investigated as potential therapeutic agents [5, 31, 34, 37, 133]. To enable comparisons of the epitopes of the three antibodies, a panel of IL-6 mutants were constructed that each contained a single amino acid mutation compared to the wild-type (wt) sequence. The binding of these mutants to the different antibodies was then evaluated in biochemical competition assays. These experiments were based on the biochemical competition assay described in Example 1.6, with changes in the concentrations of antibodies and IL-6 variants where required. Briefly, antibodies were coated on to the surface of a 96-well Nunc Maxisorp immunoassay plate at a concentration of either 2 nM (Antibody 18) or 4 nM (B-E8 and cCLB8) in PBS and incubated overnight at 4° C. After the surface of the wells was blocked using 3% (w/v) BSA in PBS, dilutions of the inhibitors at a concentration range of 200 nM to 10 pM mixed with biotinylated human IL-6 at a final concentration of 0.15 nM were added to the antibody coated wells and allowed to bind. Binding of the biotinylated IL-6 to the antibodies was measured using Europium labelled streptavidin.

By comparing the $IC_{50}$ values obtained for the mutants to unlabelled wild type human IL-6, a ratio of potency could be established for each mutant. Then, by comparing these ratios across the different antibodies, the effects of the individual mutations on the binding of the antibody to the IL-6 molecule could be evaluated. Typical results of these experiments are presented in Table 10 with the experiments being repeated on 2 further occasions.

TABLE 10

$IC_{50}$ and potency ratios of a panel of IL-6 mutants against the anti-human IL-6 antibodies antibody 18, B-E8 and cCLB8

| | IC50 (M) | | | Potency Ratio | | |
|---|---|---|---|---|---|---|
| Mutant | Antibody 18 | CNTO-328 | B-E8 | Antibody 18 | CNTO-328 | B-E8 |
| F102E | 8.41E−08 | 2.80E−09 | 1.58E−08 | 310.951 | 3.021 | 57.246 |
| F106E | 1.43E−09 | No inhibition | 3.31E−09 | 5.283 | — | 11.989 |
| Irrelevant | No inhibition | No inhibition | No inhibition | — | — | — |
| wt IL-6 | 2.70E−10 | 9.26E−10 | 2.76E−10 | 1.000 | 1.000 | 1.000 |
| R207E | No inhibition | 5.13E−09 | No inhibition | — | 7.401 | — |
| Q211A | 3.07E−10 | 1.10E−07 | 8.51E−10 | 1.498 | 158.221 | 3.208 |
| Irrelevant | No inhibition | No inhibition | No inhibition | — | — | — |
| wt IL-6 | 2.05E−10 | 6.93E−10 | 2.65E−10 | 1.000 | 1.000 | 1.000 |
| R58E | 4.79E−10 | 1.73E−09 | 1.57E−08 | 2.009 | 1.682 | 79.083 |
| S204E | 2.57E−08 | 1.90E−09 | 4.83E−10 | 107.754 | 1.848 | 2.434 |
| Irrelevant | No inhibition | No inhibition | No inhibition | — | — | — |
| wt IL-6 | 2.39E−10 | 1.03E−09 | 1.98E−10 | 1.000 | 1.000 | 1.000 |
| E200W | 5.22E−10 | 2.68E−09 | 5.68E−10 | 2.130 | 3.817 | 2.287 |
| R207L | 1.31E−07 | 1.51E−09 | 9.41E−08 | 534.666 | 2.148 | 378.865 |
| wt IL-6 | 2.45E−10 | 7.02E−10 | 2.48E−10 | 1.000 | 1.000 | 1.000 |

The residue numbering in table 10 is for the amino acid sequence of full length human IL-6 (SEQ ID NO: 161).

The results show that the three antibodies have different binding profiles against the panel of IL-6 mutants and therefore bind to different epitopes on the surface of the cytokine. Kalai et al (1997) previously observed that cCLB8 does not recognise the IL-6 mutant F106E. This has been confirmed in our experiments, as it does not inhibit binding of the biotinylated IL-6 to the antibody. In contrast, the IL-6 mutant F106E is only 5-fold less potent than the wt IL-6 in the competition assay using Antibody 18, indicating that it binds strongly to this antibody. A similar result was observed with mutant Q211A, where the potency ratio against antibody 18 was 1.5, compared to 158 for cCLB8. Conversely, mutants F102E, R207E, R207L and S204E were potent inhibitors in the cCLB8 assay but were observed to be considerably less potent than wt IL-6 in the Antibody 18 assay.

Differences in the binding of Antibody 18 and B-E8 were observed with mutants R58E and S204E. The potency ratio for R58E was 2.009 for Antibody 18, compared to 79.083 for B-E8, indicating that this mutation reduces the binding of B-E8 to IL-6. The effect of mutation S204E appears to be specific to Antibody 18 out of the three antibodies tested. As with cCLB8, this mutation has little impact on the potency of IL-6 binding to B-E8, however the mutant is over 100-fold less potent than the wild-type IL-6 in the biochemical assay for Antibody 18.

Example 4

Administration of an Anti-IL-6 Antibody In Vivo 4.1 Effect of Administration of an Anti-IL-6 Antibody on Human Recombinant IL-6-Induced Neutrophil and Haptoglobin Increase in Mice Systemic administration of IL-6 is known to cause a systemic increase in neutrophils and acute phase protein concentrations. An in vivo model was generated where human IL-6 was administered by intra-peritoneal injection into male C57/B/6/J mice and concentrations of neutrophils and the acute phase protein haptoglobin were measured. The ability of Antibody 18 (GL) administered by sub-cutaneous injection to inhibit the responses was measured.

4.2 Haptoglobin Assay

Intra-peritoneal injection of human IL-6 (5.2 nmol/kg, equivalent to 12 mg/kg, b.i.d.) for 7 days resulted in a significant increase in the plasma haptoglobin levels from 0.02±0.01 mg/mL (vehicle controls) to 1.19±0.27 mg/mL in the IL-6 treated group (T-test, $P<0.01$). Whilst the IgG1 isotype control had no effect, Antibody 18 dose-dependently inhibited the response with significant inhibition (ANOVA, $P<0.01$ vs IL-6 alone) being noted at doses of 10.6 nmol/kg (156 mg/kg) and above (FIG. 1).

4.3 Neutrophil Assay

Intra-peritoneal injection of human IL-6 (5.2 nmol/kg, equivalent to 12 mg/kg, b.i.d.) for 7 days resulted in a significant increase in neutrophil count from $1.1\pm0.44\times10^9$ cells/L (vehicle controls) to $2.47\pm0.12\times10^9$ cells/L in the IL-6 treated group (T-test, $P<0.01$). Whilst the IgG1 isotype control had no effect, antibody 18 dose-dependently inhibited the response with significant inhibition (ANOVA, $P<0.01$ vs IL-6 alone) being noted at doses of 1.5 nmol/kg (23 mg/kg) and above.

These results confirm the ability of an anti-IL-6 antibody to inhibit the systemic effects of IL-6 in vivo.

Materials and Methods

Inhibition of IL-6 Binding to IL-6 Receptor by Crude scFv

Selection outputs were screened in receptor-ligand binding HTRF® (Homogeneous Time-Resolved Fluorescence) assay format for inhibition of either, cryptate labelled human IL-6 (R&D Systems 206-IL), or HIS FLAG tagged human IL-6 (in house *E. coli* derived) binding biotinylated IL-6R (Peprotech 200-06 R).

Outputs during lead isolation were screened as undiluted, crude scFv containing periplasmic extracts prepared in: 200 mM hepes buffer pH7.4, 0.5 mM EDTA and 0.5 M sucrose. 8 nM biotinylated human IL-6R was pre-incubated for 30 minutes at room temperature in the dark, with 8 nM streptavidin XL$^{ent!}$™ (CIS Bio International 611SAXLA). All dilutions were done in phosphate buffered saline (PBS) containing 0.4 M potassium fluoride and 0.1% BSA (assay buffer).

After pre-incubation of the reagents, 10 μl of crude scFv sample was added to a 384 well low volume assay plate (Costar 3676). This was followed by the addition of 5 μl of the pre-incubated biotinylated receptor and streptavidin XL$^{ent!}$™ mix, and then 5 of 11.2 nM cryptate labelled human IL-6.

Assay plates were then centrifuged at 1000 rpm at room temperature for 1 min, and incubated for 2 h at room temperature, prior to reading time resolved fluorescence at 620 nm and 665 nm emission wavelengths using an EnVision plate reader (Perkin Elmer).

Inhibition of IL-6 Binding to IL-6 Receptor by Purified scFv and IgG

Purified scFv and IgG from positive clones identified from screening were tested in a HTRF® assay for inhibition of binding of HIS FLAG tagged human IL-6 to biotinylated IL-6R. 8 nM biotinylated human IL-6R was pre-incubated for 30 minutes at room temperature in the dark, with 8 nM streptavidin XL$^{ent!}$™. All dilutions were done in phosphate buffered saline (PBS) containing 0.4 M potassium fluoride and 0.1% BSA (assay buffer).

A titration of the purified sample was used in order to establish the clone potency as measured by $IC_{50}$ values in the assay. After pre-incubation of the reagents, 10 μl of titration of purified scFv sample was added to a 384 well low volume assay plate (Costar 3676). This was followed by the addition of 5 μl of the pre-incubated biotinylated receptor and streptavidin XL$^{ent!}$™ mix. 2 nM HIS FLAG tagged human IL-6 was combined with 1.732 nM anti-flag IgG labelled with cryptate (CIS Bio International 61FG2KLB) and immediately 5 μl of mix was added to assay plate.

Assay plates were then centrifuged at 1000 rpm at room temperature for 1 min, and incubated for 2 h at room temperature, prior to reading time resolved fluorescence at 620 nm and 665 nm emission wavelengths using an EnVision plate reader (Perkin Elmer).

Data Analysis

The following methods were used to analyse data from the HTRF® assays described above.

Data was analysed by calculating % Delta F values for each sample. Delta F was determined according to equation 1.

$$\%\ \text{Delta}\ F = \frac{(\text{sample 665 nm/620 nm ratio value}) - (\text{non-specific control 665 nm/620 nm ratio value})}{(\text{non-specific control 665 nm/620 nm ratio value})} \times 100 \quad \text{Equation 1}$$

% Delta F values were subsequently used to calculate % specific binding as described in equation 2.

$$\% \text{ specific binding} = \frac{\% \text{ Delta } F \text{ of sample}}{\% \text{ Delta } F \text{ of total binding control}} \times 100 \quad \text{Equation 2}$$

$IC_{50}$ values were determined using GraphPad Prism software by curve fitting using a four-parameter logistic equation (Equation 3).

$$Y = \text{Bottom} + (\text{Top} - \text{Bottom})/(1 + 10^{((\text{Log } EC50 - X) * \text{HillSlope})}) \quad \text{Equation 3:}$$

X is the logarithm of concentration. Y is specific binding Y starts at Bottom and goes to Top with a sigmoid shape.

A reference anti-IL-6 mAb (Biosource AHC0562) was included in all assays as a positive control.

Inhibition of IL-6 Induced Proliferation of TF-1 Cells by Purified scFv and IgG

TF-1 cells were a gift from R&D Systems and maintained according to supplied protocols. Assay media comprised RPMI-1640 with GLUTAMAX I (Invitrogen) containing 5% foetal bovine serum (JRH) and 1% sodium pyruvate (Sigma). Prior to each assay, TF-1 cells were pelleted by centrifugation at 300×g for 5 mins, the media removed by aspiration and the cells re-suspended in assay media. This process was repeated twice with cells re-suspended at a final concentration of $5 \times 10^5$ cells/ml in assay media. The cells were plated out using 100 µl/well in a 96 well assay plate. Plates were incubated for 24 hours at 37° C. and 5% $CO_2$ to starve cell of GM-CSF. Test solutions of purified scFv or IgG (in duplicate) were diluted to the desired concentration in assay media. An irrelevant antibody not directed at IL-6 was used as negative control. Recombinant bacterially derived human (R&D) and cynomolgus (in-house) IL-6 was added to a final concentration of either 20 pM (human IL-6) or 100 pM (cynomolgus) when mixed with appropriate test antibody in a total volume of 100 µl/well. The concentration of IL-6 used in the assay was selected as the dose that at final assay concentration gave approximately 80% of maximal proliferative response. All samples were incubated for 30 mins at room temperature. 100 µl of IL-6 and antibody mixture was then added to 100 µl of the cells to give a total assay volume of 200 µl/well. Plates were incubated for 24 hours at 37° C. and 5% $CO_2$, 20 µl of tritiated thymidine (5 µCi/ml) was then added to each assay point and the plates were returned to the incubator for further 24 hours. Cells were harvested on glass fibre filter plates (Perkin Elmer) using a cell harvester. Thymidine incorporation was determined using Packard TopCount microplate liquid scintillation counter. Data was then analysed using Graphpad Prism software.

Method for Time Resolved Fluorescence Assay of Inhibition of Biotinylated Human IL-6 Binding to Immobilised Anti IL-6 Antibodies The specific method used for this assay and for which results are provided in Example 2.6 employed DELFIA® reagents and is set out above. The method is also described more generally below, and is suitable as an assay for determining and/or quantifying binding of other IL-6 forms and related proteins to anti IL-6 MAbs.

In this assay, the anti-IL-6 monoclonal antibody is bound to a solid support, for example being attached to the support via Fc. Polystyrene high protein binding plates, e.g. Nunc Maxisorb plates, may be used as a suitable support.

Coat the anti IL-6 MAb on to plates at 50 µl per well in PBS, overnight at 4° C.

All subsequent steps are performed at room temperature.

Wash plates three times with PBS, containing 0.05% Tween20 (PBST, currently available under Sigma P1379), then block with 300 µl/well PBS containing 3% (w/v) BSA (currently available under Roche Diagnostics, 70129138) for 1 h.

Wash plates three times with PBST.

Prepare inhibitor titrations in PBS containing 3% (w/v) BSA and add to a 'dilution' plate (40 µl/well) followed by 40 µl/well biotinylated IL-6 to give a final concentration of biotinylated IL-6 equivalent to the KD for the protein for the antibody. Transfer 50 µl of the samples from the dilution plate to the corresponding wells in the assay plate Incubate plates for 1 h.

Wash plates three times with PEST then to each well add 50 µl/well of 0.1 µg/ml Europium-labelled streptavidin in 50 mM Tris-HCl, pH 7.5, containing 0.9% NaCl, 0.5% purified BSA, 0.1% Tween20 and 20 µM EDTA and incubate for 1 h.

Wash plates seven times with a wash buffer comprising of 0.05M Tris buffered saline (0.138M NaCl, 0.0027M KCl), 0.05% (v/v) Tween20, pH8.0 (at 25° C.)

To each well, add 50 µl of an enhancement solution, acidified with acetic acid and containing Triton X-100 along with the chelators βNTA and TOPO. The resulting pH shift from alkali to acid causes a rapid dissociation of the europium ions from the streptavidin conjugate. The free Europium ions then form fluorogenic chelates with the available chelators. Water is removed by the presence of TOPO, enabling the chelates to form micelles, prolonging the fluorogenicity of the chelate.

Incubate for 5 min, then measure time resolved fluorescence at a 620 nm emission wavelength. Fluorescence data are converted to % specific binding according to Equation 1. Determine total binding from control wells containing biotinylated huIL-6 but no competitor. Determine non-specific binding from wells containing biotinylated huIL-6 and a 100-fold excess of huIL-6. Fit resultant data to a sigmoidal curve for calculation of $IC_{50}$ values according to Equation 2.

Determination of Antibody Coating and Biotinylated huIL-6 Concentrations for the Biochemical Epitope Competition Assay The concentration of antibody used for coating and the concentration of biotinylated huIL-6 used in the epitope competition assay will depend on the affinity of the interaction of the two reagents and the efficiency of antibody immobilisation.

A standard concentration for antibody coating and the concentration of biotinylated huIL-6 required must therefore be determined for each antibody to be tested.

As a general rule, the final concentration biotinylated huIL-6 used in each assay is equivalent to the KD of the ligand for the corresponding antibody as determined by saturation analysis. The concentration of antibody used for coating should be such that when the biotinylated huIL-6 is added at KD a minimum signal to background ratio of 10:1 is obtained when detected under the competition assay conditions.

Selectivity and Species Cross Reactivity of Antibodies in DELFIA® Epitope Competition Assays Purified IgG were adsorbed onto 96-well Maxisorp microtitre plates (Nunc) in PBS at a concentration which gave a significant signal when biotinylated human IL-6 was added at approximately its estimated Kd for that particular IgG. Excess IgG was washed away with PBS-Tween (0.1% v/v) and the wells were blocked with PBS-Marvel (3% w/v) for 1 h. A dilution series of each of the following competitors was prepared in PBS, starting at a concentration of approximately 200-times the Kd value of the interaction between biotinylated human IL-6 and the respective IgG; Human IL-6, Cynomolgus IL-6, Rat IL-6 (R & D Systems 506-RL/CF), Murine IL-6 (R & D Systems 406-ML/CF), Human CNTF (R & D Systems 257-NT/CF), Human LIF (Chemicon, LIF1010), Human IL-11(R & D Systems 518-IL/CF) Human Oncostatin M (R & D Systems 295-OM/CF) Unbiotinylated human IL-6 was used as a positive control. To this series, an equal volume of biotinylated recombinant human IL-6 at a concentration of approximately 2-fold the Kd was added (resulting in a series starting at a ratio of competitor antigen:biotinylated human IL-6 of approximately 100:1). These mixtures were then transferred onto the blocked IgG and allowed to equilibrate for 1.5 h. Unbound antigen was removed by washing with PBS-Tween (0.1% v/v), while the remaining biotinylated human IL-6 was detected by streptavidin-Europium3+ conjugate (DELFIA® detection, PerkinElmer). Time-resolved fluorescence was measured at 620 nm on an EnVision plate reader (PerkinElmer). Fluorescence data was converted to % specific binding (100% was determined from control wells containing biotinylated human IL-6 but no competitor, 0% was from wells containing biotinylated human IL-6 and a 100-fold excess of unbiotinylated human IL-6). Resultant data were analysed using Prism curve fitting software (Graphpad) to determine IC50 values according to Equation 3.

Method for Time Resolved Fluorescence Assay of Inhibition of Biotinylated Human IL-6 Binding to Immobilised Anti IL-6 Antibodies The specific method used for this assay and for which results are provided in Example 2.8 employed DELFIA® reagents and is set out above. The method is also described more generally below, and is suitable as an assay for determining and/or quantifying binding of other IL-6 forms and related proteins to anti IL-6 MAbs.

In this assay, the anti-IL-6 monoclonal antibody is bound to a solid support, for example being attached to the support via Fc. Polystyrene high protein binding plates, e.g. Nunc Maxisorb plates, may be used as a suitable support.

Coat the anti IL-6 MAb on to plates at 50 µl per well in PBS, overnight at 4° C.

All subsequent steps are performed at room temperature.

Wash plates three times with PBS, containing 0.05% Tween20 (PBST, currently available under Sigma P1379), then block with 300 µl/well PBS containing 3% (w/v) BSA (currently available under Roche Diagnostics, 70129138) for 1 h.

Wash plates three times with PBST.

Prepare inhibitor titrations in PBS containing 3% (w/v) BSA and add to a 'dilution' plate (40 µl/well) followed by 40 µl/well biotinylated IL-6 to give a final concentration of biotinylated IL-6 equivalent to the KD for the protein for the antibody.

Transfer 50 µl of the samples from the dilution plate to the corresponding wells in the assay plate Incubate plates for 1 h.

Wash plates three times with PEST then to each well add 50 µl/well of 0.1 µg/ml Europium-labelled streptavidin in 50 mM Tris-HCl, pH 7.5, containing 0.9% NaCl, 0.5% purified BSA, 0.1% Tween20 and 20 µM EDTA and incubate for 1 h.

Wash plates seven times with a wash buffer comprising of 0.05M Tris buffered saline (0.138M NaCl, 0.0027M KCl), 0.05% (v/v) Tween20, pH8.0 (at 25° C.)

To each well, add 50 µl of an enhancement solution, acidified with acetic acid and containing Triton X-100 along with the chelators βNTA and TOPO. The resulting pH shift from alkali to acid causes a rapid dissociation of the europium ions from the streptavidin conjugate. The free Europium ions then form fluorogenic chelates with the available chelators. Water is removed by the presence of TOPO, enabling the chelates to form micelles, prolonging the fluorogenicity of the chelate.

Incubate for 5 min, then measure time resolved fluorescence at a 620 nm emission wavelength. Fluorescence data are converted to % specific binding according to Equation 1. Determine total binding from control wells containing biotinylated huIL-6 but no competitor. Determine non-specific binding from wells containing biotinylated huIL-6 and a 100-fold excess of huIL-6. Fit resultant data to a sigmoidal curve for calculation of $IC_{50}$ values according to Equation 2.

Determination of Antibody Coating and Biotinylated huIL-6 Concentrations for the Biochemical Epitope Competition Assay The concentration of antibody used for coating and the concentration of biotinylated huIL-6 used in the epitope competition assay will depend on the affinity of the interaction of the two reagents and the efficiency of antibody immobilisation. A standard concentration for antibody coating and the concentration of biotinylated huIL-6 required must therefore be determined for each antibody to be tested.

As a general rule, the final concentration biotinylated huIL-6 used in each assay is equivalent to the KD of the ligand for the corresponding antibody as determined by saturation analysis. The concentration of antibody used for coating should be such that when the biotinylated huIL-6 is added at KD a minimum signal to background ratio of 10:1 is obtained when detected under the competition assay conditions.

Identification of Improved Clones Using an Antibody-Ligand Biochemical Assay

Selection outputs from lead optimisation were screened in epitope competition HTRF® assay format for inhibition of HIS FLAG tagged human IL-6 (in house *E. coli* derived) binding biotinylated anti IL-6 antibody (in house IgG derived from lead isolation, CAN022D10).

Outputs during lead optimisation were screened as undiluted, crude scFv containing periplasmic extracts prepared in; 50 nM MOPS buffer pH7.4, 0.5 mM EDTA and 0.5M Sorbitol. 1 nM human HIS FLAG IL-6 was pre-incubated for 30 minutes at room temperature in the dark, with 1.732 nM anti-flag IgG labelled with cryptate (CIS Bio International 61FG2KLB). All dilutions were performed in assay buffer. In parallel, 1 nM of biotinylated anti-IL-6 IgG (against which competition of a test binding member was to be tested) was pre-incubated for 30 minutes at room temperature in the dark with 20 nM of streptavidin $XL^{ent'}$™ (CIS Bio International 611SAXLB).

After pre-incubation of reagents, 10 µl of crude scFv sample was added to a black 384 well optiplate (Perkin Elmer Cat No. 6007279). This was followed by addition of 10 µl assay buffer to the whole plate. Then 10 µl of the pre-incubated biotinylated anti-IL-6 IgG and Streptavidin $XL^{ent'}$# mix, and 10 µl of pre-incubated HIS FLAG tagged human IL-6 anti-flag cryptate mix were added.

Assay plates were then centrifuged at 1000 rpm at room temperature for 1 min, and incubated for 2 h at room temperature, prior to reading time resolved fluorescence at 620 nm and 665 nm emission wavelengths using an EnVision plate reader (Perkin Elmer). Data was analysed by calculating % deltaF and % specific binding as previously described.

Following identification of improved leads from the random mutagenesis library, undiluted crude scFv outputs from CDR3 targeted mutagenesis selections were screened in a modified version of the epitope competition HTRF® assay which included the following changes 0.5 nM human HIS FLAG IL-6 was pre-incubated for 30 minutes at room temperature in the dark, with 1.732 nM anti-flag IgG labelled with cryptate (CIS Bio International 61FG2KLB). In parallel, 16 nM of biotinylated anti-IL-6 IgG (Antibody 5, in house IgG identified from CAN022D10 random mutagenesis selections) was pre-incubated for 30 minutes at room temperature in the dark with 40 nM of streptavidin XL$^{ent!}$™ (CIS Bio International 611SAXLB). All other conditions were as described for CAN022D10 epitope competition assay. Data were analysed by calculating % deltaF and % specific binding as previously described.

Inhibition of Endogenous IL-6 Induced VEGF Release from Human Synovial Fibroblasts by Purified IgG Samples of rheumatoid arthritis knees from total joint replacement surgery were obtained in DMEM containing antibiotics. Synovium bathed in media was dissected from the joint & finely chopped. The synovial tissue was washed with media supplemented with 10% FCS. The cell suspension was incubated in a collagenase solution for 2 hours in a $CO_2$ incubator at 37° C. The digested synovial cell suspension was disrupted by repeatedly aspirating through a 10 ml pipette, cell strained & centrifuged at 400 g at room temperature for 5 minutes. The cells were resuspended in DMEM containing 10% FCS, passed through a cell strainer, adjusted to $1\times10^6$ cells per ml & incubated in a $CO_2$ incubator at 37° C. in 225-cm$^2$ cell culture flasks (3001, CoStar Corning Inc.). Following adherence, the majority of the medium was discarded, replaced with fresh & returned to the incubator for long-term incubation. The cells were examined on a weekly-basis & were passaged at confluence by trypsinisation at a passage rate of 1 in 3.

Fibroblasts (P3-5) at confluence were removed from flasks by incubating with 10 mL 0.1% trypsin-EDTA solution (25300-054, Gibco Life Sciences) per flask for 5 to 10 minutes at 37° C. An equal volume of DMEM-based culture medium supplemented with 10% FCS was added to the cells, which were then pelleted by centrifugation at 330 g for 5 minutes at RT. After one wash step with DMEM-based culture medium supplemented with 10% FCS, the cell suspension ($1\times10^5$ cells per mL) was added (150 µL per well) to wells of sterile 96 well cell culture cluster flat bottom polystyrene plates (3598, Corning CoStar) at $1.5\times10^4$ cells per well. A further addition of DMEM-based culture media supplemented with 10% FCS was added to each well (100 µL per well) to give a total volume of 250 µL per well. The cells were incubated at 37° C. overnight to allow for adherence and quiescence.

The 96-well plates were inspected to ensure that the cells were confluent and in good condition (e.g. contamination-free). Medium was then aspirated from the wells and 100 µL of DMEM-based culture medium supplemented with 10% FCS was immediately added. To this, 50 µL of DMEM-based culture medium supplemented with 10% FCS containing either sample IgG or medium alone was added to the wells (diluted 1 in 5 into assay).

This was followed by adding 50 µL per well of DMEM-based culture medium supplemented with 10% FCS containing recombinant human soluble (rhs)IL-6Rα (500 ng per mL; 12 nM) and rhIL-1β (50 pg per mL; 2.95 pM, diluted 1 in 5 into assay).

In separate wells, 50 µL of DMEM-based culture medium supplemented with 10% FCS containing either; rh-IL-6 (0, 100 ng per mL; 21.5 nM), sIL-6Rα (500 ng per mL; 12 nM), rhIL-1β (50 pg per mL; 2.95 pM), or medium alone was added (diluted 1 in 5 into assay). Final volume in each well was 250 µL.

The plates were incubated for 48 hours at 37° C. Incubations were performed in duplicate or triplicate wells as described in the plate format. The plates were centrifuged at 330 g for 5 minutes at RT and supernatant media was removed and stored at −40° C. in microtitre flat bottom plates (611F96, Sterilin).

VEGF was measured using an ELISA (DY293B, R&D Systems) following the manufacturers instructions. Briefly, ELISA plates were coated with a mouse anti-human VEGF antibody overnight at 4° C. and blocked with 1% BSA/PBS. Plates were washed with 0.05% Tween 20/PBS and incubated with culture supernatants of human synovial derived fibroblasts and a biotinylated goat anti-human VEGF antibody over night at room temperature. After washing, VEGF was detected by using Streptavidin horseradish peroxidase. Plates were developed using 1:1 $H_2O_2$:tetramethylbenzidine. The reaction was stopped with 2 M $H_2SO_4$, and optical densities were determined at 450 nm with the correction wavelength set at 540 nm.

BIAcore Measurements

BIAcore® studies were undertaken using a BIAcore® 2000. Antibodies were coupled to the surface of a CM-5 sensorchip using an amine coupling kit to provide a surface density of 220-225 Ru. Human IL-6 at a range of concentrations between 200 nM and 0.2 nM in HBS-EP buffer were passed over the sensor chip surface. The resulting sensorgrams were evaluated using BIA evaluation 3.1 software to calculate the $k_{on}$, $k_{off}$ and $K_D$ values for the antibodies tested.

IL-6 Mediated B9 Cell Proliferation Assay

B9 cells are a sub-clone of the murine B-cell hybridoma cell line, B13.29, selected on the basis of their specific response to IL-6.

B9 cells require IL-6 for survival and proliferation and respond to very low concentrations of IL-6.

IL-6 induced B9 cell proliferation was assessed in the presence of Antibody 18 and an isotype control (CAT-002). The effects of a range of concentrations of each antibody ($1\times10^{-13}$ M to $1\times10^{-9}$ M) were assessed on an IL-6 standard curve (concentration range $1\times10^{-14}$ M to $1\times10^{-9}$ M). Data points were in duplicate. B9 proliferation was determined after 4 days incubation by reduction of alamar blue (fluorescence method).

B9 cells were cultured in RPMI-1640 containing 5% FCS, 2 mM L-Glutamine and 50 µM 2-mercaptoethanol. Cells were split every 2 to 4 days to a density of between $0.05\times10^6$ mL$^{-1}$ and $0.1\times10^6$ mL$^{-1}$ and supplemented with $5\times10^{-13}$M human IL-6. Cells used for experiments were not supplemented with IL-6 for at least 48 hours prior to experiment but had been supplemented within 96 hours of experiment. Cells used in the assay were taken from a stock flask with a density of no greater than $0.8\times10^6$ mL$^{-1}$.

Each antibody was diluted from stock solutions to 10× the maximum required assay concentration by appropriate dilutions in assay media (RPMI+5% FCS, 2 mM L-Glutamine, 50 pM 2-mercaptoethanol, penicillin 100 UmL$^{-1}$ and streptomycin 100 mgmL$^{-1}$). Further 10 fold dilutions in culture media were carried out to obtain the required concentrations of each antibody.

IL-6 was reconstituted from a lyophilised powder to a $1\times10^{-5}$ M solution by addition of an appropriate volume of sterile PBS+0.1% BSA. A further dilution to $1\times10^{-9}$ M was carried out in culture media. $1\times10^{-8}$ M aliquots were stored frozen until required. On the day of assay $1\times10^{-9}$ M aliquots were diluted as necessary to achieve the range of solutions at 10× final assay concentration required.

The required volume of cells was removed from culture flasks and centrifuged at 300 g for 8 minutes. Supernatants were removed and the cells re-suspended in an appropriate volume of culture media to achieve a cell density of $0.5 \times 10^6$ mL$^{-1}$.

Assays were performed in flat-bottomed, tissue culture treated, polystyrene 96 well plates. The final assay volume was 200 µL. 20 µL of 10× antibody (Antibody 18 or CAT-002) solution or culture media was added to the appropriate wells of each plate followed by a further 140 µL of culture media and 20 µL of the appropriate concentration of IL-6 or culture media.

Plates were placed in a humidified 5% $CO_2$, 37° C. incubator for 2 hours. 20 µL of cells was then added to each well. Final number of cells per well was 10000. Plates were then returned to the incubator for 4 days. Cell proliferation was assessed by incorporation of alamar blue. 10% v/v alamar blue was added to each well and the plates returned to the incubator for 6 hours. Plates were then read on a spectrofluorimeter measuring fluorescence at 590 nm following excitation at 544 nm Raw data were normalised to the control IL-6 curve on the each plate such that maximum fluorescence was defined as 100% and the basal fluorescence 0%. Normalised data was fitted using the non-linear regression, sigmoidal dose-response (variable slope) fitting programme in Graph Pad Prism 4.01. Control p$EC_{50}$ values and p$EC_{50}$ values in the presence of each concentration of antibody were used to determine dose ratios (DR). $K_b$ values were determined for the lowest concentration of antibody which elicited a 3-fold or greater shift in the IL-6 concentration-effect curve using the chemical antagonism equation below:

$$K_b = ([Ab]/(DR-1))$$

(Kenakin T P. In: Pharmacologic Analysis of Drug-Receptor Interactions. 1st ed. New York: Raven Press; 1987. p. 205-24.)

IL-6 Mediated SKW6.4 Cell IgM Release Assay

IL-6 is involved in the final maturation of B cells into antibody producing cells (B-lymphocyte differentiation). SKW cells have been used previously for the study of B cell responses (Nawata et al., Ann. N.Y. Acad. Sci. 557:230-238. 1989). Auto-antibody production in rheumatoid arthritis is mostly of the IgM class. SKW6.4 is a clonal IgM secreting human lymphoblastoid B cell line. Cells were sourced from ATCC, reference #TIB 215. Upon stimulation with IL-6 these cells secrete IgM, thus this assay was perceived to be relevant to rheumatoid arthritis.

IL-6 induced SKW6.4 cell IgM secretion was assessed in the presence of CAT6001 and CAT-002 (isotype control). The effects of a range of concentrations of each antibody ($1 \times 10^{-12.5}$ M to $1 \times 10^{-8}$ M) were assessed in the presence of 100 pM IL-6. Data points were in duplicate. IgM secretion in the cell supernatants was determined after 4 days incubation using anti-human IgM ELISA assay.

SKW 6.4 cells were cultured in RPMI1640 containing 2 mM L-Glutamine and 10% (v/v) foetal calf serum at 37° C. at 95/5% (v/v) air/$CO_2$ in 95% relative humidity. The cells were maintained between 0.4 and $2 \times 10^6$ cells/ml. For routine cell passage, cells were harvested by centrifugation at 300×g for 5 minutes at room temperature, spent medium was removed and the cells re-suspended in the required volume of fresh media.

Each antibody was diluted from stock solutions to 50× the maximum required assay concentration by appropriate dilutions in assay media (RPMI+10% FCS, 2 mM L-Glutamine).

Further 10 fold dilutions in culture media were carried out to obtain the required concentrations of each antibody.

Assays were performed in flat-bottomed, tissue culture treated, polystyrene 96 well plates. SKW 6.4 cell stocks were diluted to a cell density of $0.3 \times 10^6$ ml$^{-1}$ in fresh media, and plated at 100 µl/well, (30,000 cells per well). 2 µl of antibody, at the indicated final concentration, followed by 2 µl of IL-6 at a final concentration of 100 pM was then added to each well.

Plates were then returned to the incubator at 37° C. 5% $CO_2$. Cell-free supernatants were harvested after 4 days incubation by centrifugation and then either assayed by IgM ELISA on the day of harvest or frozen at −20° C. prior to further analysis.

An ELISA was generated using a pair of antibodies from Serotec. The coating antibody was Mouse anti-human IgM (MCA1662) and the detection antibody was Goat anti-human IgM: HRP linked (STAR98P). The assay was optimised by standard methods to give a good signal to noise ratio using coating antibody @ 1:2000 dilution (5 µg/ml) and detection antibody @ 1:3500 dilution (200 ng/ml).

IgM standard solution (Cat# PHP003 Human M Kappa purified protein) was purchased from Serotec to generate a standard curve.

Data was analysed using a polynomial fit for the IgM standard curve data using a standard fitting programme. The percentage inhibition of each antibody sample against the control IgM production in the absence of antibody was calculated and $IC_{50}$ values were generated.

Generation of IL-6 and IL-6 Mutant Proteins for Epitope Mapping

Cloning of Human and Cyno IL-6 cDNA

The sequences of human and macaque IL-6 were obtained from Embl (Accession No: BC015511 and AB000554 for human and cyno respectively). Using these sequences oligonucleotide primers were designed to amplify the cDNA encoding human & macaque IL-6. The N-terminal primers were hIL6__5'NdeI and macIL6__5'NdeI for human and cyno respectively and macIL6__3'NheI was used as the C terminal primer for both (See Table 11 for oligonucleotides sequences).

TABLE 11

Primer sequences

| Primer | Sequence |
|---|---|
| macIL6_<br>5'NdeI | 5' TTATCAT-ATGGTACTCCCAGGAGAAGATTCCAA 3'<br>(SEQ ID NO: 183) |
| macIL6_<br>3'NheI | 5' TTATGCTAGC-CTACATTTGCCGAAGAGCCC 3'<br>(SEQ ID NO: 184) |
| hIL6_5'NdeI | 5' TTATACATATG-GTACCCCAGGAGAAGATTCC 3'<br>(SEQ ID NO: 185) |

PCVR reactions to amplify the two cDNAs were carried out. The template for each PCR reaction was 10 ng of cDNA obtained from human Liver and cynomolgus liver respectively. The amplified cDNA from each reaction was purified and cloned into pCR4blunt topo (Invitrogen) using the topoisomerase ligation reaction according to the manufacturer.

Positive clones were identified and sequenced. The resulting cDNAs were sub-cloned using standard techniques into various E. coli T7-promoter expression vectors in such a way that the cDNA encoding mature human or cynomolgus IL-6 were fused at the N-terminus with either an N-terminal HIS6-FLAG tag immediately upstream of the N-terminal valine of mature IL-6.

Generating Mutants

Site directed mutagenesis was performed using a Quikchange XL kit from Stratagene according to the manufacturer's protocol. Mutagenesis primer design was performed according to the manufacturer's protocol. Mutagenesis reactions were carried out according to the protocol using plasmid pT7flagHISIL-6 as template. This was followed by subsequent DpnI digestion and transformation into chemically competent Top10 cells with selection on agar plates containing appropriate antibiotics at 37° C. overnight. For each individual mutagenesis reaction several clones were sequenced and plasmid DNA of one correct clone from each reaction was retained for further use.

Expression of IL-6 and IL-6 Mutant Proteins

The IL-6 expression plasmids were transformed into chemically competent BL21 (DE3) star cells (Invitrogen) using the manufacturer's method. Transformed cells were used to inoculate 1 L cultures of Terrific Broth and these were incubated on an orbital incubator at 37° C., until the A600 reached 0.5. IPTG was then added to 0.25 mM and incubation continued overnight at 22° C. The cells were harvested by centrifugation and the cell pellets were stored at −80° C.

Purification of IL-6 and IL-6 Mutant Proteins

The cell pellets were thawed and resuspended in 50 ml per pellet of 50 mM potassium phosphate, pH7.4, 10 mM imidazole, 0.3M NaCl, 5 mM beta-mercaptoethanol, 10% glycerol (buffer A)+Complete EDTA-free protease inhibitors (Roche). The cells were lysed by sonication for 3×30 seconds on ice. The lysate was centrifuged at 100,000 g and 4° C. for 30 minutes and the supernatant was subjected to Ni NTA affinity chromatography. A 5 ml column of Ni-NTA Superflow (Qiagen) was equilibrated at 3 ml/min with (buffer A). The IL-6 sample was loaded and the column was washed with 10 column volumes of 15 mM imidazole in buffer A. This was followed by a 10 column volume wash with 30 mM imidazole in buffer A. IL-6 was eluted from the column using a 5 column volume wash in the upward flow direction with 0.3M imidazole in buffer A. 10 ml fractions were collected during the wash steps and 5 ml fractions were collected during the elution step. The column was run at 4° C. using the AKTA Explorer100 Air. Fractions containing the purified IL-6 protein were pooled and dialysed overnight at 4° C. against 5 L of PBS.

The dialysed IL-6 proteins were further purified using gel filtration chromatography. For each purification the dialysed IL-6 protein was centrifuged at 100,000 g and 4° C. for 20 minutes. Up to 13 ml was applied to a 318 ml Superdex 200 26/60 column (GE Healthcare) that had been equilibrated in PBS at 2.5 ml/min. The column was run at 4° C. using an AKTA Purifier. Fractions containing the monomeric IL-6 protein peak were pooled for further analysis.

Each protein was checked for purity using standard SDS-chromatography, the protein concentration was measured and Q-ToF mass spectroscopy was used to measure the mass of the protein. Purified IL-6 was frozen in liquid nitrogen and stored at −80° C.

Materials and Methods for In Vivo Studies

Animals were randomly assigned to into test groups. The mice in each test group were then treated daily with set sub-cutaneous doses (10 ml/kg) of either vehicle control (0.05% BSA in PBS) or 467 µg/kg IgG1 isotype control or antibody 18 (range from 467 µg/kg to 8 µg/kg). At the same time the mice were given an intra-peritoneal injection (10 ml/kg) b.i.d. of either vehicle control (0.05% BSA in PBS) or 12 µg/kg human recombinant IL-6.

On day 7, two hours following the final IL-6 dose at 09:00 h, the mice were sacrificed and terminal blood samples were taken. The blood was transferred to Lab Tek 1 ml EDTA blood tubes, which were placed on a roller for 5 minutes. Samples were then kept on ice until used. Differential cell counts were performed using a Sysmex cell counter. The remainder of the sample was transferred to an eppendorf tube and spun (300 g, 5 mins) to obtain plasma which was sub aliquoted and stored at −20° C. until anlaysed for Haptoglobin levels.

The haptoglobin assay was carried out as per instructions provided in the PHASE™ RANGE TriDelta Format kit by Biognosis (Hailsham, UK; cat. no. TP-801).

All results were expressed as mean±SEM. Data analysis was by unpaired T-test or one-way ANOVA followed by Dunnett's test (GraphPad Instat).

Sequences

VH domain, VL domain and CDR sequences of binding members are shown in the appended sequence listing, in which SEQ ID NOS correspond as follows:

| | |
|---|---|
| 1 | CAN022D10 VH nucleotide |
| 2 | CAN022D10 VH amino acid |
| 3 | CAN022D10 VH CDR 1 aa |
| 4 | CAN022D10 VH CDR 2 aa |
| 5 | CAN022D10 VH CDR 3 aa |
| 6 | CAN022D10 VL nucleotide |
| 7 | CAN022D10 VL amino acid |
| 8 | CAN022D10 VL CDR 1 aa |
| 9 | CAN022D10 VL CDR 2 aa |
| 10 | CAN022D10 VL CDR 3 aa |
| 11 | Antibody 2 VH nucleotide |
| 12 | Ab 2 VH amino acid |
| 13 | Ab 2 VH CDR 1 amino acid |
| 14 | Ab 2 VH CDR 2 amino acid |
| 15 | Ab 2 VH CDR 3 amino acid |
| 16 | Ab 2 VL nucleotide |
| 17 | Ab 2 VL amino acid |
| 18 | Ab 2 VL CDR 1 amino acid |
| 19 | Ab 2 VL CDR 2 amino acid |
| 20 | Ab 2 VL CDR 3 amino acid |
| 21 | Antibody 3 VH nucleotide |
| 22 | Ab 3 VH amino acid |
| 23 | Ab 3 VH CDR 1 amino acid |
| 24 | Ab 3 VH CDR 2 amino acid |
| 25 | Ab 3 VH CDR 3 amino acid |
| 26 | Ab 3 VL nucleotide |
| 27 | Ab 3 VL amino acid |
| 28 | Ab 3 VL CDR 1 amino acid |
| 29 | Ab 3 VL CDR 2 amino acid |
| 30 | Ab 3 VL CDR 3 amino acid |
| 31 | Antibody 4 VH nucleotide |
| 32 | Ab 4 VH amino acid |
| 33 | Ab 4 VH CDR 1 amino acid |
| 34 | Ab 4 VH CDR 2 amino acid |
| 35 | Ab 4 VH CDR 3 amino acid |
| 36 | Ab 4 VL nucleotide |
| 37 | Ab 4 VL amino acid |
| 38 | Ab 4 VL CDR 1 amino acid |
| 39 | Ab 4 VL CDR 2 amino acid |
| 40 | Ab 4 VL CDR 3 amino acid |
| 41 | Antibody 5 VH nucleotide |
| 42 | Ab 5 VH amino acid |
| 43 | Ab 5 VH CDR 1 amino acid |
| 44 | Ab 5 VH CDR 2 amino acid |
| 45 | Ab 5 VH CDR 3 amino acid |
| 46 | Ab 5 VL nucleotide |
| 47 | Ab 5 VL amino acid |
| 48 | Ab 5 VL CDR 1 amino acid |
| 49 | Ab 5 VL CDR 2 amino acid |
| 50 | Ab 5 VL CDR 3 amino acid |
| 51 | Antibody 7 VH nucleotide |
| 52 | Ab 7 VH amino acid |
| 53 | Ab 7 VH CDR 1 amino acid |
| 54 | Ab 7 VH CDR 2 amino acid |
| 55 | Ab 7 VH CDR 3 amino acid |
| 56 | Ab 7 VL nucleotide |
| 57 | Ab 7 VL amino acid |
| 58 | Ab 7 VL CDR 1 amino acid |

| | |
|---|---|
| 59 | Ab 7 VL CDR 2 amino acid |
| 60 | Ab 7 VL CDR 3 amino acid |
| 61 | Antibody 8 VH nucleotide |
| 62 | Ab 8 VH amino acid |
| 63 | Ab 8 VH CDR 1 amino acid |
| 64 | Ab 8 VH CDR 2 amino acid |
| 65 | Ab 8 VH CDR 3 amino acid |
| 66 | Ab 8 VL nucleotide |
| 67 | Ab 8 VL amino acid |
| 68 | Ab 8 VL CDR 1 amino acid |
| 69 | Ab 8 VL CDR 2 amino acid |
| 70 | Ab 8 VL CDR 3 amino acid |
| 71 | Antibody 10 VH nucleotide |
| 72 | Ab 10 VH amino acid |
| 73 | Ab 10 VH CDR 1 amino acid |
| 74 | Ab 10 VH CDR 2 amino acid |
| 75 | Ab 10 VH CDR 3 amino acid |
| 76 | Ab 10 VL nucleotide |
| 77 | Ab 10 VL amino acid |
| 78 | Ab 10 VL CDR 1 amino acid |
| 79 | Ab 10 VL CDR 2 amino acid |
| 80 | Ab 10 VL CDR 3 amino acid |
| 81 | Antibody 14 VH nucleotide |
| 82 | Ab 14 VH amino acid |
| 83 | Ab 14 VH CDR 1 amino acid |
| 84 | Ab 14 VH CDR 2 amino acid |
| 85 | Ab 14 VH CDR 3 amino acid |
| 86 | Ab 14 VL nucleotide |
| 87 | Ab 14 VL amino acid |
| 88 | Ab 14 VL CDR 1 amino acid |
| 89 | Ab 14 VL CDR 2 amino acid |
| 90 | Ab 14 VL CDR 3 amino acid |
| 91 | Antibody 16 VH nucleotide |
| 92 | Ab 16 VH amino acid |
| 93 | Ab 16 VH CDR 1 amino acid |
| 94 | Ab 16 VH CDR 2 amino acid |
| 95 | Ab 16 VH CDR 3 amino acid |
| 96 | Ab 16 VL nucleotide |
| 97 | Ab 16 VL amino acid |
| 98 | Ab 16 VL CDR 1 amino acid |
| 99 | Ab 16 VL CDR 2 amino acid |
| 100 | Ab 16 VL CDR 3 amino acid |
| 101 | Antibody 17 VH nucleotide |
| 102 | Ab 17 VH amino acid |
| 103 | Ab 17 VH CDR 1 amino acid |
| 104 | Ab 17 VH CDR 2 amino acid |
| 105 | Ab 17 VH CDR 3 amino acid |
| 106 | Ab 17 VL nucleotide |
| 107 | Ab 17 VL amino acid |
| 108 | Ab 17 VL CDR 1 amino acid |
| 109 | Ab 17 VL CDR 2 amino acid |
| 110 | Ab 17 VL CDR 3 amino acid |
| 111 | Antibody 18 VH nucleotide |
| 112 | Ab 18 VH amino acid |
| 113 | Ab 18 VH CDR 1 amino acid |
| 114 | Ab 18 VH CDR 2 amino acid |
| 115 | Ab 18 VH CDR 3 amino acid |
| 116 | Ab 18 VL nucleotide |
| 117 | Ab 18 VL amino acid |
| 118 | Ab 18 VL CDR 1 amino acid |
| 119 | Ab 18 VL CDR 2 amino acid |
| 120 | Ab 18 VL CDR 3 amino acid |
| 121 | Antibody 19 VH nucleotide |
| 122 | Ab 19 VH amino acid |
| 123 | Ab 19 VH CDR 1 amino acid |
| 124 | Ab 19 VH CDR 2 amino acid |
| 125 | Ab 19 VH CDR 3 amino acid |
| 126 | Ab 19 VL nucleotide |
| 127 | Ab 19 VL amino acid |
| 128 | Ab 19 VL CDR 1 amino acid |
| 129 | Ab 19 VL CDR 2 amino acid |
| 130 | Ab 19 VL CDR 3 amino acid |
| 131 | Antibody 21 VH nucleotide |
| 132 | Ab 21 VH amino acid |
| 133 | Ab 21 VH CDR 1 amino acid |
| 134 | Ab 21 VH CDR 2 amino acid |
| 135 | Ab 21 VH CDR 3 amino acid |
| 136 | Ab 21 VL nucleotide |
| 137 | Ab 21 VL amino acid |
| 138 | Ab 21 VL CDR 1 amino acid |
| 139 | Ab 21 VL CDR 2 amino acid |
| 140 | Ab 21 VL CDR 3 amino acid |
| 141 | Antibody 22 VH nucleotide |
| 142 | Ab 22 VH amino acid |
| 143 | Ab 22 VH CDR 1 amino acid |
| 144 | Ab 22 VH CDR 2 amino acid |
| 145 | Ab 22 VH CDR 3 amino acid |
| 146 | Ab 22 VL nucleotide |
| 147 | Ab 22 VL amino acid |
| 148 | Ab 22 VL CDR 1 amino acid |
| 149 | Ab 22 VL CDR 2 amino acid |
| 150 | Ab 22 VL CDR 3 amino acid |
| 151 | Antibody 23 VH nucleotide |
| 152 | Ab 23 VH amino acid |
| 153 | Ab 23 VH CDR 1 amino acid |
| 154 | Ab 23 VH CDR 2 amino acid |
| 155 | Ab 23 VH CDR 3 amino acid |
| 156 | Ab 23 VL nucleotide |
| 157 | Ab 23 VL amino acid |
| 158 | Ab 23 VL CDR 1 amino acid |
| 159 | Ab 23 VL CDR 2 amino acid |
| 160 | Ab 23 VL CDR 3 amino acid |
| 161 | Full length human IL-6 amino acid |
| 162 | HIS FLAG tagged human IL-6 |
| 163 | Soluble IL-6Ra (human) |
| 164 | Transmembrane IL-6Ra (human) |
| 165 | Mature human IL-6 amino acid |
| 166 | Human gp130 |
| 167 | Germlined VH FR1 |
| 168 | Germlined VH FR2 |
| 169 | Germlined VH FR3 |
| 170 | Germlined VH FR4 |
| 171 | Germlined VL FR1 |
| 172 | Germlined VL FR1 |
| 173 | Germlined VL FR1 |
| 174 | Germlined VL FR1 |
| 175 | F102E mutant IL-6 |
| 176 | S204E mutant IL-6 |
| 177 | R207E mutant IL-6 |
| 178 | F106E mutant IL-6 |
| 179 | Q211A mutant IL-6 |
| 180 | R58E mutant IL-6 |
| 181 | E200W mutant IL-6 |
| 182 | R207L mutant IL-6 |
| 183 | primer macIL6_5'NdeI |
| 184 | primer macIL6_3'NheI |
| 185 | primer hIL6_5'NdeI |

Sequences of antibodies 7, 10, 17 and 18 are germlined.

REFERENCES

All references cited anywhere in this specification, including those cited anywhere above, are incorporated herein by reference in their entirety and for all purposes.

1 Kishimoto, T., (1989) Blood 74:1-10
2 Smith P. C. et al. (2001) Cytokine and Growth factor Reviews 12:33-40
3 Wallenius et al., (2002) Nat. Med. 8:75
4 Kawano et al. (1988) Nature 332:83
5 Van Zaanen et al. (1996) J. Clin Invest. 98:1441-1448
6 Somers, W., et al (1997) 1.9 EMBO J. 16:989-997
7 Jones, S. A et al. (2001) FASEB J. 15:43-58
8 Varghese et al. (2002) PNAS USA 99:15959-15964
9 Boulanger et al (2003) Science 300:2101-2104
10 Menziani et al (1997) Proteins: Structure Function and Genetics 29, 528
11 Brakenhoff et al. (1990) J. Immunol. 145:561-568
12 Wijdenes et al. (1991) Mol Immunol. 28:1183-1191
13 Brakenhoff et al. (1994) JBC 269:86
14 Kalai et al. (1996) Eur J Biochem 238 714-723
15 Kalai et al. (1997) Blood 89:1319-1333
16 Hirata et al. (1989) J. Immunol 143:2900-2906

17 Kalai et al. (1997) Eur J. Biochem 249:690-700
18 Ernst, M. and B. J. Jenkins. (2004) Trends Genet. 20:23-32
19 Yoshida, K. et al (1996) PNAS USA 93:407-411
20 Heinrich, P. C. et al. (2003) Biochem. J. 374:1-20
21 Choy, E. (2004) Rheum. Dis. Clin. North Am. 30:405-415
22 Jones S A et al. (2001) FASEB J 15:43-58
23 Kishimoto (2006) Arthritis Research & Therapy 8:Supp 2/S2
24 Hirano T et al. (1986) Nature 324:73-76
25 Moshage (1997) J. Pathol. 181:257-266
26 Guillen, C. et al. (2004) Calcif. Tissue Int. 75:153-159
27 Tamura, T., et al. (1993) PNAS USA 90:11924-11928
28 Udagawa, N et al. (1995) J. Exp. Med. 182:1461-1468
29 Nishimoto N, and Kishimoto T. (2004) Curr Op in Pharmacology 4:386-391
30 Keller E. T. et al. (1996) Front Biosci. 1:340-57
31 Bataille et al. (1995) Blood 86:685-691
32 Lu et al. (1995) Blood 68:3123-3131
33 Blay et al. (1997) Int J. Cancer 424-430
34 Wendling et al. (1993) J. Rheumatol. 20:259-262
35 Emilie et al. (1994) Blood 84:2472-2479
36 Brochier J et al. (1995) Int. J. of Immunopharm. 17:41-48
37 van Zaanen et al. (1998) Brit. Journal. Haematology 102: 783
38 Bell and Kamm, (2000) Aliment. Phamacol. Ther. 14, 501-514
39 Brakenhoff et al (1990) J. Immunol 145:651
40 Mihara et al. (2005) Expert Opinion on Biological Therapy. 5:683-90
41 Lu et al., (2005) Biochemistry 44:11106-14
42 Haan & Maggos (2004) BioCentury, 12(5): A1-A6
43 Koide et al. (1998) Journal of Molecular Biology, 284: 1141-1151.
44 Nygren et al. (1997) Curr. Op. Structural Biology, 7: 463-469
45 Wess, L. (2004) In: BioCentury, The Bernstein Report on BioBusiness, 12(42), A1-A7,
46 Kabat, E. A. et al, Sequences of Proteins of Immunological Interest. $4^{th}$ Edition. US Department of Health and Human Services. (1987)
47 Martin, A. C. R. Accessing the Kabat Antibody Sequence Database by Computer PROTEINS: Structure, Function and Genetics, 25 (1996), 130-133
48 Kabat, E. A. et al. (1991) Sequences of Proteins of Immunological Interest, 5th Edition. US Department of Health and Human Services, Public Service, NIH, Washington
49 Segal et al., (1974) PNAS, 71:4298-4302
50 Amit et al., (1986) Science, 233:747-753
51 Chothia et al., (1987) J. Mol. Biol., 196:901-917
52 Chothia et al., (1989) Nature, 342:877-883
53 Caton et al., (1990) J. Immunol., 144:1965-1968
54 Sharon et al., (1990) PNAS, 87:4814-4817
55 Sharon et al., (1990) J. Immunol., 144:4863-4869
56 Kabat et al., (1991) J. Immunol., 147:1709-1719
57 Holliger & Hudson, *Nature Biotechnology* 23(9):1126-1136 2005
58 Kontermann, R & Dubel, S, *Antibody Engineering*, Springer-Verlag New York, LLC; 2001, ISBN: 3540413545
59 Mendez, M. et al. (1997) Nature Genet, 15(2): 146-156
60 Knappik et al. (2000) J. Mol. Biol. 296, 57-86
61 Krebs et al. (2001) J. Immunological Methods 254 67-84
62 Ward, E. S. et al. (1989) Nature 341, 544-546
63 McCafferty et al (1990) Nature, 348, 552-554
64 Holt et al (2003) Trends in Biotechnology 21, 484-490
65 Bird et al, (1988) Science, 242, 423-426
66 Huston et al, (1988) PNAS USA, 85, 5879-5883
67 Holliger, P. et al, (1993) PNAS USA 90 6444-6448
68 Reiter, Y. et al, (1996) Nature Biotech, 14, 1239-1245
69 Hu, S. et al, (1996) Cancer Res., 56, 3055-3061
70 Qui et al., (2007) *Nat. Biotechnol.* 25:921-929
71 Holliger and Bohlen (1999) Cancer & Metastasis Rev. 18: 411-419
72 Holliger, P. and Winter G. (1993) Curr. Op. Biotech. 4, 446-449
73 Glennie M J et al. (1987) J. Immunol. 139, 2367-2375
74 Repp R. et al. (1995) J. Hemather. 4: 415-21
75 Staerz U. D. and Bevan M. J. (1986) PNAS USA 83: 1453-7
76 Suresh M. R. et al. (1986) Method Enzymol. 121: 210-228
77 Merchand et al. (1998) Nature Biotech. 16:677-681
78 Ridgeway, J. B. B. et al (1996) Protein Eng., 9, 616-621
79 Harlow and Lane, Antibodies: A Laboratory Manual, Cold Spring Harbor Laboratory, Cold Spring Harbor N.Y., pp. 726, 1988
80 Köhler and Milstein (1975) Nature, 256:495-497
81 Wold, et al. Multivariate data analysis in chemistry. Chemometrics—Mathematics and Statistics in Chemistry (Ed.: B. Kowalski), D. Reidel Publishing Company, Dordrecht, Holland, 1984 (ISBN 90-277-1846-6)
82 Norman et al. Applied Regression Analysis. Wiley-Interscience; $3^{rd}$ edition (April 1998) ISBN: 0471170828
83 Kandel, Abraham & Backer, Eric. Computer-Assisted Reasoning in Cluster Analysis. Prentice Hall PTR, (May 11, 1995), ISBN: 0133418847
84 Krzanowski, Wojtek. Principles of Multivariate Analysis: A User's Perspective (Oxford Statistical Science Series, No 22 (Paper)). Oxford University Press; (December 2000), ISBN: 0198507089
85 Witten, Ian H. & Frank, Eibe. Data Mining: Practical Machine Learning Tools and Techniques with Java Implementations. Morgan Kaufmann; (Oct. 11, 1999), ISBN: 1558605525
86 Denison David G. T. (Editor), Christopher C. Holmes, Bani K. Mallick, Adrian F. M. Smith. Bayesian Methods for Nonlinear Classification and Regression (Wiley Series in Probability and Statistics). John Wiley & Sons; (July 2002), ISBN: 0471490369
87 Ghose, Arup K. & Viswanadhan, Vellarkad N. Combinatorial Library Design and Evaluation Principles, Software, Tools, and Applications in Drug Discovery. ISBN: 0-8247-0487-8
88 Chothia C. et al. (1992) J. Molecular Biology 227, 799-817
89 Al-Lazikani, et al. (1997) J. Molecular Biology 273(4), 927-948
90 Chothia, et al. (1986) Science, 223, 755-758
91 Whitelegg, N. R. u. & Rees, A. R (2000). Prot. Eng., 12, 815-824
92 Guex, N. and Peitsch, M. C. (1997) Electrophoresis 18, 2714-2723
93 Altschul et al. (1990) J. Mol. Biol. 215: 405-410
94 Pearson and Lipman (1988) PNAS USA 85: 2444-2448
95 Smith and Waterman (1981) J. Mol Biol. 147: 195-197
96 Voet & Voet, *Biochemistry*, 2nd Edition, (Wiley) 1995.
97 Gram et al., (1992) PNAS USA, 89:3576-3580
98 Barbas et al., (1994) PNAS USA, 91:3809-3813
99 Schier et al., (1996) *J. Mol. Biol.* 263:551-567
100 Marks et al (1992) *Bio/Technology* 10:779-783
101 Kay, B. K., Winter, J., and McCafferty, J. (1996) Phage Display of Peptides and Proteins: A Laboratory Manual, San Diego: Academic Press
102 Hunter W. M. and Greenwood F. C. (1962) Nature 194: 495
103 Plückthun, A. (1991) Bio/Technology 9: 545-551

104 Chadd H E and Chamow S M (2001) Current Opinion in Biotechnology 12: 188-194
105 Andersen D C and Krummen L (2002) Current Opinion in Biotechnology 13: 117
106 Larrick J W and Thomas D W (2001) Current Opinion in Biotechnology 12:411-418
107 Sambrook and Russell, *Molecular Cloning: a Laboratory Manual:* 3rd edition, 2001, Cold Spring Harbor Laboratory Press
108 Ausubel et al. eds., *Short Protocols in Molecular Biology: A Compendium of Methods from Current Protocols in Molecular Biology*, John Wiley & Sons, 4$^{th}$ edition 1999
109 Robinson, J. R. ed., (1978) Sustained and Controlled Release Drug Delivery Systems, Marcel Dekker, Inc., New York
110 Ledermann J. A. et al. (1991) Int. J. Cancer 47: 659-664
111 Bagshawe K. D. et al. (1991) Antibody, Immunoconjugates and Radiopharmaceuticals 4: 915-922
112 Desgeorges et al. (1997) J. Rheumatol 24:1510
113 Yokota et al. (2005) Arth & Rheum 52(3): 818-25
114 Klouche et al., (1999) J. Immunol. 163(8) 4583-9
115 Oh et al., (2001) J. Immunol. 166: 2695-704
116 Fasshauer et al., (2003) Horm. Metab. Res. 35(3) 147-52
117 Marz et al., (1998) Proc. Natl. Acad. Sci. USA 95(6) 3251-6
118 Modur et al., (1997) J. Clin. Invest. 100(1) 2752-6
119 Murakami-Morl et al., (1996) Cell Growth Differ. 7(12) 1697-703
120 Vaughan, T. J., et al. (1996) *Nature Biotech.* 14, 309-314.
121 Hutchings, C. (2001) Generation of Naïve Human Antibody Libraries, in Antibody Engineering, R. Kontermann and S. Dubel, Editors. Springer Laboratory Manuals, Berlin. p. 93
122 Hawkins et al (1992) Journal of Molecular Biology 226, 889-896
123 Persic L et al. (1997) *Gene* 187, 9-18.
124 Mach et al (1992) Anal. Biochem. 200(1): 20-26
125 Osbourn (1996) Immunotechnology. 2, 181-196
126 Bannister et al (2006) Biotechnology and Bioengineering, 94: 931-937
127 McCafferty et al (1994) Appl. Biochem. Biotech. 47: 157-71
128 Clackson and Lowman (2004) A Practical Approach, Oxford University Press
129 Thompson (1996) J. Molecular Biology. 256. 77-88
130 http://vbase.mrc-cpe.cam.ac.uk/
131 Foote J & Winter G (1992) J. Molecular biology 224(2) 487-99
132 Karlsson et al (1991) J. Immunol Methods 145 (1-2) 229-240
133 Lu et al. (1995) Blood. 86: 3123-3131
134 Kitamura T et al (1989) J. Cellular Physiology 140. 323-334

TABLE 7

| | HCDR1 | | | | | HCDR2 | | | | | | | | | | | | | | | HCDR3 | | | |
|---|---|---|---|---|---|---|---|---|---|---|---|---|---|---|---|---|---|---|---|---|---|---|---|---|
| Kabat numbering | 31 | 32 | 33 | 34 | 35 | 50 | 51 | 52 | 52A | 53 | 54 | 55 | 56 | 57 | 58 | 59 | 60 | 61 | 62 | 63 | 64 | 65 | 95 | 96 | 97 | 98 | 99 |
| CAN022D10 | S | N | Y | M | I | D | L | Y | Y | Y | A | G | D | T | Y | Y | A | D | S | V | K | G | W | A | D | D | H |
| Antibody 2 | | | | | T | | | | | | | | | | | | | | | | R | | | | | G | |
| Antibody 3 | | | | | V | | | | | | | | | | | | | | | | | | | | | G | |
| Antibody 4 | | | | | T | | | | | | | | | | | | | | | | | | | | | G | |
| Antibody 5 | | | | | | | | | | | | | | | | | | | | | | | | | | G | |
| Antibody 7 | | | | | | | | | | | | | | | | | | | | | | | | | | | |
| Antibody 8 | | | | | | | | | | | | | | | | | | | | | | | | | | | |
| Antibody 10 | | | | | | | | | | | | | | | | | | | | | | | | E | E | E | G |
| Antibody 14 | | | | | | | | | | | | | | | | | | | | | | | | | | | |
| Antibody 16 | | | | | | | | | | | | | | | | | | | | | | | | | | | |
| Antibody 17 | | | | | | | | | | | | | | | | | | | | | | | | | | | |
| Antibody 18 | | | | | | | | | | | | | | | | | | | | | | | | | | | |
| Antibody 19 | | | | | | | | | | | | | | | | | | | | | | | | | | | |
| Antibody 21 | | | | | | | | | | | | | | | | | | | | | | | | | | | |
| Antibody 22 | | | | | | | | | | | | | | | | | | | | | | | | | | | |
| Antibody 23 | | | | | | | | | | | | | | | | | | | | | | | | | | | |

| | HCDR3 | | | | | | | LCDR1 | | | | | | | | | | | LCDR2 | | | | | |
|---|---|---|---|---|---|---|---|---|---|---|---|---|---|---|---|---|---|---|---|---|---|---|---|---|
| Kabat numbering | 100 | 100A | 100B | 100C | 100D | 101 | 102 | 24 | 25 | 26 | 27 | 28 | 29 | 30 | 31 | 32 | 33 | 34 | 50 | 51 | 52 | 53 | 54 | 55 |
| CAN022D10 | Y | Y | Y | I | — | D | V | R | A | S | Q | G | I | S | S | W | L | A | K | A | S | T | L | E |
| Antibody 2 | | | | | | | | | | | | | | | | | | T | | | | | | |
| Antibody 3 | | H | | | | | | | | | | | | | | | | | | | | | | |
| Antibody 4 | | | A | | | | | | | | | | | | | | | | | | | | | |
| Antibody 5 | | | A | | | | | | | | | | | | | | | | | | | | | |
| Antibody 7 | P | A | W | V | | | L | | | | | | | | | | | | | | | | | |
| Antibody 8 | P | R | | | | | H | | | | | | | | | | | | | | | | | |
| Antibody 10 | R | G | | | | | | | | | | | | | | | | | | | | | | |
| Antibody 14 | N | | P | H | I | | | | | | | | | | | | | | | | | | | |
| Antibody 16 | P | P | | | | | L | | | | | | | | | | | | | | | | | |
| Antibody 17 | P | P | | | | | M | | | | | | | | | | | | | | | | | |
| Antibody 18 | P | P | W | | | | L | | | | | | | | | | | | | | | | | |
| Antibody 19 | P | S | H | L | | | I | | | | | | | | | | | | | | | | | |
| Antibody 21 | P | S | H | | | | | | | | | | | | | | | | | | | | | |
| Antibody 22 | N | N | T | Y | I | | | | | | | | | | | | | | | | | | | |
| Antibody 23 | A | P | W | V | | | L | | | | | | | | | | | | | | | | | |

TABLE 7-continued

| | Kabat numbering | LCDR2 56 | 89 | 90 | 91 | 92 | 93 | LCDR3 94 | 95 | 96 | 97 |
|---|---|---|---|---|---|---|---|---|---|---|---|
| | CAN022D10 | S | Q | Q | S | Y | S | T | P | W | T |
| | Antibody 2 | | | | | | | A | | | |
| | Antibody 3 | | | | | | | | | | |
| | Antibody 4 | | | | | | | A | | | |
| | Antibody 5 | | | | | | | A | | | |
| | Antibody 7 | | | | | W | L | G | — | G | S |
| | Antibody 8 | | | | | W | L | G | — | G | S |
| | Antibody 10 | | | | | W | L | G | — | G | S |
| | Antibody 14 | | A | A | H | A | A | | | | |
| | Antibody 16 | | | | | W | L | G | — | G | S |
| | Antibody 17 | | | | | W | L | G | — | G | S |
| | Antibody 18 | | | | | W | L | G | — | G | S |
| | Antibody 19 | | | | | W | L | G | — | G | S |
| | Antibody 21 | | | | | W | L | G | — | G | S |
| | Antibody 22 | | A | A | H | A | A | | | | |
| | Antibody 23 | | | | | W | L | G | — | G | S |

The invention claimed is:

1. An isolated antibody molecule for human IL-6, comprising a set of CDRs: HCDR1, HCDR2, HCDR3, LCDR1, LCDR2 and LCDR3, in which:
   HCDR1 has amino acid sequence SEQ ID NO: 3;
   HCDR2 has amino acid sequence SEQ ID NO: 4;
   HCDR3 has amino acid sequence SEQ ID NO: 115;
   LCDR1 has amino acid sequence SEQ ID NO: 8;
   LCDR2 has amino acid sequence SEQ ID NO: 9; and
   LCDR3 has amino acid sequence SEQ ID NO: 120, and wherein
   the binding member has an $IC_{50}$ of less than 100 pM in an assay for inhibition of proliferation of TF-1 cells in response to 20 pM human IL-6.

2. The antibody molecule of claim 1, wherein the antibody molecule comprises the VH domain amino acid sequence of SEQ ID NO: 112 and the VL domain amino acid sequence of SEQ ID NO: 117.

3. A composition comprising an antibody molecule according to claim 1 for use in treating rheumatoid arthritis.

4. A method of treating rheumatoid arthritis in an individual, comprising administering an antibody molecule according to claim 1, to the individual.

5. An isolated nucleic acid molecule comprising a nucleotide sequence encoding an antibody molecule according to claim 1.

6. A host cell in vitro transformed with nucleic acid according to claim 5.

* * * * *

SEQUENCE LISTING

<160> NUMBER OF SEQ ID NOS: 185

<210> SEQ ID NO 1
<211> LENGTH: 360
<212> TYPE: DNA
<213> ORGANISM: Homo sapiens
<220> FEATURE:
<223> OTHER INFORMATION: CAN022D10

<400> SEQUENCE: 1

```
gaagtgcagc tggtgcagtc tgggggaggc ttgatccagc cggggggtc cctgagactc    60 tcctgtgcag cctctgggtt caccatcagc agcaactaca tgatttgggt ccgtcaggct   120
ccagggaagg gctggagtg gtctccgat ctttattatt atgctggtga cacatattac     180
gcagactccg tgaagggccg attcaccatg tccagagaca tttccaagaa caccgtgtat   240
cttcaaatga acagcctgag agccgaggac acgggtgtct attattgtgc gagatgggcc   300
gatgaccact actattacat tgacgtctgg ggcaggggca ccctggtcac cgtctcgagt   360
```

<210> SEQ ID NO 2
<211> LENGTH: 120
<212> TYPE: PRT
<213> ORGANISM: Homo sapiens
<220> FEATURE:
<223> OTHER INFORMATION: CAN022D10

<400> SEQUENCE: 2

Glu Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Ile Ser Ser Asn
            20                  25                  30

Tyr Met Ile Trp Val Arg Gln Ala Pro Gly Lys Gly Leu Glu Trp Val
        35                  40                  45

Ser Asp Leu Tyr Tyr Ala Gly Asp Thr Tyr Tyr Ala Asp Ser Val
    50                  55                  60

Lys Gly Arg Phe Thr Met Ser Arg Asp Ile Ser Lys Asn Thr Val Tyr
65                  70                  75                  80

Leu Gln Met Asn Ser Leu Arg Ala Glu Asp Thr Gly Val Tyr Tyr Cys
                85                  90                  95

Ala Arg Trp Ala Asp Asp His Tyr Tyr Tyr Ile Asp Val Trp Gly Arg

```
                    100                 105                 110
Gly Thr Leu Val Thr Val Ser Ser
        115                 120

<210> SEQ ID NO 3
<211> LENGTH: 5
<212> TYPE: PRT
<213> ORGANISM: Homo sapiens
<220> FEATURE:
<223> OTHER INFORMATION: CAN022D10

<400> SEQUENCE: 3

Ser Asn Tyr Met Ile
1               5

<210> SEQ ID NO 4
<211> LENGTH: 17
<212> TYPE: PRT
<213> ORGANISM: Homo sapiens
<220> FEATURE:
<223> OTHER INFORMATION: CAN022D10

<400> SEQUENCE: 4

Asp Leu Tyr Tyr Tyr Ala Gly Asp Thr Tyr Tyr Ala Asp Ser Val Lys
1               5                   10                  15

Gly

<210> SEQ ID NO 5
<211> LENGTH: 11
<212> TYPE: PRT
<213> ORGANISM: Homo sapiens
<220> FEATURE:
<223> OTHER INFORMATION: CAN022D10

<400> SEQUENCE: 5

Trp Ala Asp Asp His Tyr Tyr Tyr Ile Asp Val
1               5                   10

<210> SEQ ID NO 6
<211> LENGTH: 324
<212> TYPE: DNA
<213> ORGANISM: Homo sapiens
<220> FEATURE:
<223> OTHER INFORMATION: CAN022D10

<400> SEQUENCE: 6
gacatcgtga tgacccagtc tccttccacc ctgtctgcat ctgtaggaga cagagtcacc      60
atcacttgcc gggccagtca gggtattagt agctggttgg cctggtatca gcagaaacca     120
gggagagccc ctaaggtctt gatctataag gcatctactt tagaaagtgg ggtcccatca     180
aggttcagcg gcagtggatc tgggacagat ttcactctca ccatcagcag tctgcaacct     240
gaagattttg caacttacta ctgtcaacag agttacagta ccccgtggac gttcggccaa     300
gggaccaagc tggagatcaa acgt                                            324

<210> SEQ ID NO 7
<211> LENGTH: 108
<212> TYPE: PRT
<213> ORGANISM: Homo sapiens
<220> FEATURE:
<223> OTHER INFORMATION: CAN022D10

<400> SEQUENCE: 7

Asp Ile Val Met Thr Gln Ser Pro Ser Thr Leu Ser Ala Ser Val Gly
```

```
                1               5                  10                 15
Asp Arg Val Thr Ile Thr Cys Arg Ala Ser Gln Gly Ile Ser Ser Trp
                20                 25                 30

Leu Ala Trp Tyr Gln Gln Lys Pro Gly Arg Ala Pro Lys Val Leu Ile
            35                 40                 45

Tyr Lys Ala Ser Thr Leu Glu Ser Gly Val Pro Ser Arg Phe Ser Gly
        50                 55                 60

Ser Gly Ser Gly Thr Asp Phe Thr Leu Thr Ile Ser Ser Leu Gln Pro
 65                 70                 75                 80

Glu Asp Phe Ala Thr Tyr Tyr Cys Gln Gln Ser Tyr Ser Thr Pro Trp
                85                 90                 95

Thr Phe Gly Gln Gly Thr Lys Leu Glu Ile Lys Arg
            100                 105
```

<210> SEQ ID NO 8
<211> LENGTH: 11
<212> TYPE: PRT
<213> ORGANISM: Homo sapiens
<220> FEATURE:
<223> OTHER INFORMATION: CAN022D10

<400> SEQUENCE: 8

```
Arg Ala Ser Gln Gly Ile Ser Ser Trp Leu Ala
1               5                  10
```

<210> SEQ ID NO 9
<211> LENGTH: 7
<212> TYPE: PRT
<213> ORGANISM: Homo sapiens
<220> FEATURE:
<223> OTHER INFORMATION: CAN022D10

<400> SEQUENCE: 9

```
Lys Ala Ser Thr Leu Glu Ser
1               5
```

<210> SEQ ID NO 10
<211> LENGTH: 9
<212> TYPE: PRT
<213> ORGANISM: Homo sapiens
<220> FEATURE:
<223> OTHER INFORMATION: CAN022D10

<400> SEQUENCE: 10

```
Gln Gln Ser Tyr Ser Thr Pro Trp Thr
1               5
```

<210> SEQ ID NO 11
<211> LENGTH: 360
<212> TYPE: DNA
<213> ORGANISM: Homo sapiens
<220> FEATURE:
<223> OTHER INFORMATION: Antibody 02

<400> SEQUENCE: 11

```
gaggtgcagc tggtgcagtc agggggaggc ttgatccagc cggggggggtc cctgagactc    60 tcctgtgcag cctctgggtt caccatcagc agcaactaca tgacttgggt ccgtcaggct   120
ccagggaagg ggctggagtg ggtctccgat ctttattatt atgctggtga cacatattac   180
gcagactccg tgaggggccg attcaccatg tccagagaca tttccaagaa caccgtgtat   240
cttcaaatgg acagcctgag agccgaggac acgggtgtct attattgtgc gagatgggcc   300
```
gatggccact actattacat tgacgtctgg ggcgggggca ccctggtcac cgtctcgagt    360

<210> SEQ ID NO 12
<211> LENGTH: 120
<212> TYPE: PRT
<213> ORGANISM: Homo sapiens
<220> FEATURE:
<223> OTHER INFORMATION: Antibody 02

<400> SEQUENCE: 12

Glu Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Ile Ser Ser Asn
            20                  25                  30

Tyr Met Thr Trp Val Arg Gln Ala Pro Gly Lys Gly Leu Glu Trp Val
        35                  40                  45

Ser Asp Leu Tyr Tyr Tyr Ala Gly Asp Thr Tyr Tyr Ala Asp Ser Val
    50                  55                  60

Arg Gly Arg Phe Thr Met Ser Arg Asp Ile Ser Lys Asn Thr Val Tyr
65                  70                  75                  80

Leu Gln Met Asp Ser Leu Arg Ala Glu Asp Thr Gly Val Tyr Tyr Cys
                85                  90                  95

Ala Arg Trp Ala Asp Gly His Tyr Tyr Tyr Ile Asp Val Trp Gly Gly
            100                 105                 110

Gly Thr Leu Val Thr Val Ser Ser
        115                 120

<210> SEQ ID NO 13
<211> LENGTH: 5
<212> TYPE: PRT
<213> ORGANISM: Homo sapiens
<220> FEATURE:
<223> OTHER INFORMATION: Antibody 02

<400> SEQUENCE: 13

Ser Asn Tyr Met Thr
1               5

<210> SEQ ID NO 14
<211> LENGTH: 17
<212> TYPE: PRT
<213> ORGANISM: Homo sapiens
<220> FEATURE:
<223> OTHER INFORMATION: Antibody 02

<400> SEQUENCE: 14

Asp Leu Tyr Tyr Tyr Ala Gly Asp Thr Tyr Tyr Ala Asp Ser Val Arg
1               5                   10                  15

Gly

<210> SEQ ID NO 15
<211> LENGTH: 11
<212> TYPE: PRT
<213> ORGANISM: Homo sapiens
<220> FEATURE:
<223> OTHER INFORMATION: Antibody 02

<400> SEQUENCE: 15

Trp Ala Asp Gly His Tyr Tyr Tyr Ile Asp Val
1               5                   10

<210> SEQ ID NO 16

-continued

<211> LENGTH: 324
<212> TYPE: DNA
<213> ORGANISM: Homo sapiens
<220> FEATURE:
<223> OTHER INFORMATION: Antibody 02

<400> SEQUENCE: 16
gacatcgtga tgacccagtc cccttccacc ctgtctgcat ctgtaggaga cagagtcact    60
atcacttgcc gggccagtca gggtattagt agctggttga cctggtatca gcagaaacca   120
gggagagccc ctaaggtctt gatctataag gcatctactt tagaaagtgg ggtcccatca   180
aggttcagcg gcagtggatc tgggacagat ttcaccctca ccatcagcag tctgcaacct   240
gaagattttg caacttacta ctgtcaacag agttacagtg ccccgtggac gttcggccaa   300
gggaccaagc tggagctcaa acgt                                          324

<210> SEQ ID NO 17
<211> LENGTH: 108
<212> TYPE: PRT
<213> ORGANISM: Homo sapiens
<220> FEATURE:
<223> OTHER INFORMATION: Antibody 02

<400> SEQUENCE: 17

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Thr Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ala Pro Trp
                85                  90                  95

Thr Phe Gly Gln Gly Thr Lys Leu Glu Leu Lys Arg
            100                 105

<210> SEQ ID NO 18
<211> LENGTH: 11
<212> TYPE: PRT
<213> ORGANISM: Homo sapiens
<220> FEATURE:
<223> OTHER INFORMATION: Antibody 02

<400> SEQUENCE: 18

Arg Ala Ser Gln Gly Ile Ser Ser Trp Leu Thr
1               5                   10

<210> SEQ ID NO 19
<211> LENGTH: 7
<212> TYPE: PRT
<213> ORGANISM: Homo sapiens
<220> FEATURE:
<223> OTHER INFORMATION: Antibody 02

<400> SEQUENCE: 19

Lys Ala Ser Thr Leu Glu Ser
1               5

<210> SEQ ID NO 20

```
<211> LENGTH: 9
<212> TYPE: PRT
<213> ORGANISM: Homo sapiens
<220> FEATURE:
<223> OTHER INFORMATION: Antibody 02

<400> SEQUENCE: 20

Gln Gln Ser Tyr Ser Ala Pro Trp Thr
1               5

<210> SEQ ID NO 21
<211> LENGTH: 360
<212> TYPE: DNA
<213> ORGANISM: Homo sapiens
<220> FEATURE:
<223> OTHER INFORMATION: Antibody 03

<400> SEQUENCE: 21
caggtacagc tggtgcagtc tgggggaggc ttgatccagc cggggggggtc cctgagactc      60 tcctgtgcag cctctgggtt caccatcagc agcaactaca tggtttgggt ccgtcaggct     120
ccggggaagg ggctggagtg ggtctccgat ctttattatt atgctggtga cacatattac     180
gcagactccg tgaagggccg attcaccgtg tccagagaca tttccaagaa caccgtgtat     240
cttcaaatga acagcctgag agccgaggac acgggtgtct attattgtgc gagatgggcc     300
gatgaccact actatcacat tgacgtctgg ggcaggggca ccctggtcac cgtctcgagt     360

<210> SEQ ID NO 22
<211> LENGTH: 120
<212> TYPE: PRT
<213> ORGANISM: Homo sapiens
<220> FEATURE:
<223> OTHER INFORMATION: Antibody 03

<400> SEQUENCE: 22

Gln Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Ile Ser Ser Asn
            20                  25                  30

Tyr Met Val Trp Val Arg Gln Ala Pro Gly Lys Gly Leu Glu Trp Val
        35                  40                  45

Ser Asp Leu Tyr Tyr Tyr Ala Gly Asp Thr Tyr Tyr Ala Asp Ser Val
    50                  55                  60

Lys Gly Arg Phe Thr Val Ser Arg Asp Ile Ser Lys Asn Thr Val Tyr
65                  70                  75                  80

Leu Gln Met Asn Ser Leu Arg Ala Glu Asp Thr Gly Val Tyr Tyr Cys
                85                  90                  95

Ala Arg Trp Ala Asp Asp His Tyr His Ile Asp Val Trp Gly Arg
            100                 105                 110

Gly Thr Leu Val Thr Val Ser Ser
        115                 120

<210> SEQ ID NO 23
<211> LENGTH: 5
<212> TYPE: PRT
<213> ORGANISM: Homo sapiens
<220> FEATURE:
<223> OTHER INFORMATION: Antibody 03

<400> SEQUENCE: 23

Ser Asn Tyr Met Val
1               5
```

<210> SEQ ID NO 24
<211> LENGTH: 17
<212> TYPE: PRT
<213> ORGANISM: Homo sapiens
<220> FEATURE:
<223> OTHER INFORMATION: Antibody 03

<400> SEQUENCE: 24

Asp Leu Tyr Tyr Tyr Ala Gly Asp Thr Tyr Tyr Ala Asp Ser Val Lys
1               5                   10                  15

Gly

<210> SEQ ID NO 25
<211> LENGTH: 11
<212> TYPE: PRT
<213> ORGANISM: Homo sapiens
<220> FEATURE:
<223> OTHER INFORMATION: Antibody 03

<400> SEQUENCE: 25

Trp Ala Asp Asp His Tyr Tyr His Ile Asp Val
1               5                   10

<210> SEQ ID NO 26
<211> LENGTH: 324
<212> TYPE: DNA
<213> ORGANISM: Homo sapiens
<220> FEATURE:
<223> OTHER INFORMATION: Antibody 03

<400> SEQUENCE: 26
gacatcgtga tgacccagtc tccttccacc ctgtctgcat ctgtaggaga cagagtcacc      60
atcacttgcc gggccagtca gggtattagt agctggttgg cctggtatca gcagaaacca     120
gggagagccc ctaaggcctt gatctataag gcatctactt tagaaagtgg ggtcccatca     180
aggttcagcg gcagtggatc tgggacagat ttcactctca ccatcagcag tctgcaacct     240
gaagattttg caacttacta ctgtcaacag agttacagta ccccgtggac gttcggccaa     300
gggaccaagc tggagatcaa acgt                                            324

<210> SEQ ID NO 27
<211> LENGTH: 108
<212> TYPE: PRT
<213> ORGANISM: Homo sapiens
<220> FEATURE:
<223> OTHER INFORMATION: Antibody 03

<400> SEQUENCE: 27

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Arg Ala Pro Lys Ala Leu Ile
            35                  40                  45

Tyr Lys Ala Ser Thr Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Leu Glu Ile Lys Arg
            100                 105

<210> SEQ ID NO 28
<211> LENGTH: 11
<212> TYPE: PRT
<213> ORGANISM: Homo sapiens
<220> FEATURE:
<223> OTHER INFORMATION: Antibody 03

<400> SEQUENCE: 28

Arg Ala Ser Gln Gly Ile Ser Ser Trp Leu Ala
1               5                   10

<210> SEQ ID NO 29
<211> LENGTH: 7
<212> TYPE: PRT
<213> ORGANISM: Homo sapiens
<220> FEATURE:
<223> OTHER INFORMATION: Antibody 03

<400> SEQUENCE: 29

Lys Ala Ser Thr Leu Glu Ser
1               5

<210> SEQ ID NO 30
<211> LENGTH: 9
<212> TYPE: PRT
<213> ORGANISM: Homo sapiens
<220> FEATURE:
<223> OTHER INFORMATION: Antibody 03

<400> SEQUENCE: 30

Gln Gln Ser Tyr Ser Thr Pro Trp Thr
1               5

<210> SEQ ID NO 31
<211> LENGTH: 360
<212> TYPE: DNA
<213> ORGANISM: Homo sapiens
<220> FEATURE:
<223> OTHER INFORMATION: Antibody 04

<400> SEQUENCE: 31
gaggtgcagc tggtgcagtc agggggaggc ttgatccagc cggggggtc cctgagactc      60 tcctgtgcag cctctgggtt caccgtcagc agcaactaca tgacttgggt ccgacaggct    120
ccagggaagg ggctggagtg gtctccgat ctttattatt atgctggcga cacgtattac     180
gcagactccg tgaagggccg attcaccatg tccagagaca tttccaagaa caccgtgtac    240
cttcaaatga acagcctaag agccgaggac acgggtgtct attattgtgc gagatggggcc   300 gatggccact actattacgc tgacgtctgg ggcaggggca cctggtctc cgtctcgagt     360

<210> SEQ ID NO 32
<211> LENGTH: 120
<212> TYPE: PRT
<213> ORGANISM: Homo sapiens
<220> FEATURE:
<223> OTHER INFORMATION: Antibody 04

<400> SEQUENCE: 32

Glu Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

```
Tyr Met Thr Trp Val Arg Gln Ala Pro Gly Lys Gly Leu Glu Trp Val
        35                  40                  45

Ser Asp Leu Tyr Tyr Tyr Ala Gly Asp Thr Tyr Tyr Ala Asp Ser Val
    50                  55                  60

Lys Gly Arg Phe Thr Met Ser Arg Asp Ile Ser Lys Asn Thr Val Tyr
65                  70                  75                  80

Leu Gln Met Asn Ser Leu Arg Ala Glu Asp Thr Gly Val Tyr Tyr Cys
                85                  90                  95

Ala Arg Trp Ala Asp Gly His Tyr Tyr Tyr Ala Asp Val Trp Gly Arg
            100                 105                 110

Gly Thr Leu Val Ser Val Ser Ser
            115                 120

<210> SEQ ID NO 33
<211> LENGTH: 5
<212> TYPE: PRT
<213> ORGANISM: Homo sapiens
<220> FEATURE:
<223> OTHER INFORMATION: Antibody 04

<400> SEQUENCE: 33

Ser Asn Tyr Met Thr
1               5

<210> SEQ ID NO 34
<211> LENGTH: 17
<212> TYPE: PRT
<213> ORGANISM: Homo sapiens
<220> FEATURE:
<223> OTHER INFORMATION: Antibody 04

<400> SEQUENCE: 34

Asp Leu Tyr Tyr Tyr Ala Gly Asp Thr Tyr Tyr Ala Asp Ser Val Lys
1               5                   10                  15

Gly

<210> SEQ ID NO 35
<211> LENGTH: 11
<212> TYPE: PRT
<213> ORGANISM: Homo sapiens
<220> FEATURE:
<223> OTHER INFORMATION: Antibody 04

<400> SEQUENCE: 35

Trp Ala Asp Gly His Tyr Tyr Tyr Ala Asp Val
1               5                   10

<210> SEQ ID NO 36
<211> LENGTH: 324
<212> TYPE: DNA
<213> ORGANISM: Homo sapiens
<220> FEATURE:
<223> OTHER INFORMATION: Antibody 04

<400> SEQUENCE: 36
gacatcgtga tgacccagtc tccctccacc ctgtctgcat ctgtaggaga cagagtcacc      60
atcacttgcc gggccagtca gggaattagt agctggttgg cctggtatca gcagaaacca     120
gggagagccc ctaaggtctt gatctataag gcatctacgt tagaaagtgg ggtcccatca     180
aggttcagcg gcagtggatc tgggacagat ttcactctca ccatcagcag tctgcaacct     240
gaagatttcg catcttacta ctgtcaacag agttacagtg ccccgtggac gttcggccaa     300
```

```
gggaccaagc tggagctcaa acgt                                        324
```

<210> SEQ ID NO 37
<211> LENGTH: 108
<212> TYPE: PRT
<213> ORGANISM: Homo sapiens
<220> FEATURE:
<223> OTHER INFORMATION: Antibody 04

<400> SEQUENCE: 37

```
Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ser Tyr Ser Ala Pro Trp
                85                  90                  95

Thr Phe Gly Gln Gly Thr Lys Leu Glu Leu Lys Arg
            100                 105
```

<210> SEQ ID NO 38
<211> LENGTH: 11
<212> TYPE: PRT
<213> ORGANISM: Homo sapiens
<220> FEATURE:
<223> OTHER INFORMATION: Antibody 04

<400> SEQUENCE: 38

```
Arg Ala Ser Gln Gly Ile Ser Ser Trp Leu Ala
1               5                   10
```

<210> SEQ ID NO 39
<211> LENGTH: 7
<212> TYPE: PRT
<213> ORGANISM: Homo sapiens
<220> FEATURE:
<223> OTHER INFORMATION: Antibody 04

<400> SEQUENCE: 39

```
Lys Ala Ser Thr Leu Glu Ser
1               5
```

<210> SEQ ID NO 40
<211> LENGTH: 9
<212> TYPE: PRT
<213> ORGANISM: Homo sapiens
<220> FEATURE:
<223> OTHER INFORMATION: Antibody 04

<400> SEQUENCE: 40

```
Gln Gln Ser Tyr Ser Ala Pro Trp Thr
1               5
```

<210> SEQ ID NO 41
<211> LENGTH: 360
<212> TYPE: DNA
<213> ORGANISM: Homo sapiens
<220> FEATURE:

<223> OTHER INFORMATION: Antibody 05

<400> SEQUENCE: 41

```
gaggtgcagc tggtgcagtc tgggggaggc ttgatccagc cggggggtc cctgagactc    60
tcctgtgcgg cctctgggtt caccatcagc agcaactaca tgatttgggt ccgtcaggct   120
ccagggaagg ggctggagtg ggtctccgat ctttattatt atgctggcga cacgtattac   180
gcagactccg tgaagggccg attcaccatg tccagagaca tttccaagaa caccgtgtac   240
cttcaaatga acagcctgag agccgaggac acgggtgtct attattgtgc gagatgggcc   300
gatggccact actattacgc tgacgtctgg ggcaggggca ccctggtctc cgtctcgagt   360
```

<210> SEQ ID NO 42
<211> LENGTH: 120
<212> TYPE: PRT
<213> ORGANISM: Homo sapiens
<220> FEATURE:
<223> OTHER INFORMATION: Antibody 05

<400> SEQUENCE: 42

Glu Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Ile Ser Ser Asn
            20                  25                  30

Tyr Met Ile Trp Val Arg Gln Ala Pro Gly Lys Gly Leu Glu Trp Val
        35                  40                  45

Ser Asp Leu Tyr Tyr Tyr Ala Gly Asp Thr Tyr Tyr Ala Asp Ser Val
    50                  55                  60

Lys Gly Arg Phe Thr Met Ser Arg Asp Ile Ser Lys Asn Thr Val Tyr
65                  70                  75                  80

Leu Gln Met Asn Ser Leu Arg Ala Glu Asp Thr Gly Val Tyr Tyr Cys
                85                  90                  95

Ala Arg Trp Ala Asp Gly His Tyr Tyr Tyr Ala Asp Val Trp Gly Arg
            100                 105                 110

Gly Thr Leu Val Ser Val Ser Ser
        115                 120

<210> SEQ ID NO 43
<211> LENGTH: 5
<212> TYPE: PRT
<213> ORGANISM: Homo sapiens
<220> FEATURE:
<223> OTHER INFORMATION: Antibody 05

<400> SEQUENCE: 43

Ser Asn Tyr Met Ile
1               5

<210> SEQ ID NO 44
<211> LENGTH: 17
<212> TYPE: PRT
<213> ORGANISM: Homo sapiens
<220> FEATURE:
<223> OTHER INFORMATION: Antibody 05

<400> SEQUENCE: 44

Asp Leu Tyr Tyr Tyr Ala Gly Asp Thr Tyr Tyr Ala Asp Ser Val Lys
1               5                   10                  15

Gly

```
<210> SEQ ID NO 45
<211> LENGTH: 11
<212> TYPE: PRT
<213> ORGANISM: Homo sapiens
<220> FEATURE:
<223> OTHER INFORMATION: Antibody 05

<400> SEQUENCE: 45

Trp Ala Asp Gly His Tyr Tyr Tyr Ala Asp Val
1               5                   10

<210> SEQ ID NO 46
<211> LENGTH: 324
<212> TYPE: DNA
<213> ORGANISM: Homo sapiens
<220> FEATURE:
<223> OTHER INFORMATION: Antibody 05

<400> SEQUENCE: 46
gacatcgtga tgacccagtc tccccccacc ctgtctgcat ctgtaggaga cagagtcacc      60
atcacttgcc gggccagtca gggaattagt agctggttgg cctggtatca gcagaaacca     120
gggagagccc ctaaggtctt gatctataag gcatctacat tagaaagtgg ggtcccatca     180
aggttcagcg gcagtggatc tgggacagat ttcactctca ccatcagcag tctgcaacct     240
gaagatttcg catcttacta ctgtcaacag agttacagtg ccccgtggac gtttggccaa     300
gggaccaagc tggagatcaa acgt                                            324

<210> SEQ ID NO 47
<211> LENGTH: 108
<212> TYPE: PRT
<213> ORGANISM: Homo sapiens
<220> FEATURE:
<223> OTHER INFORMATION: Antibody 05

<400> SEQUENCE: 47

Asp Ile Val Met Thr Gln Ser Pro Pro Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ser Tyr Ser Ala Pro Trp
                85                  90                  95

Thr Phe Gly Gln Gly Thr Lys Leu Glu Ile Lys Arg
            100                 105

<210> SEQ ID NO 48
<211> LENGTH: 11
<212> TYPE: PRT
<213> ORGANISM: Homo sapiens
<220> FEATURE:
<223> OTHER INFORMATION: Antibody 05

<400> SEQUENCE: 48

Arg Ala Ser Gln Gly Ile Ser Ser Trp Leu Ala
1               5                   10
```

<210> SEQ ID NO 49
<211> LENGTH: 7
<212> TYPE: PRT
<213> ORGANISM: Homo sapiens
<220> FEATURE:
<223> OTHER INFORMATION: Antibody 05

<400> SEQUENCE: 49

Lys Ala Ser Thr Leu Glu Ser
1               5

<210> SEQ ID NO 50
<211> LENGTH: 9
<212> TYPE: PRT
<213> ORGANISM: Homo sapiens
<220> FEATURE:
<223> OTHER INFORMATION: Antibody 05

<400> SEQUENCE: 50

Gln Gln Ser Tyr Ser Ala Pro Trp Thr
1               5

<210> SEQ ID NO 51
<211> LENGTH: 360
<212> TYPE: DNA
<213> ORGANISM: Homo sapiens
<220> FEATURE:
<223> OTHER INFORMATION: Antibody 07

<400> SEQUENCE: 51

```
gaggtgcagc tggtggagtc tgggggaggc ttggtccagc cggggggtc cctgagactc      60 tcctgtgcag cctctgggtt caccatcagc agcaactaca tgatttgggt ccgtcaggct     120
ccagggaagg gctgagtg gtctccgat ctttattatt atgctggtga cacatattac       180
gcagactccg tgaagggccg attcaccatg tccagagaca tttccaagaa caccgtgtat    240
cttcaaatga acagcctgag agccgaggac acggctgtct attattgtgc gagatgggcc    300
gatgaccacc cggcctgggt ggacctctgg ggcaggggca cctggtcac cgtctcctca    360
```

<210> SEQ ID NO 52
<211> LENGTH: 120
<212> TYPE: PRT
<213> ORGANISM: Homo sapiens
<220> FEATURE:
<223> OTHER INFORMATION: Antibody 07

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Asn
            20                  25                  30

Tyr Met Ile Trp Val Arg Gln Ala Pro Gly Lys Gly Leu Glu Trp Val
        35                  40                  45

Ser Asp Leu Tyr Tyr Tyr Ala Gly Asp Thr Tyr Tyr Ala Asp Ser Val
    50                  55                  60

Lys Gly Arg Phe Thr Met Ser Arg Asp Ile Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Trp Ala Asp Asp His Pro Ala Trp Val Asp Leu Trp Gly Arg
            100                 105                 110

Gly Thr Leu Val Thr Val Ser Ser
        115                 120

<210> SEQ ID NO 53
<211> LENGTH: 5
<212> TYPE: PRT
<213> ORGANISM: Homo sapiens
<220> FEATURE:
<223> OTHER INFORMATION: Antibody 07

<400> SEQUENCE: 53

Ser Asn Tyr Met Ile
1               5

<210> SEQ ID NO 54
<211> LENGTH: 17
<212> TYPE: PRT
<213> ORGANISM: Homo sapiens
<220> FEATURE:
<223> OTHER INFORMATION: Antibody 07

<400> SEQUENCE: 54

Asp Leu Tyr Tyr Tyr Ala Gly Asp Thr Tyr Tyr Ala Asp Ser Val Lys
1               5                   10                  15

Gly

<210> SEQ ID NO 55
<211> LENGTH: 11
<212> TYPE: PRT
<213> ORGANISM: Homo sapiens
<220> FEATURE:
<223> OTHER INFORMATION: Antibody 07

<400> SEQUENCE: 55

Trp Ala Asp Asp His Pro Ala Trp Val Asp Leu
1               5                   10

<210> SEQ ID NO 56
<211> LENGTH: 321
<212> TYPE: DNA
<213> ORGANISM: Homo sapiens
<220> FEATURE:
<223> OTHER INFORMATION: Antibody 07

<400> SEQUENCE: 56
gacatccaga tgacccagtc tccttccacc ctgtctgcat ctgtaggaga cagagtcacc     60
atcacttgcc gggccagtca gggtattagt agctggttgg cctggtatca gcagaaacca    120
gggaaagccc ctaaggtctt gatctataag gcatctactt tagaaagtgg ggtcccatca    180
aggttcagcg gcagtggatc tgggacagaa ttcactctca ccatcagcag tctgcaacct    240
gatgattttg caacttacta ctgtcaacag agttggctcg cgggtcgtt cggccaaggg    300 accaagctgg agatcaaacg t                                              321

<210> SEQ ID NO 57
<211> LENGTH: 107
<212> TYPE: PRT
<213> ORGANISM: Homo sapiens
<220> FEATURE:
<223> OTHER INFORMATION: Antibody 07

<400> SEQUENCE: 57

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp

```
                          20                  25                  30
Leu Ala Trp Tyr Gln Gln Lys Pro Gly Lys Ala Pro Lys Val Leu Ile
                35                  40                  45

Tyr Lys Ala Ser Thr Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Trp Leu Gly Gly Ser
                85                  90                  95

Phe Gly Gln Gly Thr Lys Leu Glu Ile Lys Arg
            100                 105

<210> SEQ ID NO 58
<211> LENGTH: 11
<212> TYPE: PRT
<213> ORGANISM: Homo sapiens
<220> FEATURE:
<223> OTHER INFORMATION: Antibody 07

<400> SEQUENCE: 58

Arg Ala Ser Gln Gly Ile Ser Ser Trp Leu Ala
1               5                   10

<210> SEQ ID NO 59
<211> LENGTH: 7
<212> TYPE: PRT
<213> ORGANISM: Homo sapiens
<220> FEATURE:
<223> OTHER INFORMATION: Antibody 07

<400> SEQUENCE: 59

Lys Ala Ser Thr Leu Glu Ser
1               5

<210> SEQ ID NO 60
<211> LENGTH: 8
<212> TYPE: PRT
<213> ORGANISM: Homo sapiens
<220> FEATURE:
<223> OTHER INFORMATION: Antibody 07

<400> SEQUENCE: 60

Gln Gln Ser Trp Leu Gly Gly Ser
1               5

<210> SEQ ID NO 61
<211> LENGTH: 360
<212> TYPE: DNA
<213> ORGANISM: Homo sapiens
<220> FEATURE:
<223> OTHER INFORMATION: Antibody 08

<400> SEQUENCE: 61
gaagtgcagc tggtgcagtc tgggggaggc ttgatccagc cggggggtc cctgagactc      60 tcctgtgcag cctctgggtt caccatcagc agcaactaca tgatttgggt ccgtcaggct    120
ccagggaagg gctggagtg gtctccgat ctttattatt atgctggtga cacatattac      180
gcagactccg tgaagggccg attcaccatg tccagagaca tttccaagaa caccgtgtat    240
cttcaaatga acagcctgag agccgaggac acgggtgtct attattgtgc gagatgggcc    300
gatgaccacc cccggtacat cgaccactgg ggcaggggca cctggtcac cgtctcgagt    360
```

<210> SEQ ID NO 62
<211> LENGTH: 120
<212> TYPE: PRT
<213> ORGANISM: Homo sapiens
<220> FEATURE:
<223> OTHER INFORMATION: Antibody 08

<400> SEQUENCE: 62

Glu Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Ile Ser Ser Asn
            20                  25                  30

Tyr Met Ile Trp Val Arg Gln Ala Pro Gly Lys Gly Leu Glu Trp Val
        35                  40                  45

Ser Asp Leu Tyr Tyr Tyr Ala Gly Asp Thr Tyr Tyr Ala Asp Ser Val
    50                  55                  60

Lys Gly Arg Phe Thr Met Ser Arg Asp Ile Ser Lys Asn Thr Val Tyr
65                  70                  75                  80

Leu Gln Met Asn Ser Leu Arg Ala Glu Asp Thr Gly Val Tyr Tyr Cys
                85                  90                  95

Ala Arg Trp Ala Asp Asp His Pro Arg Tyr Ile Asp His Trp Gly Arg
            100                 105                 110

Gly Thr Leu Val Thr Val Ser Ser
        115                 120

<210> SEQ ID NO 63
<211> LENGTH: 5
<212> TYPE: PRT
<213> ORGANISM: Homo sapiens
<220> FEATURE:
<223> OTHER INFORMATION: Antibody 08

<400> SEQUENCE: 63

Ser Asn Tyr Met Ile
1               5

<210> SEQ ID NO 64
<211> LENGTH: 17
<212> TYPE: PRT
<213> ORGANISM: Homo sapiens
<220> FEATURE:
<223> OTHER INFORMATION: Antibody 08

<400> SEQUENCE: 64

Asp Leu Tyr Tyr Tyr Ala Gly Asp Thr Tyr Tyr Ala Asp Ser Val Lys
1               5                   10                  15

Gly

<210> SEQ ID NO 65
<211> LENGTH: 11
<212> TYPE: PRT
<213> ORGANISM: Homo sapiens
<220> FEATURE:
<223> OTHER INFORMATION: Antibody 08

<400> SEQUENCE: 65

Trp Ala Asp Asp His Pro Arg Tyr Ile Asp His
1               5                   10

<210> SEQ ID NO 66
<211> LENGTH: 321
<212> TYPE: DNA
<213> ORGANISM: Homo sapiens

```
<220> FEATURE:
<223> OTHER INFORMATION: Antibody 08

<400> SEQUENCE: 66
gacatcgtga tgacccagtc tccttccacc ctgtctgcat ctgtaggaga cagagtcacc      60
atcacttgcc gggccagtca gggtattagt agctggttgg cctggtatca gcagaaacca     120
gggagagccc ctaaggtctt gatctataag gcatctactt tagaaagtgg ggtcccatca     180
aggttcagcg gcagtggatc tgggacagat ttcactctca ccatcagcag tctgcaacct     240
gaagattttg caacttacta ctgtcaacag agttggctcg gcgggtcgtt cggccaaggg     300
accaagctgg agatcaaacg t                                               321

<210> SEQ ID NO 67
<211> LENGTH: 107
<212> TYPE: PRT
<213> ORGANISM: Homo sapiens
<220> FEATURE:
<223> OTHER INFORMATION: Antibody 08

<400> SEQUENCE: 67

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Leu Gly Gly Ser
                85                  90                  95

Phe Gly Gln Gly Thr Lys Leu Glu Ile Lys Arg
            100                 105

<210> SEQ ID NO 68
<211> LENGTH: 11
<212> TYPE: PRT
<213> ORGANISM: Homo sapiens
<220> FEATURE:
<223> OTHER INFORMATION: Antibody 08

<400> SEQUENCE: 68

Arg Ala Ser Gln Gly Ile Ser Ser Trp Leu Ala
1               5                   10

<210> SEQ ID NO 69
<211> LENGTH: 7
<212> TYPE: PRT
<213> ORGANISM: Homo sapiens
<220> FEATURE:
<223> OTHER INFORMATION: Antibody 08

<400> SEQUENCE: 69

Lys Ala Ser Thr Leu Glu Ser
1               5

<210> SEQ ID NO 70
<211> LENGTH: 8
<212> TYPE: PRT
<213> ORGANISM: Homo sapiens
```

```
<220> FEATURE:
<223> OTHER INFORMATION: Antibody 08

<400> SEQUENCE: 70

Gln Gln Ser Trp Leu Gly Gly Ser
1               5

<210> SEQ ID NO 71
<211> LENGTH: 360
<212> TYPE: DNA
<213> ORGANISM: Homo sapiens
<220> FEATURE:
<223> OTHER INFORMATION: Antibody 10

<400> SEQUENCE: 71
gaggtgcagc tggtggagtc tgggggaggc ttggtccagc cggggggtc cctgagactc      60 tcctgtgcag cctctgggtt caccatcagc agcaactaca tgatttgggt ccgtcaggct    120
ccagggaagg gctggagtg gtctccgat ctttattatt atgctggtga cacatattac      180
gcagactccg tgaagggccg attcaccatg tccagagaca tttccaagaa caccgtgtat    240
cttcaaatga acagcctgag agccgaggac acggctgtct attattgtgc gagatgggag    300
gaggagggga gggggtacat tgacgtctgg ggcaggggca ccctggtcac cgtctcctca    360

<210> SEQ ID NO 72
<211> LENGTH: 120
<212> TYPE: PRT
<213> ORGANISM: Homo sapiens
<220> FEATURE:
<223> OTHER INFORMATION: Antibody 10

<400> SEQUENCE: 72

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Ile Ser Ser Asn
            20                  25                  30

Tyr Met Ile Trp Val Arg Gln Ala Pro Gly Lys Gly Leu Glu Trp Val
        35                  40                  45

Ser Asp Leu Tyr Tyr Ala Gly Asp Thr Tyr Tyr Ala Asp Ser Val
    50                  55                  60

Lys Gly Arg Phe Thr Met Ser Arg Asp Ile Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Trp Glu Glu Glu Gly Arg Gly Tyr Ile Asp Val Trp Gly Arg
            100                 105                 110

Gly Thr Leu Val Thr Val Ser Ser
        115                 120

<210> SEQ ID NO 73
<211> LENGTH: 5
<212> TYPE: PRT
<213> ORGANISM: Homo sapiens
<220> FEATURE:
<223> OTHER INFORMATION: Antibody 10

<400> SEQUENCE: 73

Ser Asn Tyr Met Ile
1               5

<210> SEQ ID NO 74
```

<211> LENGTH: 17
<212> TYPE: PRT
<213> ORGANISM: Homo sapiens
<220> FEATURE:
<223> OTHER INFORMATION: Antibody 10

<400> SEQUENCE: 74

Asp Leu Tyr Tyr Tyr Ala Gly Asp Thr Tyr Tyr Ala Asp Ser Val Lys
1               5                   10                  15
Gly

<210> SEQ ID NO 75
<211> LENGTH: 11
<212> TYPE: PRT
<213> ORGANISM: Homo sapiens
<220> FEATURE:
<223> OTHER INFORMATION: Antibody 10

<400> SEQUENCE: 75

Trp Glu Glu Glu Gly Arg Gly Tyr Ile Asp Val
1               5                   10

<210> SEQ ID NO 76
<211> LENGTH: 321
<212> TYPE: DNA
<213> ORGANISM: Homo sapiens
<220> FEATURE:
<223> OTHER INFORMATION: Antibody 10

<400> SEQUENCE: 76

```
gacatccaga tgacccagtc tccttccacc ctgtctgcat ctgtaggaga cagagtcacc      60
atcacttgcc gggccagtca gggtattagt agctggttgg cctggtatca gcagaaacca     120
gggaaagccc ctaaggtctt gatctataag gcatctactt tagaaagtgg ggtcccatca     180
aggttcagcg gcagtggatc tgggacagaa ttcactctca ccatcagcag tctgcaacct     240
gatgattttg caacttacta ctgtcaacag agttggctcg gcgggtcgtt cggccaaggg     300
accaagctgg agatcaaacg t                                               321
```

<210> SEQ ID NO 77
<211> LENGTH: 107
<212> TYPE: PRT
<213> ORGANISM: Homo sapiens
<220> FEATURE:
<223> OTHER INFORMATION: Antibody 10

<400> SEQUENCE: 77

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Trp Leu Gly Gly Ser
                85                  90                  95

Phe Gly Gln Gly Thr Lys Leu Glu Ile Lys Arg
            100                 105

<210> SEQ ID NO 78
<211> LENGTH: 11
<212> TYPE: PRT
<213> ORGANISM: Homo sapiens
<220> FEATURE:
<223> OTHER INFORMATION: Antibody 10

<400> SEQUENCE: 78

Arg Ala Ser Gln Gly Ile Ser Ser Trp Leu Ala
1               5                   10

<210> SEQ ID NO 79
<211> LENGTH: 7
<212> TYPE: PRT
<213> ORGANISM: Homo sapiens
<220> FEATURE:
<223> OTHER INFORMATION: Antibody 10

<400> SEQUENCE: 79

Lys Ala Ser Thr Leu Glu Ser
1               5

<210> SEQ ID NO 80
<211> LENGTH: 8
<212> TYPE: PRT
<213> ORGANISM: Homo sapiens
<220> FEATURE:
<223> OTHER INFORMATION: Antibody 10

<400> SEQUENCE: 80

Gln Gln Ser Trp Leu Gly Gly Ser
1               5

<210> SEQ ID NO 81
<211> LENGTH: 363
<212> TYPE: DNA
<213> ORGANISM: Homo sapiens
<220> FEATURE:
<223> OTHER INFORMATION: Antibody 14

<400> SEQUENCE: 81
gaagtgcagc tggtgcagtc tgggggaggc ttgatccagc cggggggtc cctgagactc       60 tcctgtgcag cctctgggtt caccatcagc agcaactaca tgatttgggt ccgtcaggct      120
ccagggaagg ggctggagtg ggtctccgat ctttattatt atgctggtga cacatattac      180
gcagactccg tgaagggccg attcaccatg tccagagaca tttccaagaa caccgtgtat      240
cttcaaatga acagcctgag agccgaggac acgggtgtct attattgtgc gagatgggcc      300
gatgaccaca actaccccca cattgacgtc tggggcaggg gcaccctggt caccgtctcg      360
agt                                                                    363

<210> SEQ ID NO 82
<211> LENGTH: 121
<212> TYPE: PRT
<213> ORGANISM: Homo sapiens
<220> FEATURE:
<223> OTHER INFORMATION: Antibody 14

<400> SEQUENCE: 82

Glu Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Ile Ser Ser Asn
            20                  25                  30

Tyr Met Ile Trp Val Arg Gln Ala Pro Gly Lys Gly Leu Glu Trp Val
                35                  40                  45

Ser Asp Leu Tyr Tyr Ala Gly Asp Thr Tyr Tyr Ala Asp Ser Val
 50                  55                  60

Lys Gly Arg Phe Thr Met Ser Arg Asp Ile Ser Lys Asn Thr Val Tyr
 65                  70                  75                  80

Leu Gln Met Asn Ser Leu Arg Ala Glu Asp Thr Gly Val Tyr Tyr Cys
                 85                  90                  95

Ala Arg Trp Ala Asp Asp His Asn Tyr Pro His Ile Asp Val Trp Gly
                100                 105                 110

Arg Gly Thr Leu Val Thr Val Ser Ser
        115                 120

<210> SEQ ID NO 83
<211> LENGTH: 5
<212> TYPE: PRT
<213> ORGANISM: Homo sapiens
<220> FEATURE:
<223> OTHER INFORMATION: Antibody 14

<400> SEQUENCE: 83

Ser Asn Tyr Met Ile
 1               5

<210> SEQ ID NO 84
<211> LENGTH: 17
<212> TYPE: PRT
<213> ORGANISM: Homo sapiens
<220> FEATURE:
<223> OTHER INFORMATION: Antibody 14

<400> SEQUENCE: 84

Asp Leu Tyr Tyr Tyr Ala Gly Asp Thr Tyr Tyr Ala Asp Ser Val Lys
 1               5                  10                  15

Gly

<210> SEQ ID NO 85
<211> LENGTH: 12
<212> TYPE: PRT
<213> ORGANISM: Homo sapiens
<220> FEATURE:
<223> OTHER INFORMATION: Antibody 14

<400> SEQUENCE: 85

Trp Ala Asp Asp His Asn Tyr Pro His Ile Asp Val
 1               5                  10

<210> SEQ ID NO 86
<211> LENGTH: 324
<212> TYPE: DNA
<213> ORGANISM: Homo sapiens
<220> FEATURE:
<223> OTHER INFORMATION: Antibody 14

<400> SEQUENCE: 86
gacatcgtga tgacccagtc tccttccacc ctgtctgcat ctgtaggaga cagagtcacc      60
atcacttgcc gggccagtca gggtattagt agctggttgg cctggtatca gcagaaacca    120
gggagagccc ctaaggtctt gatctataag gcatctactt tagaaagtgg ggtcccatca    180
aggttcagcg gcagtggatc tgggacagat tcactctca ccatcagcag tctgcaacct    240
gaagattttg caacttacta ctgtgccgcc cactacgccg ccccgtggac gttcggccaa    300
gggaccaagc tggagatcaa acgt                                          324

<210> SEQ ID NO 87
<211> LENGTH: 108
<212> TYPE: PRT
<213> ORGANISM: Homo sapiens
<220> FEATURE:
<223> OTHER INFORMATION: Antibody 14

<400> SEQUENCE: 87

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Ala His Tyr Ala Ala Pro Trp
                85                  90                  95

Thr Phe Gly Gln Gly Thr Lys Leu Glu Ile Lys Arg
            100                 105

<210> SEQ ID NO 88
<211> LENGTH: 11
<212> TYPE: PRT
<213> ORGANISM: Homo sapiens
<220> FEATURE:
<223> OTHER INFORMATION: Antibody 14

<400> SEQUENCE: 88

Arg Ala Ser Gln Gly Ile Ser Ser Trp Leu Ala
1               5                   10

<210> SEQ ID NO 89
<211> LENGTH: 7
<212> TYPE: PRT
<213> ORGANISM: Homo sapiens
<220> FEATURE:
<223> OTHER INFORMATION: Antibody 14

<400> SEQUENCE: 89

Lys Ala Ser Thr Leu Glu Ser
1               5

<210> SEQ ID NO 90
<211> LENGTH: 9
<212> TYPE: PRT
<213> ORGANISM: Homo sapiens
<220> FEATURE:
<223> OTHER INFORMATION: Antibody 14

<400> SEQUENCE: 90

Ala Ala His Tyr Ala Ala Pro Trp Thr
1               5

<210> SEQ ID NO 91
<211> LENGTH: 360
<212> TYPE: DNA
<213> ORGANISM: Homo sapiens
<220> FEATURE:
<223> OTHER INFORMATION: Antibody 16

<400> SEQUENCE: 91

```
gaagtgcagc tggtgcagtc tgggggaggc ttgatccagc cggggggtc cctgagactc    60
tcctgtgcag cctctgggtt caccatcagc agcaactaca tgatttgggt ccgtcaggct   120
ccagggaagg ggctggagtg ggtctccgat ctttattatt atgctggtga cacatattac   180
gcagactctg tgaagggccg attcaccatg tccagagaca tttccaagaa caccgtgtat   240
cttcaaatga acagcctgag agccgaggac acgggtgtct attattgtgc gagatgggcc   300
gatgaccacc cccctacat cgacctgtgg ggcaggggca ccctggtcac cgtctcgagt    360
```

<210> SEQ ID NO 92
<211> LENGTH: 120
<212> TYPE: PRT
<213> ORGANISM: Homo sapiens
<220> FEATURE:
<223> OTHER INFORMATION: Antibody 16

<400> SEQUENCE: 92

```
Glu Val Gln Leu Val Gln Ser Gly Gly Gly Leu Ile Gln Pro Gly Gly
1               5                   10                  15
Ser Leu Arg Leu Ser Cys Ala Ala Ser Gly Phe Thr Ile Ser Ser Asn
            20                  25                  30
Tyr Met Ile Trp Val Arg Gln Ala Pro Gly Lys Gly Leu Glu Trp Val
        35                  40                  45
Ser Asp Leu Tyr Tyr Tyr Ala Gly Asp Thr Tyr Tyr Ala Asp Ser Val
    50                  55                  60
Lys Gly Arg Phe Thr Met Ser Arg Asp Ile Ser Lys Asn Thr Val Tyr
65                  70                  75                  80
Leu Gln Met Asn Ser Leu Arg Ala Glu Asp Thr Gly Val Tyr Tyr Cys
                85                  90                  95
Ala Arg Trp Ala Asp Asp His Pro Pro Tyr Ile Asp Leu Trp Gly Arg
            100                 105                 110
Gly Thr Leu Val Thr Val Ser Ser
        115                 120
```

<210> SEQ ID NO 93
<211> LENGTH: 5
<212> TYPE: PRT
<213> ORGANISM: Homo sapiens
<220> FEATURE:
<223> OTHER INFORMATION: Antibody 16

<400> SEQUENCE: 93

```
Ser Asn Tyr Met Ile
1               5
```

<210> SEQ ID NO 94
<211> LENGTH: 17
<212> TYPE: PRT
<213> ORGANISM: Homo sapiens
<220> FEATURE:
<223> OTHER INFORMATION: Antibody 16

<400> SEQUENCE: 94

```
Asp Leu Tyr Tyr Tyr Ala Gly Asp Thr Tyr Tyr Ala Asp Ser Val Lys
1               5                   10                  15
Gly
```

<210> SEQ ID NO 95

<211> LENGTH: 11
<212> TYPE: PRT
<213> ORGANISM: Homo sapiens
<220> FEATURE:
<223> OTHER INFORMATION: Antibody 16

<400> SEQUENCE: 95

Trp Ala Asp Asp His Pro Pro Tyr Ile Asp Leu
1               5                   10

<210> SEQ ID NO 96
<211> LENGTH: 321
<212> TYPE: DNA
<213> ORGANISM: Homo sapiens
<220> FEATURE:
<223> OTHER INFORMATION: Antibody 16

<400> SEQUENCE: 96

```
gacatcgtga tgacccagtc tccttccacc ctgtctgcat ctgtaggaga cagagtcacc    60
atcacttgcc gggccagtca gggtattagt agctggttgg cctggtatca gcagaaacca   120
gggagagccc ctaaggtctt gatctataag gcatctactt tagaaagtgg ggtcccatca   180
aggttcagcg gcagtggatc tgggacagat ttcactctca ccatcagcag tctgcaacct   240
gaagattttg caacttacta ctgtcaacag agttggctcg gcgggtcgtt cggccaaggg   300
accaagctgg agatcaaacg t                                             321
```

<210> SEQ ID NO 97
<211> LENGTH: 107
<212> TYPE: PRT
<213> ORGANISM: Homo sapiens
<220> FEATURE:
<223> OTHER INFORMATION: Antibody 16

<400> SEQUENCE: 97

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Leu Gly Gly Ser
                85                  90                  95

Phe Gly Gln Gly Thr Lys Leu Glu Ile Lys Arg
            100                 105

<210> SEQ ID NO 98
<211> LENGTH: 11
<212> TYPE: PRT
<213> ORGANISM: Homo sapiens
<220> FEATURE:
<223> OTHER INFORMATION: Antibody 16

<400> SEQUENCE: 98

Arg Ala Ser Gln Gly Ile Ser Ser Trp Leu Ala
1               5                   10

<210> SEQ ID NO 99

```
<211> LENGTH: 7
<212> TYPE: PRT
<213> ORGANISM: Homo sapiens
<220> FEATURE:
<223> OTHER INFORMATION: Antibody 16

<400> SEQUENCE: 99

Lys Ala Ser Thr Leu Glu Ser
1               5

<210> SEQ ID NO 100
<211> LENGTH: 8
<212> TYPE: PRT
<213> ORGANISM: Homo sapiens
<220> FEATURE:
<223> OTHER INFORMATION: Antibody 16

<400> SEQUENCE: 100

Gln Gln Ser Trp Leu Gly Gly Ser
1               5

<210> SEQ ID NO 101
<211> LENGTH: 360
<212> TYPE: DNA
<213> ORGANISM: Homo sapiens
<220> FEATURE:
<223> OTHER INFORMATION: Antibody 17

<400> SEQUENCE: 101
gaggtgcagc tggtggagtc tgggggaggc ttggtccagc cggggggtc cctgagactc      60 tcctgtgcag cctctgggtt caccatcagc agcaactaca tgatttgggt ccgtcaggct    120
ccagggaagg gctggagtg gtctccgat ctttattatt atgctggtga cacatattac      180
gcagactccg tgaagggccg attcaccatg tccagagaca tttccaagaa caccgtgtat    240
cttcaaatga acagcctgag agccgaggac acggctgtct attattgtgc gagatgggcc    300
gatgaccacc cccctacat cgacatgtgg ggcagggggca ccctggtcac cgtctcctca    360

<210> SEQ ID NO 102
<211> LENGTH: 120
<212> TYPE: PRT
<213> ORGANISM: Homo sapiens
<220> FEATURE:
<223> OTHER INFORMATION: Antibody 17

<400> SEQUENCE: 102

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Asn
            20                  25                  30

Tyr Met Ile Trp Val Arg Gln Ala Pro Gly Lys Gly Leu Glu Trp Val
        35                  40                  45

Ser Asp Leu Tyr Tyr Tyr Ala Gly Asp Thr Tyr Tyr Ala Asp Ser Val
    50                  55                  60

Lys Gly Arg Phe Thr Met Ser Arg Asp Ile Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Trp Ala Asp Asp His Pro Pro Tyr Ile Asp Met Trp Gly Arg
            100                 105                 110

Gly Thr Leu Val Thr Val Ser Ser
        115                 120
```

<210> SEQ ID NO 103
<211> LENGTH: 5
<212> TYPE: PRT
<213> ORGANISM: Homo sapiens
<220> FEATURE:
<223> OTHER INFORMATION: Antibody 17

<400> SEQUENCE: 103

Ser Asn Tyr Met Ile
1               5

<210> SEQ ID NO 104
<211> LENGTH: 17
<212> TYPE: PRT
<213> ORGANISM: Homo sapiens
<220> FEATURE:
<223> OTHER INFORMATION: Antibody 17

<400> SEQUENCE: 104

Asp Leu Tyr Tyr Tyr Ala Gly Asp Thr Tyr Tyr Ala Asp Ser Val Lys
1               5                   10                  15

Gly

<210> SEQ ID NO 105
<211> LENGTH: 11
<212> TYPE: PRT
<213> ORGANISM: Homo sapiens
<220> FEATURE:
<223> OTHER INFORMATION: Antibody 17

<400> SEQUENCE: 105

Trp Ala Asp Asp His Pro Pro Tyr Ile Asp Met
1               5                   10

<210> SEQ ID NO 106
<211> LENGTH: 321
<212> TYPE: DNA
<213> ORGANISM: Homo sapiens
<220> FEATURE:
<223> OTHER INFORMATION: Antibody 17

<400> SEQUENCE: 106
gacatccaga tgacccagtc tccttccacc ctgtctgcat ctgtaggaga cagagtcacc      60
atcacttgcc gggccagtca gggtattagt agctggttgg cctggtatca gcagaaacca    120
gggaaagccc ctaaggtctt gatctataag gcatcactt tagaaagtgg ggtcccatca     180
aggttcagcg gcagtggatc tgggacagaa ttcactctca ccatcagcag tctgcaacct    240
gatgattttg caacttacta ctgtcaacag agttggctcg gcgggtcgtt cggccaaggg    300
accaagctgg agatcaaacg t                                              321

<210> SEQ ID NO 107
<211> LENGTH: 107
<212> TYPE: PRT
<213> ORGANISM: Homo sapiens
<220> FEATURE:
<223> OTHER INFORMATION: Antibody 17

<400> SEQUENCE: 107

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

```
Leu Ala Trp Tyr Gln Gln Lys Pro Gly Lys Ala Pro Lys Val Leu Ile
            35                  40                  45
Tyr Lys Ala Ser Thr Leu Glu Ser Gly Val Pro Ser Arg Phe Ser Gly
        50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln Ser Trp Leu Gly Gly Ser
                85                  90                  95
Phe Gly Gln Gly Thr Lys Leu Glu Ile Lys Arg
            100                 105
```

<210> SEQ ID NO 108
<211> LENGTH: 11
<212> TYPE: PRT
<213> ORGANISM: Homo sapiens
<220> FEATURE:
<223> OTHER INFORMATION: Antibody 17

<400> SEQUENCE: 108

```
Arg Ala Ser Gln Gly Ile Ser Ser Trp Leu Ala
1               5                   10
```

<210> SEQ ID NO 109
<211> LENGTH: 7
<212> TYPE: PRT
<213> ORGANISM: Homo sapiens
<220> FEATURE:
<223> OTHER INFORMATION: Antibody 17

<400> SEQUENCE: 109

```
Lys Ala Ser Thr Leu Glu Ser
1               5
```

<210> SEQ ID NO 110
<211> LENGTH: 8
<212> TYPE: PRT
<213> ORGANISM: Homo sapiens
<220> FEATURE:
<223> OTHER INFORMATION: Antibody 17

<400> SEQUENCE: 110

```
Gln Gln Ser Trp Leu Gly Gly Ser
1               5
```

<210> SEQ ID NO 111
<211> LENGTH: 360
<212> TYPE: DNA
<213> ORGANISM: Homo sapiens
<220> FEATURE:
<223> OTHER INFORMATION: Antibody 18

<400> SEQUENCE: 111

```
gaggtgcagc tggtggagtc tgggggaggc ttggtccagc cggggggtc cctgagactc      60 tcctgtgcag cctctgggtt caccatcagc agcaactaca tgatttgggt ccgtcaggct    120
ccagggaagg ggctggagtg ggtctccgat ctttattatt atgctggtga cacatattac    180
gcagactccg tgaagggccg attcaccatg tccagagaca tttccaagaa caccgtgtat    240
cttcaaatga acagcctgag agccgaggac acggctgtct attattgtgc gagatgggcc    300
gatgaccacc cccctggat cgacctctgg ggcaggggca cctggtcac cgtctcctca      360
```

<210> SEQ ID NO 112

```
<211> LENGTH: 120
<212> TYPE: PRT
<213> ORGANISM: Homo sapiens
<220> FEATURE:
<223> OTHER INFORMATION: Antibody 18

<400> SEQUENCE: 112

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Asn
            20                  25                  30

Tyr Met Ile Trp Val Arg Gln Ala Pro Gly Lys Gly Leu Glu Trp Val
        35                  40                  45

Ser Asp Leu Tyr Tyr Tyr Ala Gly Asp Thr Tyr Tyr Ala Asp Ser Val
    50                  55                  60

Lys Gly Arg Phe Thr Met Ser Arg Asp Ile Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Trp Ala Asp Asp His Pro Pro Trp Ile Asp Leu Trp Gly Arg
            100                 105                 110

Gly Thr Leu Val Thr Val Ser Ser
        115                 120

<210> SEQ ID NO 113
<211> LENGTH: 5
<212> TYPE: PRT
<213> ORGANISM: Homo sapiens
<220> FEATURE:
<223> OTHER INFORMATION: Antibody 18

<400> SEQUENCE: 113

Ser Asn Tyr Met Ile
1               5

<210> SEQ ID NO 114
<211> LENGTH: 17
<212> TYPE: PRT
<213> ORGANISM: Homo sapiens
<220> FEATURE:
<223> OTHER INFORMATION: Antibody 18

<400> SEQUENCE: 114

Asp Leu Tyr Tyr Tyr Ala Gly Asp Thr Tyr Tyr Ala Asp Ser Val Lys
1               5                   10                  15

Gly

<210> SEQ ID NO 115
<211> LENGTH: 11
<212> TYPE: PRT
<213> ORGANISM: Homo sapiens
<220> FEATURE:
<223> OTHER INFORMATION: Antibody 18

<400> SEQUENCE: 115

Trp Ala Asp Asp His Pro Pro Trp Ile Asp Leu
1               5                   10

<210> SEQ ID NO 116
<211> LENGTH: 321
<212> TYPE: DNA
<213> ORGANISM: Homo sapiens
<220> FEATURE:
```

<223> OTHER INFORMATION: Antibody 18

<400> SEQUENCE: 116

```
gacatccaga tgacccagtc tccttccacc ctgtctgcat ctgtaggaga cagagtcacc    60
atcacttgcc gggccagtca gggtattagt agctggttgg cctggtatca gcagaaacca   120
gggaaagccc ctaaggtctt gatctataag gcatctactt tagaaagtgg ggtcccatca   180
aggttcagcg gcagtggatc tgggacagaa ttcactctca ccatcagcag tctgcaacct   240
gatgattttg caacttacta ctgtcaacag agttggctcg gcgggtcgtt cggccaaggg   300
accaagctgg agatcaaacg t                                             321
```

<210> SEQ ID NO 117
<211> LENGTH: 107
<212> TYPE: PRT
<213> ORGANISM: Homo sapiens
<220> FEATURE:
<223> OTHER INFORMATION: Antibody 18

<400> SEQUENCE: 117

```
Asp Ile Gln Met Thr Gln Ser Pro Ser Thr Leu Ser Ala Ser Val Gly
1               5                   10                  15
Asp Arg Val Thr Ile Thr Cys Arg Ala Ser Gln Gly Ile Ser Ser Trp
            20                  25                  30
Leu Ala Trp Tyr Gln Gln Lys Pro Gly Lys Ala Pro Lys Val Leu Ile
        35                  40                  45
Tyr Lys Ala Ser Thr Leu Glu Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln Ser Trp Leu Gly Gly Ser
                85                  90                  95
Phe Gly Gln Gly Thr Lys Leu Glu Ile Lys Arg
            100                 105
```

<210> SEQ ID NO 118
<211> LENGTH: 11
<212> TYPE: PRT
<213> ORGANISM: Homo sapiens
<220> FEATURE:
<223> OTHER INFORMATION: Antibody 18

<400> SEQUENCE: 118

```
Arg Ala Ser Gln Gly Ile Ser Ser Trp Leu Ala
1               5                   10
```

<210> SEQ ID NO 119
<211> LENGTH: 7
<212> TYPE: PRT
<213> ORGANISM: Homo sapiens
<220> FEATURE:
<223> OTHER INFORMATION: Antibody 18

<400> SEQUENCE: 119

```
Lys Ala Ser Thr Leu Glu Ser
1               5
```

<210> SEQ ID NO 120
<211> LENGTH: 8
<212> TYPE: PRT
<213> ORGANISM: Homo sapiens
<220> FEATURE:

<223> OTHER INFORMATION: Antibody 18

<400> SEQUENCE: 120

Gln Gln Ser Trp Leu Gly Gly Ser
1               5

<210> SEQ ID NO 121
<211> LENGTH: 360
<212> TYPE: DNA
<213> ORGANISM: Homo sapiens
<220> FEATURE:
<223> OTHER INFORMATION: Antibody 19

<400> SEQUENCE: 121

```
gaagtgcagc tggtgcagtc tgggggaggc ttgatccagc cggggggtc cctgagactc      60
tcctgtgcag cctctgggtt caccatcagc agcaactaca tgatttgggt ccgtcaggct    120
ccagggaagg ggctggagtg ggtctccgat ctttattatt atgctggtga cacatattac    180
gcagactccg tgaagggccg attcaccatg tccagagaca tttccaagaa caccgtgtat    240
cttcaaatga acagcctgag agccgaggac acgggtgtct attattgtgc gagatgggcc    300
gatgaccacc cctcccacct cgacatctgg ggcaggggca ccctggtcac cgtctcgagt    360
```

<210> SEQ ID NO 122
<211> LENGTH: 120
<212> TYPE: PRT
<213> ORGANISM: Homo sapiens
<220> FEATURE:
<223> OTHER INFORMATION: Antibody 19

<400> SEQUENCE: 122

Glu Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Ile Ser Ser Asn
            20                  25                  30

Tyr Met Ile Trp Val Arg Gln Ala Pro Gly Lys Gly Leu Glu Trp Val
        35                  40                  45

Ser Asp Leu Tyr Tyr Tyr Ala Gly Asp Thr Tyr Tyr Ala Asp Ser Val
    50                  55                  60

Lys Gly Arg Phe Thr Met Ser Arg Asp Ile Ser Lys Asn Thr Val Tyr
65                  70                  75                  80

Leu Gln Met Asn Ser Leu Arg Ala Glu Asp Thr Gly Val Tyr Tyr Cys
                85                  90                  95

Ala Arg Trp Ala Asp Asp His Pro Ser His Leu Asp Ile Trp Gly Arg
            100                 105                 110

Gly Thr Leu Val Thr Val Ser Ser
        115                 120

<210> SEQ ID NO 123
<211> LENGTH: 5
<212> TYPE: PRT
<213> ORGANISM: Homo sapiens
<220> FEATURE:
<223> OTHER INFORMATION: Antibody 19

<400> SEQUENCE: 123

Ser Asn Tyr Met Ile
1               5

<210> SEQ ID NO 124
<211> LENGTH: 17

```
<212> TYPE: PRT
<213> ORGANISM: Homo sapiens
<220> FEATURE:
<223> OTHER INFORMATION: Antibody 19

<400> SEQUENCE: 124

Asp Leu Tyr Tyr Tyr Ala Gly Asp Thr Tyr Tyr Ala Asp Ser Val Lys
1               5                   10                  15

Gly

<210> SEQ ID NO 125
<211> LENGTH: 11
<212> TYPE: PRT
<213> ORGANISM: Homo sapiens
<220> FEATURE:
<223> OTHER INFORMATION: Antibody 19

<400> SEQUENCE: 125

Trp Ala Asp Asp His Pro Ser His Leu Asp Ile
1               5                   10

<210> SEQ ID NO 126
<211> LENGTH: 321
<212> TYPE: DNA
<213> ORGANISM: Homo sapiens
<220> FEATURE:
<223> OTHER INFORMATION: Antibody 19

<400> SEQUENCE: 126
gacatcgtga tgacccagtc tccttccacc ctgtctgcat ctgtaggaga cagagtcacc      60
atcacttgcc gggccagtca gggtattagt agctggttgg cctggtatca gcagaaacca    120
gggagagccc ctaaggtctt gatctataag gcatctactt tagaaagtgg ggtcccatca    180
aggttcagcg gcagtggatc tgggacagat ttcactctca ccatcagcag tctgcaacct    240
gaagattttg caacttacta ctgtcaacag agttggctcg gcgggtcgtt cggccaaggg    300
accaagctgg agatcaaacg t                                              321

<210> SEQ ID NO 127
<211> LENGTH: 107
<212> TYPE: PRT
<213> ORGANISM: Homo sapiens
<220> FEATURE:
<223> OTHER INFORMATION: Antibody 19

<400> SEQUENCE: 127

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Leu Gly Gly Ser
                85                  90                  95

Phe Gly Gln Gly Thr Lys Leu Glu Ile Lys Arg
            100                 105
```

<210> SEQ ID NO 128
<211> LENGTH: 11
<212> TYPE: PRT
<213> ORGANISM: Homo sapiens
<220> FEATURE:
<223> OTHER INFORMATION: Antibody 19

<400> SEQUENCE: 128

Arg Ala Ser Gln Gly Ile Ser Ser Trp Leu Ala
1               5                   10

<210> SEQ ID NO 129
<211> LENGTH: 7
<212> TYPE: PRT
<213> ORGANISM: Homo sapiens
<220> FEATURE:
<223> OTHER INFORMATION: Antibody 19

<400> SEQUENCE: 129

Lys Ala Ser Thr Leu Glu Ser
1               5

<210> SEQ ID NO 130
<211> LENGTH: 8
<212> TYPE: PRT
<213> ORGANISM: Homo sapiens
<220> FEATURE:
<223> OTHER INFORMATION: Antibody 19

<400> SEQUENCE: 130

Gln Gln Ser Trp Leu Gly Gly Ser
1               5

<210> SEQ ID NO 131
<211> LENGTH: 360
<212> TYPE: DNA
<213> ORGANISM: Homo sapiens
<220> FEATURE:
<223> OTHER INFORMATION: Antibody 21

<400> SEQUENCE: 131
gaagtgcagc tggtgcagtc tgggggaggc ttgatccagc cggggggtc cctgagactc      60
tcctgtgcag cctctgggtt caccatcagc agcaactaca tgatttgggt ccgtcaggct    120
ccagggaagg gctggagtg gtctccgat ctttattatt atgctggtga cacatattac      180
gcagactccg tgaagggccg attcaccatg tccagagaca tttccaagaa caccgtgtat    240
cttcaaatga acagcctgag agccgaggac acgggtgtct attattgtgc gagatggggcc   300
gatgaccacc cctcccacat tgacgtctgg ggcaggggca ccctggtcac cgtctcgagt    360

<210> SEQ ID NO 132
<211> LENGTH: 120
<212> TYPE: PRT
<213> ORGANISM: Homo sapiens
<220> FEATURE:
<223> OTHER INFORMATION: Antibody 21

<400> SEQUENCE: 132

Glu Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Ile Ser Ser Asn
            20                  25                  30

Tyr Met Ile Trp Val Arg Gln Ala Pro Gly Lys Gly Leu Glu Trp Val
        35                  40                  45

```
Ser Asp Leu Tyr Tyr Tyr Ala Gly Asp Thr Tyr Tyr Ala Asp Ser Val
    50                  55                  60
Lys Gly Arg Phe Thr Met Ser Arg Asp Ile Ser Lys Asn Thr Val Tyr
 65                  70                  75                  80
Leu Gln Met Asn Ser Leu Arg Ala Glu Asp Thr Gly Val Tyr Tyr Cys
                 85                  90                  95
Ala Arg Trp Ala Asp Asp His Pro Ser His Ile Asp Val Trp Gly Arg
            100                 105                 110
Gly Thr Leu Val Thr Val Ser Ser
            115                 120

<210> SEQ ID NO 133
<211> LENGTH: 5
<212> TYPE: PRT
<213> ORGANISM: Homo sapiens
<220> FEATURE:
<223> OTHER INFORMATION: Antibody 21

<400> SEQUENCE: 133

Ser Asn Tyr Met Ile
 1               5

<210> SEQ ID NO 134
<211> LENGTH: 17
<212> TYPE: PRT
<213> ORGANISM: Homo sapiens
<220> FEATURE:
<223> OTHER INFORMATION: Antibody 21

<400> SEQUENCE: 134

Asp Leu Tyr Tyr Tyr Ala Gly Asp Thr Tyr Tyr Ala Asp Ser Val Lys
 1               5                  10                  15
Gly

<210> SEQ ID NO 135
<211> LENGTH: 11
<212> TYPE: PRT
<213> ORGANISM: Homo sapiens
<220> FEATURE:
<223> OTHER INFORMATION: Antibody 21

<400> SEQUENCE: 135

Trp Ala Asp Asp His Pro Ser His Ile Asp Val
 1               5                  10

<210> SEQ ID NO 136
<211> LENGTH: 321
<212> TYPE: DNA
<213> ORGANISM: Homo sapiens
<220> FEATURE:
<223> OTHER INFORMATION: Antibody 21

<400> SEQUENCE: 136
gacatcgtga tgacccagtc tccttccacc ctgtctgcat ctgtaggaga cagagtcacc      60
atcacttgcc gggccagtca gggtattagt agctggttgg cctggtatca gcagaaacca     120
gggagagccc ctaaggtctt gatctataag gcatctactt tagaaagtgg ggtcccatca     180
aggttcagcg gcagtggatc tgggacagat ttcactctca ccatcagcag tctgcaacct     240
gaagattttg caacttacta ctgtcaacag agttggctcg cgggtcgtt cggccaaggg     300 accaagctgg agatcaaacg t                                              321
```

```
<210> SEQ ID NO 137
<211> LENGTH: 107
<212> TYPE: PRT
<213> ORGANISM: Homo sapiens
<220> FEATURE:
<223> OTHER INFORMATION: Antibody 21

<400> SEQUENCE: 137

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Leu Gly Gly Ser
                85                  90                  95

Phe Gly Gln Gly Thr Lys Leu Glu Ile Lys Arg
            100                 105

<210> SEQ ID NO 138
<211> LENGTH: 11
<212> TYPE: PRT
<213> ORGANISM: Homo sapiens
<220> FEATURE:
<223> OTHER INFORMATION: Antibody 21

<400> SEQUENCE: 138

Arg Ala Ser Gln Gly Ile Ser Ser Trp Leu Ala
1               5                   10

<210> SEQ ID NO 139
<211> LENGTH: 7
<212> TYPE: PRT
<213> ORGANISM: Homo sapiens
<220> FEATURE:
<223> OTHER INFORMATION: Antibody 21

<400> SEQUENCE: 139

Lys Ala Ser Thr Leu Glu Ser
1               5

<210> SEQ ID NO 140
<211> LENGTH: 8
<212> TYPE: PRT
<213> ORGANISM: Homo sapiens
<220> FEATURE:
<223> OTHER INFORMATION: Antibody 21

<400> SEQUENCE: 140

Gln Gln Ser Trp Leu Gly Gly Ser
1               5

<210> SEQ ID NO 141
<211> LENGTH: 363
<212> TYPE: DNA
<213> ORGANISM: Homo sapiens
<220> FEATURE:
<223> OTHER INFORMATION: Antibody 22

<400> SEQUENCE: 141
```

```
gaagtgcagc tggtgcagtc tgggggaggc ttgatccagc cggggggggtc cctgagactc    60 tcctgtgcag cctctgggtt caccatcagc agcaactaca tgatttgggt ccgtcaggct   120
ccagggaagg ggctggagtg ggtctccgat ctttattatt atgctggtga cacatattac   180
gcagactccg tgaagggccg attcaccatg tccagagaca tttccaagaa caccgtgtat   240
cttcaaatga acagcctgag agccgaggac acgggtgtct attattgtgc gagatgggcc   300
gatgaccaca caacaccta cattgacgtc tggggcaggg gcaccctggt caccgtctcg   360
agt                                                                 363
```

<210> SEQ ID NO 142
<211> LENGTH: 121
<212> TYPE: PRT
<213> ORGANISM: Homo sapiens
<220> FEATURE:
<223> OTHER INFORMATION: Antibody 22

<400> SEQUENCE: 142

```
Glu Val Gln Leu Val Gln Ser Gly Gly Gly Leu Ile Gln Pro Gly Gly
  1               5                  10                  15

Ser Leu Arg Leu Ser Cys Ala Ala Ser Gly Phe Thr Ile Ser Ser Asn
             20                  25                  30

Tyr Met Ile Trp Val Arg Gln Ala Pro Gly Lys Gly Leu Glu Trp Val
         35                  40                  45

Ser Asp Leu Tyr Tyr Tyr Ala Gly Asp Thr Tyr Tyr Ala Asp Ser Val
     50                  55                  60

Lys Gly Arg Phe Thr Met Ser Arg Asp Ile Ser Lys Asn Thr Val Tyr
 65                  70                  75                  80

Leu Gln Met Asn Ser Leu Arg Ala Glu Asp Thr Gly Val Tyr Tyr Cys
                 85                  90                  95

Ala Arg Trp Ala Asp Asp His Asn Asn Thr Tyr Ile Asp Val Trp Gly
            100                 105                 110

Arg Gly Thr Leu Val Thr Val Ser Ser
        115                 120
```

<210> SEQ ID NO 143
<211> LENGTH: 5
<212> TYPE: PRT
<213> ORGANISM: Homo sapiens
<220> FEATURE:
<223> OTHER INFORMATION: Antibody 22

<400> SEQUENCE: 143

```
Ser Asn Tyr Met Ile
  1               5
```

<210> SEQ ID NO 144
<211> LENGTH: 17
<212> TYPE: PRT
<213> ORGANISM: Homo sapiens
<220> FEATURE:
<223> OTHER INFORMATION: Antibody 22

<400> SEQUENCE: 144

```
Asp Leu Tyr Tyr Tyr Ala Gly Asp Thr Tyr Tyr Ala Asp Ser Val Lys
  1               5                  10                  15

Gly
```

<210> SEQ ID NO 145
<211> LENGTH: 12

```
<212> TYPE: PRT
<213> ORGANISM: Homo sapiens
<220> FEATURE:
<223> OTHER INFORMATION: Antibody 22

<400> SEQUENCE: 145

Trp Ala Asp Asp His Asn Asn Thr Tyr Ile Asp Val
1               5                   10

<210> SEQ ID NO 146
<211> LENGTH: 324
<212> TYPE: DNA
<213> ORGANISM: Homo sapiens
<220> FEATURE:
<223> OTHER INFORMATION: Antibody 22

<400> SEQUENCE: 146
gacatcgtga tgacccagtc tccttccacc ctgtctgcat ctgtaggaga cagagtcacc      60
atcacttgcc gggccagtca gggtattagt agctggttgg cctggtatca gcagaaacca     120
gggagagccc ctaaggtctt gatctataag gcatctactt tagaaagtgg ggtcccatca     180
aggttcagcg gcagtggatc tgggacagat ttcactctca ccatcagcag tctgcaacct     240
gaagattttg caacttacta ctgtgccgcc cactacgccg ccccgtggac gttcggccaa     300
gggaccaagc tggagatcaa acgt                                             324

<210> SEQ ID NO 147
<211> LENGTH: 108
<212> TYPE: PRT
<213> ORGANISM: Homo sapiens
<220> FEATURE:
<223> OTHER INFORMATION: Antibody 22

<400> SEQUENCE: 147

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Arg Ala Pro Lys Val Leu Ile
            35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Ala His Tyr Ala Ala Pro Trp
                85                  90                  95

Thr Phe Gly Gln Gly Thr Lys Leu Glu Ile Lys Arg
            100                 105

<210> SEQ ID NO 148
<211> LENGTH: 11
<212> TYPE: PRT
<213> ORGANISM: Homo sapiens
<220> FEATURE:
<223> OTHER INFORMATION: Antibody 22

<400> SEQUENCE: 148

Arg Ala Ser Gln Gly Ile Ser Ser Trp Leu Ala
1               5                   10

<210> SEQ ID NO 149
<211> LENGTH: 7
```

```
<212> TYPE: PRT
<213> ORGANISM: Homo sapiens
<220> FEATURE:
<223> OTHER INFORMATION: Antibody 22

<400> SEQUENCE: 149

Lys Ala Ser Thr Leu Glu Ser
1               5

<210> SEQ ID NO 150
<211> LENGTH: 9
<212> TYPE: PRT
<213> ORGANISM: Homo sapiens
<220> FEATURE:
<223> OTHER INFORMATION: Antibody 22

<400> SEQUENCE: 150

Ala Ala His Tyr Ala Ala Pro Trp Thr
1               5

<210> SEQ ID NO 151
<211> LENGTH: 360
<212> TYPE: DNA
<213> ORGANISM: Homo sapiens
<220> FEATURE:
<223> OTHER INFORMATION: Antibody 23

<400> SEQUENCE: 151
gaagtgcagc tggtgcagtc tgggggaggc ttgatccagc cggggggtc  cctgagactc      60 tcctgtgcag cctctgggtt caccatcagc agcaactaca tgatttgggt ccgtcaggct     120
ccagggaagg ggctggagtg ggtctccgat ctttattatt atgctggtga cacatattac     180
gcagactccg tgaagggccg attcaccatg tccagagaca tttccaagaa caccgtgtat     240
cttcaaatga acagcctgag agccgaggac acgggtgtct attattgtgc gagatgggcc     300
gatgaccacg ccccctgggt cgacctctgg ggcaggggca ccctggtcac cgtctcgagt     360

<210> SEQ ID NO 152
<211> LENGTH: 120
<212> TYPE: PRT
<213> ORGANISM: Homo sapiens
<220> FEATURE:
<223> OTHER INFORMATION: Antibody 23

<400> SEQUENCE: 152

Glu Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Ile Ser Ser Asn
            20                  25                  30

Tyr Met Ile Trp Val Arg Gln Ala Pro Gly Lys Gly Leu Glu Trp Val
        35                  40                  45

Ser Asp Leu Tyr Tyr Tyr Ala Gly Asp Thr Tyr Tyr Ala Asp Ser Val
    50                  55                  60

Lys Gly Arg Phe Thr Met Ser Arg Asp Ile Ser Lys Asn Thr Val Tyr
65                  70                  75                  80

Leu Gln Met Asn Ser Leu Arg Ala Glu Asp Thr Gly Val Tyr Tyr Cys
                85                  90                  95

Ala Arg Trp Ala Asp Asp His Ala Pro Trp Val Asp Leu Trp Gly Arg
            100                 105                 110

Gly Thr Leu Val Thr Val Ser Ser
        115                 120
```

<210> SEQ ID NO 153
<211> LENGTH: 5
<212> TYPE: PRT
<213> ORGANISM: Homo sapiens
<220> FEATURE:
<223> OTHER INFORMATION: Antibody 23

<400> SEQUENCE: 153

Ser Asn Tyr Met Ile
1               5

<210> SEQ ID NO 154
<211> LENGTH: 17
<212> TYPE: PRT
<213> ORGANISM: Homo sapiens
<220> FEATURE:
<223> OTHER INFORMATION: Antibody 23

<400> SEQUENCE: 154

Asp Leu Tyr Tyr Tyr Ala Gly Asp Thr Tyr Tyr Ala Asp Ser Val Lys
1               5                   10                  15

Gly

<210> SEQ ID NO 155
<211> LENGTH: 11
<212> TYPE: PRT
<213> ORGANISM: Homo sapiens
<220> FEATURE:
<223> OTHER INFORMATION: Antibody 23

<400> SEQUENCE: 155

Trp Ala Asp Asp His Ala Pro Trp Val Asp Leu
1               5                   10

<210> SEQ ID NO 156
<211> LENGTH: 321
<212> TYPE: DNA
<213> ORGANISM: Homo sapiens
<220> FEATURE:
<223> OTHER INFORMATION: Antibody 23

<400> SEQUENCE: 156
gacatcgtga tgacccagtc tccttccacc ctgtctgcat ctgtaggaga cagagtcacc        60
atcacttgcc gggccagtca gggtattagt agctggttgg cctggtatca gcagaaacca       120
gggagagccc ctaaggtctt gatctataag gcatctactt tagaaagtgg ggtcccatca       180
aggttcagcg gcagtggatc tgggacagat ttcactctca ccatcagcag tctgcaacct       240
gaagattttg caacttacta ctgtcaacag agttggctcg gcgggtcgtt cggccaaggg       300
accaagctgg agatcaaacg t                                                 321

<210> SEQ ID NO 157
<211> LENGTH: 107
<212> TYPE: PRT
<213> ORGANISM: Homo sapiens
<220> FEATURE:
<223> OTHER INFORMATION: Antibody 23

<400> SEQUENCE: 157

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

```
Leu Ala Trp Tyr Gln Gln Lys Pro Gly Arg Ala Pro Lys Val Leu Ile
         35                  40                  45

Tyr Lys Ala Ser Thr Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Trp Leu Gly Gly Ser
                 85                  90                  95

Phe Gly Gln Gly Thr Lys Leu Glu Ile Lys Arg
             100                 105

<210> SEQ ID NO 158
<211> LENGTH: 11
<212> TYPE: PRT
<213> ORGANISM: Homo sapiens
<220> FEATURE:
<223> OTHER INFORMATION: Antibody 23

<400> SEQUENCE: 158

Arg Ala Ser Gln Gly Ile Ser Ser Trp Leu Ala
 1               5                  10

<210> SEQ ID NO 159
<211> LENGTH: 7
<212> TYPE: PRT
<213> ORGANISM: Homo sapiens
<220> FEATURE:
<223> OTHER INFORMATION: Antibody 23

<400> SEQUENCE: 159

Lys Ala Ser Thr Leu Glu Ser
 1               5

<210> SEQ ID NO 160
<211> LENGTH: 8
<212> TYPE: PRT
<213> ORGANISM: Homo sapiens
<220> FEATURE:
<223> OTHER INFORMATION: Antibody 23

<400> SEQUENCE: 160

Gln Gln Ser Trp Leu Gly Gly Ser
 1               5

<210> SEQ ID NO 161
<211> LENGTH: 212
<212> TYPE: PRT
<213> ORGANISM: Homo sapiens
<220> FEATURE:
<223> OTHER INFORMATION: Full length IL-6

<400> SEQUENCE: 161

Met Asn Ser Phe Ser Thr Ser Ala Phe Gly Pro Val Ala Phe Ser Leu
 1               5                  10                  15

Gly Leu Leu Leu Val Leu Pro Ala Ala Phe Pro Ala Pro Val Pro Pro
                 20                  25                  30

Gly Glu Asp Ser Lys Asp Val Ala Ala Pro His Arg Gln Pro Leu Thr
             35                  40                  45

Ser Ser Glu Arg Ile Asp Lys Gln Ile Arg Tyr Ile Leu Asp Gly Ile
         50                  55                  60

Ser Ala Leu Arg Lys Glu Thr Cys Asn Lys Ser Asn Met Cys Glu Ser
 65                  70                  75                  80
```

```
Ser Lys Glu Ala Leu Ala Glu Asn Asn Leu Asn Leu Pro Lys Met Ala
                 85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
            115                 120                 125

Leu Gln Asn Arg Phe Glu Ser Ser Glu Glu Gln Ala Arg Ala Val Gln
        130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
            195                 200                 205

Leu Arg Gln Met
    210

<210> SEQ ID NO 162
<211> LENGTH: 203
<212> TYPE: PRT
<213> ORGANISM: Homo sapiens
<220> FEATURE:
<223> OTHER INFORMATION: HIS FLAG tagged IL-6

<400> SEQUENCE: 162

Met Gly Ser Ser His His His His His His Asp Tyr Lys Asp Asp Asp
1               5                   10                  15

Asp Lys His Met Val Pro Pro Gly Glu Asp Ser Lys Asp Val Ala Ala
            20                  25                  30

Pro His Arg Gln Pro Leu Thr Ser Ser Glu Arg Ile Asp Lys Gln Ile
        35                  40                  45

Arg Tyr Ile Leu Asp Gly Ile Ser Ala Leu Arg Lys Glu Thr Cys Asn
    50                  55                  60

Lys Ser Asn Met Cys Glu Ser Ser Lys Glu Ala Leu Ala Glu Asn Asn
65                  70                  75                  80

Leu Asn Leu Pro Lys Met Ala Glu Lys Asp Gly Cys Phe Gln Ser Gly
                85                  90                  95

Phe Asn Glu Glu Thr Cys Leu Val Lys Ile Ile Thr Gly Leu Leu Glu
            100                 105                 110

Phe Glu Val Tyr Leu Glu Tyr Leu Gln Asn Arg Phe Glu Ser Ser Glu
        115                 120                 125

Glu Gln Ala Arg Ala Val Gln Met Ser Thr Lys Val Leu Ile Gln Phe
    130                 135                 140

Leu Gln Lys Lys Ala Lys Asn Leu Asp Ala Ile Thr Thr Pro Asp Pro
145                 150                 155                 160

Thr Thr Asn Ala Ser Leu Leu Thr Lys Leu Gln Ala Gln Asn Gln Trp
                165                 170                 175

Leu Gln Asp Met Thr Thr His Leu Ile Leu Arg Ser Phe Lys Glu Phe
            180                 185                 190

Leu Gln Ser Ser Leu Arg Ala Leu Arg Gln Met
        195                 200

<210> SEQ ID NO 163
<211> LENGTH: 358
```

<212> TYPE: PRT
<213> ORGANISM: Homo sapiens
<220> FEATURE:
<223> OTHER INFORMATION: Soluble IL-6Ra

<400> SEQUENCE: 163

```
Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
            35                  40                  45

Gly Val Glu Pro Glu Asp Asn Ala Thr Val His Trp Val Leu Arg Lys
        50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp
        355
```

<210> SEQ ID NO 164
<211> LENGTH: 468

<212> TYPE: PRT
<213> ORGANISM: Homo sapiens
<220> FEATURE:
<223> OTHER INFORMATION: Transmembrane IL-6Ra

<400> SEQUENCE: 164

```
Met Leu Ala Val Gly Cys Ala Leu Leu Ala Ala Leu Leu Ala Ala Pro
1               5                   10                  15
Gly Ala Ala Leu Ala Pro Arg Arg Cys Pro Ala Gln Glu Val Ala Arg
                20                  25                  30
Gly Val Leu Thr Ser Leu Pro Gly Asp Ser Val Thr Leu Thr Cys Pro
            35                  40                  45
Gly Val Glu Pro Glu Asp Asn Ala Thr Val His Trp Val Leu Arg Lys
        50                  55                  60
Pro Ala Ala Gly Ser His Pro Ser Arg Trp Ala Gly Met Gly Arg Arg
65                  70                  75                  80
Leu Leu Leu Arg Ser Val Gln Leu His Asp Ser Gly Asn Tyr Ser Cys
                85                  90                  95
Tyr Arg Ala Gly Arg Pro Ala Gly Thr Val His Leu Leu Val Asp Val
                100                 105                 110
Pro Pro Glu Glu Pro Gln Leu Ser Cys Phe Arg Lys Ser Pro Leu Ser
            115                 120                 125
Asn Val Val Cys Glu Trp Gly Pro Arg Ser Thr Pro Ser Leu Thr Thr
        130                 135                 140
Lys Ala Val Leu Leu Val Arg Lys Phe Gln Asn Ser Pro Ala Glu Asp
145                 150                 155                 160
Phe Gln Glu Pro Cys Gln Tyr Ser Gln Glu Ser Gln Lys Phe Ser Cys
                165                 170                 175
Gln Leu Ala Val Pro Glu Gly Asp Ser Ser Phe Tyr Ile Val Ser Met
                180                 185                 190
Cys Val Ala Ser Ser Val Gly Ser Lys Phe Ser Lys Thr Gln Thr Phe
            195                 200                 205
Gln Gly Cys Gly Ile Leu Gln Pro Asp Pro Pro Ala Asn Ile Thr Val
        210                 215                 220
Thr Ala Val Ala Arg Asn Pro Arg Trp Leu Ser Val Thr Trp Gln Asp
225                 230                 235                 240
Pro His Ser Trp Asn Ser Ser Phe Tyr Arg Leu Arg Phe Glu Leu Arg
                245                 250                 255
Tyr Arg Ala Glu Arg Ser Lys Thr Phe Thr Thr Trp Met Val Lys Asp
                260                 265                 270
Leu Gln His His Cys Val Ile His Asp Ala Trp Ser Gly Leu Arg His
            275                 280                 285
Val Val Gln Leu Arg Ala Gln Glu Glu Phe Gly Gln Gly Glu Trp Ser
        290                 295                 300
Glu Trp Ser Pro Glu Ala Met Gly Thr Pro Trp Thr Glu Ser Arg Ser
305                 310                 315                 320
Pro Pro Ala Glu Asn Glu Val Ser Thr Pro Met Gln Ala Leu Thr Thr
                325                 330                 335
Asn Lys Asp Asp Asp Asn Ile Leu Phe Arg Asp Ser Ala Asn Ala Thr
                340                 345                 350
Ser Leu Pro Val Gln Asp Ser Ser Ser Val Pro Leu Pro Thr Phe Leu
            355                 360                 365
Val Ala Gly Gly Ser Leu Ala Phe Gly Thr Leu Leu Cys Ile Ala Ile
        370                 375                 380
```

-continued

```
Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
            420                 425                 430

Ser Pro Ser Ser Leu Gly Ser Asp Asn Thr Ser Ser His Asn Arg Pro
        435                 440                 445

Asp Ala Arg Asp Pro Arg Ser Pro Tyr Asp Ile Ser Asn Thr Asp Tyr
450                 455                 460

Phe Phe Pro Arg
465

<210> SEQ ID NO 165
<211> LENGTH: 183
<212> TYPE: PRT
<213> ORGANISM: Homo sapiens
<220> FEATURE:
<223> OTHER INFORMATION: Mature IL-6

<400> SEQUENCE: 165

Val Pro Pro Gly Glu Asp Ser Lys Asp Val Ala Ala Pro His Arg Gln
1               5                  10                  15

Pro Leu Thr Ser Ser Glu Arg Ile Asp Lys Gln Ile Arg Tyr Ile Leu
            20                  25                  30

Asp Gly Ile Ser Ala Leu Arg Lys Glu Thr Cys Asn Lys Ser Asn Met
        35                  40                  45

Cys Glu Ser Ser Lys Glu Ala Leu Ala Glu Asn Asn Leu Asn Leu Pro
    50                  55                  60

Lys Met Ala Glu Lys Asp Gly Cys Phe Gln Ser Gly Phe Asn Glu Glu
65                  70                  75                  80

Thr Cys Leu Val Lys Ile Ile Thr Gly Leu Leu Glu Phe Glu Val Tyr
                85                  90                  95

Leu Glu Tyr Leu Gln Asn Arg Phe Glu Ser Ser Glu Glu Gln Ala Arg
            100                 105                 110

Ala Val Gln Met Ser Thr Lys Val Leu Ile Gln Phe Leu Gln Lys Lys
        115                 120                 125

Ala Lys Asn Leu Asp Ala Ile Thr Thr Pro Asp Pro Thr Thr Asn Ala
    130                 135                 140

Ser Leu Leu Thr Lys Leu Gln Ala Gln Asn Gln Trp Leu Gln Asp Met
145                 150                 155                 160

Thr Thr His Leu Ile Leu Arg Ser Phe Lys Glu Phe Leu Gln Ser Ser
                165                 170                 175

Leu Arg Ala Leu Arg Gln Met
            180

<210> SEQ ID NO 166
<211> LENGTH: 918
<212> TYPE: PRT
<213> ORGANISM: Homo sapiens
<220> FEATURE:
<223> OTHER INFORMATION: Human gp130

<400> SEQUENCE: 166

Met Leu Thr Leu Gln Thr Trp Leu Val Gln Ala Leu Phe Ile Phe Leu
1               5                  10                  15

Thr Thr Glu Ser Thr Gly Glu Leu Leu Asp Pro Cys Gly Tyr Ile Ser
            20                  25                  30
```

```
Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
 50                  55                  60

Ile Val Trp Lys Thr Asn His Phe Thr Ile Pro Lys Glu Gln Tyr Thr
 65                  70                  75                  80

Ile Ile Asn Arg Thr Ala Ser Ser Val Thr Phe Thr Asp Ile Ala Ser
                 85                  90                  95

Leu Asn Ile Gln Leu Thr Cys Asn Ile Leu Thr Phe Gly Gln Leu Glu
                100                 105                 110

Gln Asn Val Tyr Gly Ile Thr Ile Ile Ser Gly Leu Pro Pro Glu Lys
                115                 120                 125

Pro Lys Asn Leu Ser Cys Ile Val Asn Glu Gly Lys Lys Met Arg Cys
130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
                180                 185                 190

Asn Ile Glu Val Trp Val Glu Ala Glu Asn Ala Leu Gly Lys Val Thr
                195                 200                 205

Ser Asp His Ile Asn Phe Asp Pro Val Tyr Lys Val Lys Pro Asn Pro
210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
                260                 265                 270

Pro Pro Glu Asp Thr Ala Ser Thr Arg Ser Ser Phe Thr Val Gln Asp
                275                 280                 285

Leu Lys Pro Phe Thr Glu Tyr Val Phe Arg Ile Arg Cys Met Lys Glu
                290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
                340                 345                 350

Thr Leu Pro Pro Phe Glu Ala Asn Gly Lys Ile Leu Asp Tyr Glu Val
                355                 360                 365

Thr Leu Thr Arg Trp Lys Ser His Leu Gln Asn Tyr Thr Val Asn Ala
                370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
                420                 425                 430

Phe Pro Lys Asp Asn Met Leu Trp Val Glu Trp Thr Thr Pro Arg Glu
                435                 440                 445
```

```
Ser Val Lys Lys Tyr Ile Leu Glu Trp Cys Val Leu Ser Asp Lys Ala
    450                 455                 460
Pro Cys Ile Thr Asp Trp Gln Gln Glu Asp Gly Thr Val His Arg Thr
465                 470                 475                 480
Tyr Leu Arg Gly Asn Leu Ala Glu Ser Lys Cys Tyr Leu Ile Thr Val
                485                 490                 495
Thr Pro Val Tyr Ala Asp Gly Pro Gly Ser Pro Glu Ser Ile Lys Ala
            500                 505                 510
Tyr Leu Lys Gln Ala Pro Pro Ser Lys Gly Pro Thr Val Arg Thr Lys
        515                 520                 525
Lys Val Gly Lys Asn Glu Ala Val Leu Glu Trp Asp Gln Leu Pro Val
    530                 535                 540
Asp Val Gln Asn Gly Phe Ile Arg Asn Tyr Thr Ile Phe Tyr Arg Thr
545                 550                 555                 560
Ile Ile Gly Asn Glu Thr Ala Val Asn Val Asp Ser Ser His Thr Glu
                565                 570                 575
Tyr Thr Leu Ser Ser Leu Thr Ser Asp Thr Leu Tyr Met Val Arg Met
            580                 585                 590
Ala Ala Tyr Thr Asp Glu Gly Gly Lys Asp Gly Pro Glu Phe Thr Phe
        595                 600                 605
Thr Thr Pro Lys Phe Ala Gln Gly Glu Ile Glu Ala Ile Val Val Pro
    610                 615                 620
Val Cys Leu Ala Phe Leu Leu Thr Thr Leu Leu Gly Val Leu Phe Cys
625                 630                 635                 640
Phe Asn Lys Arg Asp Leu Ile Lys Lys His Ile Trp Pro Asn Val Pro
                645                 650                 655
Asp Pro Ser Lys Ser His Ile Ala Gln Trp Ser Pro His Thr Pro Pro
            660                 665                 670
Arg His Asn Phe Asn Ser Lys Asp Gln Met Tyr Ser Asp Gly Asn Phe
        675                 680                 685
Thr Asp Val Ser Val Val Glu Ile Glu Ala Asn Asp Lys Lys Pro Phe
    690                 695                 700
Pro Glu Asp Leu Lys Ser Leu Asp Leu Phe Lys Lys Glu Lys Ile Asn
705                 710                 715                 720
Thr Glu Gly His Ser Ser Gly Ile Gly Gly Ser Ser Cys Met Ser Ser
                725                 730                 735
Ser Arg Pro Ser Ile Ser Ser Asp Glu Asn Glu Ser Ser Gln Asn
            740                 745                 750
Thr Ser Ser Thr Val Gln Tyr Ser Thr Val Val His Ser Gly Tyr Arg
        755                 760                 765
His Gln Val Pro Ser Val Gln Val Phe Ser Arg Ser Glu Ser Thr Gln
    770                 775                 780
Pro Leu Leu Asp Ser Glu Glu Arg Pro Glu Asp Leu Gln Leu Val Asp
785                 790                 795                 800
His Val Asp Gly Gly Asp Gly Ile Leu Pro Arg Gln Gln Tyr Phe Lys
                805                 810                 815
Gln Asn Cys Ser Gln His Glu Ser Ser Pro Asp Ile Ser His Phe Glu
            820                 825                 830
Arg Ser Lys Gln Val Ser Ser Val Asn Glu Glu Asp Phe Val Arg Leu
        835                 840                 845
Lys Gln Gln Ile Ser Asp His Ile Ser Gln Ser Cys Gly Ser Gly Gln
    850                 855                 860
Met Lys Met Phe Gln Glu Val Ser Ala Ala Asp Ala Phe Gly Pro Gly
```

```
                    865                 870                 875                 880
Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
                900                 905                 910

Gly Gly Tyr Met Pro Gln
        915

<210> SEQ ID NO 167
<211> LENGTH: 30
<212> TYPE: PRT
<213> ORGANISM: Homo sapiens
<220> FEATURE:
<223> OTHER INFORMATION: Vh3_DP-86_(3-66) FW1

<400> SEQUENCE: 167

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser
            20                  25                  30

<210> SEQ ID NO 168
<211> LENGTH: 14
<212> TYPE: PRT
<213> ORGANISM: Homo sapiens
<220> FEATURE:
<223> OTHER INFORMATION: Vh3_DP-86_(3-66) FW2

<400> SEQUENCE: 168

Trp Val Arg Gln Ala Pro Gly Lys Gly Leu Glu Trp Val Ser
1               5                   10

<210> SEQ ID NO 169
<211> LENGTH: 32
<212> TYPE: PRT
<213> ORGANISM: Homo sapiens
<220> FEATURE:
<223> OTHER INFORMATION: Vh3_DP-86_(3-66) FW3

<400> SEQUENCE: 169

Arg Phe Thr Met Ser Arg Asp Ile Ser Lys Asn Thr Val Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 170
<211> LENGTH: 11
<212> TYPE: PRT
<213> ORGANISM: Homo sapiens
<220> FEATURE:
<223> OTHER INFORMATION: Vh3_DP-86_(3-66) FW4

<400> SEQUENCE: 170

Trp Gly Arg Gly Thr Leu Val Thr Val Ser Ser
1               5                   10

<210> SEQ ID NO 171
<211> LENGTH: 23
<212> TYPE: PRT
<213> ORGANISM: Homo sapiens
<220> FEATURE:
<223> OTHER INFORMATION: Vk1_L12 FW1

<400> SEQUENCE: 171
```

```
Asp Ile Gln Met Thr Gln Ser Pro Ser Thr Leu Ser Ala Ser Val Gly
1               5                   10                  15

Asp Arg Val Thr Ile Thr Cys
            20
```

<210> SEQ ID NO 172
<211> LENGTH: 15
<212> TYPE: PRT
<213> ORGANISM: Homo sapiens
<220> FEATURE:
<223> OTHER INFORMATION: Vk1_L12 FW2

<400> SEQUENCE: 172

```
Trp Tyr Gln Gln Lys Pro Gly Lys Ala Pro Lys Val Leu Ile Tyr
1               5                   10                  15
```

<210> SEQ ID NO 173
<211> LENGTH: 32
<212> TYPE: PRT
<213> ORGANISM: Homo sapiens
<220> FEATURE:
<223> OTHER INFORMATION: Vk1_L12 FW3

<400> SEQUENCE: 173

```
Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30
```

<210> SEQ ID NO 174
<211> LENGTH: 11
<212> TYPE: PRT
<213> ORGANISM: Homo sapiens
<220> FEATURE:
<223> OTHER INFORMATION: Vk1_L12 FW4

<400> SEQUENCE: 174

```
Phe Gly Gln Gly Thr Lys Leu Glu Ile Lys Arg
1               5                   10
```

<210> SEQ ID NO 175
<211> LENGTH: 212
<212> TYPE: PRT
<213> ORGANISM: Homo sapiens
<220> FEATURE:
<223> OTHER INFORMATION: Phe102Glu mutant full length IL-6

<400> SEQUENCE: 175

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Glu Gln Ser Gly Phe Asn Glu Glu Thr Cys Leu
            100                 105                 110
```

```
Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
        130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                    165                 170                 175

Thr Lys Leu Gln Ala Gln Asn Gln Trp Leu Gln Asp Met Thr Thr His
                180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 176
<211> LENGTH: 212
<212> TYPE: PRT
<213> ORGANISM: Homo sapiens
<220> FEATURE:
<223> OTHER INFORMATION: Ser204Glu mutant full length IL-6

<400> SEQUENCE: 176

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
                20                  25                  30

Gly Glu Asp Ser Lys Asp Val Ala Ala Pro His Arg Gln Pro Leu Thr
            35                  40                  45

Ser Ser Glu Arg Ile Asp Lys Gln Ile Arg Tyr Ile Leu Asp Gly Ile
        50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
        130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                    165                 170                 175

Thr Lys Leu Gln Ala Gln Asn Gln Trp Leu Gln Asp Met Thr Thr His
                180                 185                 190

Leu Ile Leu Arg Ser Phe Lys Glu Phe Leu Gln Glu Ser Leu Arg Ala
        195                 200                 205

Leu Arg Gln Met
    210

<210> SEQ ID NO 177
<211> LENGTH: 212
<212> TYPE: PRT
<213> ORGANISM: Homo sapiens
<220> FEATURE:
```

<223> OTHER INFORMATION: Arg207Glu mutant full length IL-6

<400> SEQUENCE: 177

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Glu Ala
        195                 200                 205

Leu Arg Gln Met
    210
```

<210> SEQ ID NO 178
<211> LENGTH: 212
<212> TYPE: PRT
<213> ORGANISM: Homo sapiens
<220> FEATURE:
<223> OTHER INFORMATION: Phe106Glu mutant full length IL-6

<400> SEQUENCE: 178

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Glu Asn Glu Glu Thr Cys Leu
            100                 105                 110

Val Lys Ile Ile Thr Gly Leu Leu Glu Phe Glu Val Tyr Leu Glu Tyr
        115                 120                 125
```

```
Leu Gln Asn Arg Phe Glu Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
            195                 200                 205

Leu Arg Gln Met
    210

<210> SEQ ID NO 179
<211> LENGTH: 212
<212> TYPE: PRT
<213> ORGANISM: Homo sapiens
<220> FEATURE:
<223> OTHER INFORMATION: Gln211Ala mutant full length IL-6

<400> SEQUENCE: 179

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
            35                  40                  45

Ser Ser Glu Arg Ile Asp Lys Gln Ile Arg Tyr Ile Leu Asp Gly Ile
50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
            115                 120                 125

Leu Gln Asn Arg Phe Glu Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
            195                 200                 205

Leu Arg Ala Met
    210

<210> SEQ ID NO 180
<211> LENGTH: 212
<212> TYPE: PRT
<213> ORGANISM: Homo sapiens
<220> FEATURE:
<223> OTHER INFORMATION: Arg58Glu mutant full length IL-6
```

<400> SEQUENCE: 180

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Glu Tyr Ile Leu Asp Gly Ile
50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
            85                  90                  95

Glu Lys Asp Gly Cys Phe Gln Ser Gly Phe Asn Glu Glu Thr Cys Leu
        100                 105                 110

Val Lys Ile Ile Thr Gly Leu Leu Glu Phe Glu Val Tyr Leu Glu Tyr
    115                 120                 125

Leu Gln Asn Arg Phe Glu Ser Ser Glu Glu Gln Ala Arg Ala Val Gln
130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210
```

<210> SEQ ID NO 181
<211> LENGTH: 212
<212> TYPE: PRT
<213> ORGANISM: Homo sapiens
<220> FEATURE:
<223> OTHER INFORMATION: Glu200Trp mutant full length IL-6

<400> SEQUENCE: 181

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
            85                  90                  95

Glu Lys Asp Gly Cys Phe Gln Ser Gly Phe Asn Glu Glu Thr Cys Leu
        100                 105                 110

Val Lys Ile Ile Thr Gly Leu Leu Glu Phe Glu Val Tyr Leu Glu Tyr
    115                 120                 125

Leu Gln Asn Arg Phe Glu Ser Ser Glu Glu Gln Ala Arg Ala Val Gln
```

```
                130                 135                 140
Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
                180                 185                 190

Leu Ile Leu Arg Ser Phe Lys Trp Phe Leu Gln Ser Ser Leu Arg Ala
                195                 200                 205

Leu Arg Gln Met
    210

<210> SEQ ID NO 182
<211> LENGTH: 212
<212> TYPE: PRT
<213> ORGANISM: Homo sapiens
<220> FEATURE:
<223> OTHER INFORMATION: Arg207Leu mutant full length IL-6

<400> SEQUENCE: 182

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
                20                  25                  30

Gly Glu Asp Ser Lys Asp Val Ala Ala Pro His Arg Gln Pro Leu Thr
                35                  40                  45

Ser Ser Glu Arg Ile Asp Lys Gln Ile Arg Tyr Ile Leu Asp Gly Ile
50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
                100                 105                 110

Val Lys Ile Ile Thr Gly Leu Leu Glu Phe Glu Val Tyr Leu Glu Tyr
                115                 120                 125

Leu Gln Asn Arg Phe Glu Ser Ser Glu Glu Gln Ala Arg Ala Val Gln
                130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
                180                 185                 190

Leu Ile Leu Arg Ser Phe Lys Glu Phe Leu Gln Ser Ser Leu Leu Ala
                195                 200                 205

Leu Arg Gln Met
    210

<210> SEQ ID NO 183
<211> LENGTH: 33
<212> TYPE: DNA
<213> ORGANISM: Macaca fascicularis
<220> FEATURE:
<223> OTHER INFORMATION: Primer macIL6_5'NdeI

<400> SEQUENCE: 183
```

```
ttatcatatg gtactcccag gagaagattc caa                          33

<210> SEQ ID NO 184
<211> LENGTH: 30
<212> TYPE: DNA
<213> ORGANISM: Macaca fascicularis
<220> FEATURE:
<223> OTHER INFORMATION: Primer macIL6_3'NheI

<400> SEQUENCE: 184
ttatgctagc ctacatttgc cgaagagccc                              30

<210> SEQ ID NO 185
<211> LENGTH: 32
<212> TYPE: DNA
<213> ORGANISM: Homo sapiens
<220> FEATURE:
<223> OTHER INFORMATION: Primer hIL6_5'NdeI

<400> SEQUENCE: 185
ttatacatat ggtaccccca ggagaagatt cc                           32
```